(12) United States Patent
Blott et al.

(10) Patent No.: US 8,529,548 B2
(45) Date of Patent: Sep. 10, 2013

(54) WOUND TREATMENT APPARATUS AND METHOD

(75) Inventors: Patrick Lewis Blott, Barmby Moor (GB); Edward Yerbury Hartwell, Heslington (GB); Julian Lee-Webb, Copmanthorpe (GB); Derek Nicolini, Brough (GB); Clare Green, Crockey Hill (GB); Robin Paul Martin, Selby (GB)

(73) Assignee: Smith & Nephew PLC, London (GB)

( * ) Notice: Subject to any disclaimer, the term of this patent is extended or adjusted under 35 U.S.C. 154(b) by 231 days.

(21) Appl. No.: 12/976,949

(22) Filed: Dec. 22, 2010

(65) Prior Publication Data

US 2011/0213319 A1    Sep. 1, 2011

Related U.S. Application Data

(63) Continuation-in-part of application No. 10/599,722, filed as application No. PCT/GB2005/001603 on Apr. 27, 2005, now Pat. No. 8,105,295, which is a continuation-in-part of application No. 10/599,725, filed as application No. PCT/GB2005/001595 on Apr. 27, 2005, now Pat. No. 8,348,910, which is a continuation-in-part of application No. 10/599,728, filed as application No. PCT/GB2005/001612 on Apr. 27, 2005, now abandoned, which is a continuation-in-part of application No. 11/577,642, filed as application No. PCT/GB2005/004177 on Oct. 28, 2005, now Pat. No. 7,883,494, which is a continuation-in-part of application No. 11/919,355, filed as application No. PCT/GB2006/001551 on Apr. 27, 2006, now Pat. No. 8,235,955, which is a continuation-in-part of application No. 11/919,369, filed as application No. PCT/GB2006/001625 on Apr. 27, 2006, now abandoned, which is a continuation-in-part of application No. 12/066,578, filed as application No. PCT/GB2006/003421 on Sep. 15, 2006, now abandoned.

(30) Foreign Application Priority Data

| Apr. 27, 2004 | (GB) | 0409444.7 |
| Apr. 28, 2004 | (GB) | 0409443.9 |
| Apr. 28, 2004 | (GB) | 0409446.2 |
| Oct. 29, 2004 | (GB) | 0424046.1 |
| Apr. 27, 2005 | (GB) | 0508528.7 |
| Apr. 27, 2005 | (GB) | 0508529.5 |
| Sep. 15, 2005 | (GB) | 0518825.5 |

(51) Int. Cl.
*A61M 27/00*    (2006.01)

(52) U.S. Cl.
USPC .................. 604/543; 604/313; 604/305

(58) Field of Classification Search
USPC .......... 604/313, 315, 316, 317, 540, 543
See application file for complete search history.

(56) References Cited

U.S. PATENT DOCUMENTS

| 2,280,915 A | 4/1941 | Johnson |
| 2,910,763 A | 8/1955 | Lauterbach |

(Continued)

FOREIGN PATENT DOCUMENTS

| CA | 2 369 022 | 10/2001 |
| CA | 2 369 024 | 10/2001 |

(Continued)

OTHER PUBLICATIONS

U.S. Appl. No. 10/576,263, filed Nov. 9, 2006, published as 2007/0141128, and its ongoing prosecution history including without limitation, Office Actions, Amendments, Remarks, and any other potentially relevant documents.

(Continued)

*Primary Examiner* — Susan Su

(74) *Attorney, Agent, or Firm* — Knobbe, Martens, Olson & Bear LLP

(57) ABSTRACT

An apparatus and method for aspirating, irrigating and/or cleansing wounds is provided. The apparatus and method include one or more of the following: simultaneous aspiration and irrigation of the wound, supplying of thermal energy to fluid circulated through the wound; supplying physiologically active agents to the wound; a biodegradable scaffold in contact with the wound bed; and application of stress or flow stress to the wound bed.

21 Claims, 31 Drawing Sheets

(56) References Cited

U.S. PATENT DOCUMENTS

| | | |
|---|---|---|
| 3,624,821 A | 11/1971 | Henderson |
| 3,874,387 A | 4/1975 | Barbieri |
| 3,993,080 A | 11/1976 | Loseff |
| 4,112,947 A | 9/1978 | Nehring |
| 4,136,696 A | 1/1979 | Nehring |
| 4,178,938 A | 12/1979 | Au |
| 4,180,074 A | 12/1979 | Murry et al. |
| 4,184,510 A | 1/1980 | Murry et al. |
| 4,224,945 A | 9/1980 | Cohen |
| 4,316,466 A | 2/1982 | Babb |
| 4,382,441 A | 5/1983 | Svedman |
| 4,465,485 A | 8/1984 | Kashmer et al. |
| 4,466,431 A | 8/1984 | Tharrat et al. |
| 4,529,402 A | 7/1985 | Weilbacher et al. |
| 4,573,965 A | 3/1986 | Russo |
| 4,740,202 A | 4/1988 | Stacey |
| 4,778,446 A | 10/1988 | Jensen |
| 4,792,328 A | 12/1988 | Beck et al. |
| 4,841,962 A | 6/1989 | Berg et al. |
| 4,921,488 A | 5/1990 | Maitz et al. |
| 4,936,834 A | 6/1990 | Beck et al. |
| 4,950,483 A | 8/1990 | Ksander et al. |
| 4,969,880 A | 11/1990 | Zamierowski |
| 5,010,883 A | 4/1991 | Rawlings et al. |
| 5,030,202 A | 7/1991 | Harris |
| 5,055,198 A | 10/1991 | Shettigar |
| 5,073,172 A | 12/1991 | Fell |
| 5,100,396 A | 3/1992 | Zamierowski |
| 5,176,663 A | 1/1993 | Svedman et al. |
| 5,261,893 A | 11/1993 | Zamierowski |
| 5,328,614 A | 7/1994 | Matsumura |
| 5,358,494 A | 10/1994 | Svedman |
| 5,360,398 A | 11/1994 | Grieshaber et al. |
| 5,380,280 A | 1/1995 | Peterson |
| 5,466,229 A | 11/1995 | Elson et al. |
| 5,487,889 A | 1/1996 | Eckert et al. |
| 5,498,338 A | 3/1996 | Kruger et al. |
| 5,549,584 A | 8/1996 | Gross |
| 5,636,643 A | 6/1997 | Argenta et al. |
| 5,645,081 A | 7/1997 | Argenta et al. |
| 5,676,650 A | 10/1997 | Grieshaber et al. |
| 5,678,564 A | 10/1997 | Lawrence et al. |
| 5,716,411 A | 2/1998 | Orgill et al. |
| 5,759,570 A | 6/1998 | Arnold |
| 5,795,584 A | 8/1998 | Totakura et al. |
| 5,810,765 A | 9/1998 | Oda |
| 5,830,176 A | 11/1998 | Mackool |
| 5,904,659 A | 5/1999 | Duarte |
| 5,911,222 A | 6/1999 | Lawrence et al. |
| 5,954,680 A | 9/1999 | Augustine |
| 6,071,267 A | 6/2000 | Zamierowski |
| 6,110,197 A | 8/2000 | Augustine et al. |
| 6,159,160 A | 12/2000 | Hsei et al. |
| 6,254,567 B1 | 7/2001 | Treu et al. |
| 6,398,767 B1 | 6/2002 | Fleischmann |
| 6,458,109 B1 | 10/2002 | Henley et al. |
| 6,465,708 B1 | 10/2002 | Augustine |
| 6,520,982 B1 | 2/2003 | Boynton et al. |
| 6,626,827 B1 | 9/2003 | Felix et al. |
| 6,648,862 B2 | 11/2003 | Watson |
| 6,676,610 B2 | 1/2004 | Morton et al. |
| 6,685,681 B2 | 2/2004 | Lockwood et al. |
| 6,695,823 B1 | 2/2004 | Lina et al. |
| 6,695,824 B2 | 2/2004 | Howard et al. |
| 6,752,794 B2 | 6/2004 | Lockwood et al. |
| 6,755,807 B2 | 6/2004 | Risk et al. |
| 6,764,462 B2 | 7/2004 | Risk, Jr. et al. |
| 6,794,554 B2 | 9/2004 | Sessions et al. |
| 6,800,074 B2 | 10/2004 | Henley et al. |
| 6,824,533 B2 | 11/2004 | Risk, Jr. et al. |
| 6,855,135 B2 | 2/2005 | Lockwood et al. |
| 6,936,037 B2 | 8/2005 | Bubb et al. |
| 6,951,553 B2 | 10/2005 | Bubb et al. |
| 7,004,915 B2 | 2/2006 | Boynton et al. |
| 7,022,113 B2 | 4/2006 | Lockwood et al. |
| 7,070,584 B2 | 7/2006 | Johnson et al. |
| 7,077,832 B2 | 7/2006 | Fleischmann |
| 7,108,683 B2 | 9/2006 | Zamierowski |
| 7,144,390 B1 | 12/2006 | Hannigan et al. |
| 7,182,758 B2 | 2/2007 | McCraw |
| 7,195,624 B2 | 3/2007 | Lockwood |
| 7,216,651 B2 | 5/2007 | Argenta et al. |
| 7,381,859 B2 | 6/2008 | Hunt et al. |
| 7,494,482 B2 | 2/2009 | Orgill et al. |
| 7,503,910 B2 | 3/2009 | Adahan |
| 7,524,315 B2 | 4/2009 | Blott et al. |
| 7,534,240 B1 | 5/2009 | Johnson |
| 7,534,859 B2 | 5/2009 | Messing et al. |
| 7,534,927 B2 | 5/2009 | Lockwood et al. |
| 7,540,848 B2 | 6/2009 | Hannigan et al. |
| 7,569,742 B2 | 8/2009 | Haggstrom et al. |
| 7,611,500 B1 | 11/2009 | Lina et al. |
| 7,625,362 B2 | 12/2009 | Boehringer et al. |
| 7,678,090 B2 | 3/2010 | Risk, Jr. et al. |
| 7,699,830 B2 | 4/2010 | Martin |
| 7,753,894 B2 | 7/2010 | Blott et al. |
| 7,759,537 B2 | 7/2010 | Bishop et al. |
| 7,759,538 B2 | 7/2010 | Fleischmann |
| 7,794,450 B2 | 9/2010 | Blott et al. |
| 7,828,782 B2 | 11/2010 | Suzuki |
| 7,846,141 B2 | 12/2010 | Weston |
| 7,883,494 B2 | 2/2011 | Martin et al. |
| 7,964,766 B2 | 6/2011 | Blott et al. |
| 8,080,702 B2 | 12/2011 | Blott et al. |
| 8,098,473 B2 | 1/2012 | Locke et al. |
| 8,105,295 B2 | 1/2012 | Blott et al. |
| 8,128,615 B2 | 3/2012 | Blott et al. |
| 8,162,909 B2 | 4/2012 | Blott et al. |
| 8,235,955 B2 | 8/2012 | Blott et al. |
| 8,257,327 B2 | 9/2012 | Blott et al. |
| 8,348,910 B2 | 1/2013 | Blott et al. |
| 2001/0029956 A1 | 10/2001 | Argenta |
| 2001/0034499 A1 | 10/2001 | Sessions et al. |
| 2001/0043943 A1 | 11/2001 | Coffey |
| 2002/0016570 A1 | 2/2002 | Cartledge |
| 2002/0068913 A1 | 6/2002 | Fleischmann |
| 2002/0115952 A1 | 8/2002 | Johnson |
| 2002/0138036 A1 | 9/2002 | Babaev |
| 2002/0161346 A1 | 10/2002 | Lockwood et al. |
| 2002/0198503 A1 | 12/2002 | Risk et al. |
| 2003/0021775 A1 | 1/2003 | Freeman |
| 2003/0050594 A1* | 3/2003 | Zamierowski ............... 604/46 |
| 2003/0108587 A1 | 6/2003 | Orgill et al. |
| 2003/0144619 A1 | 7/2003 | Augustine |
| 2003/0171675 A1 | 9/2003 | Rosenberg |
| 2003/0225347 A1 | 12/2003 | Argenta et al. |
| 2004/0054338 A1 | 3/2004 | Bybordi et al. |
| 2005/0004534 A1 | 1/2005 | Lockwood et al. |
| 2005/0065484 A1 | 3/2005 | Watson et al. |
| 2005/0090787 A1 | 4/2005 | Risk et al. |
| 2005/0107756 A1* | 5/2005 | McCraw ................... 604/317 |
| 2005/0130299 A1 | 6/2005 | Suzuki |
| 2005/0164365 A1 | 7/2005 | Yonemura et al. |
| 2005/0177190 A1 | 8/2005 | Zamierowski |
| 2005/0209574 A1 | 9/2005 | Boehringer et al. |
| 2005/0261643 A1 | 11/2005 | Bybordi et al. |
| 2006/0029675 A1 | 2/2006 | Ginther |
| 2006/0189910 A1 | 8/2006 | Johnson et al. |
| 2007/0014837 A1 | 1/2007 | Johnson et al. |
| 2007/0038172 A1 | 2/2007 | Zamierowski |
| 2007/0073200 A1 | 3/2007 | Hannigan et al. |
| 2007/0078366 A1 | 4/2007 | Haggstrom et al. |
| 2007/0141128 A1 | 6/2007 | Blott et al. |
| 2007/0219471 A1 | 9/2007 | Johnson et al. |
| 2007/0219497 A1 | 9/2007 | Johnson et al. |
| 2007/0239078 A1 | 10/2007 | Jaeb |
| 2007/0292488 A1 | 12/2007 | Bassirie et al. |
| 2007/0299412 A1 | 12/2007 | Vogel |
| 2008/0033330 A1 | 2/2008 | Moore |
| 2008/0069855 A1 | 3/2008 | Bonutti |
| 2008/0091133 A1 | 4/2008 | Matter |
| 2008/0125697 A1 | 5/2008 | Gao |
| 2008/0125698 A1 | 5/2008 | Gert et al. |
| 2009/0054855 A1 | 2/2009 | Blott et al. |

| | | | |
|---|---|---|---|
| 2009/0069759 A1 | 3/2009 | Blott et al. | |
| 2009/0093550 A1 | 4/2009 | Rolfes et al. | |
| 2009/0105671 A1 | 4/2009 | Daggar et al. | |
| 2009/0143753 A1 | 6/2009 | Blott et al. | |
| 2009/0204084 A1 | 8/2009 | Blott et al. | |
| 2009/0221977 A1 | 9/2009 | Blott et al. | |
| 2009/0234260 A1 | 9/2009 | Coward et al. | |
| 2009/0254054 A1 | 10/2009 | Blott et al. | |
| 2009/0306580 A1 | 12/2009 | Blott et al. | |
| 2009/0306609 A1 | 12/2009 | Blott et al. | |
| 2009/0312723 A1 | 12/2009 | Blott et al. | |
| 2010/0274167 A1 | 10/2010 | Martin | |
| 2011/0004171 A1 | 1/2011 | Blott et al. | |
| 2011/0009835 A1 | 1/2011 | Blott et al. | |
| 2011/0054423 A1 | 3/2011 | Blott et al. | |
| 2011/0213320 A1 | 9/2011 | Blott et al. | |
| 2011/0251567 A1 | 10/2011 | Blott et al. | |
| 2012/0004628 A1 | 1/2012 | Blott et al. | |
| 2012/0041399 A1 | 2/2012 | Blott et al. | |
| 2012/0109084 A1 | 5/2012 | Blott et al. | |

FOREIGN PATENT DOCUMENTS

| | | |
|---|---|---|
| DE | 847475 | 8/1952 |
| DE | 3935818 A1 | 5/1991 |
| DE | 40 12 232 A1 | 10/1991 |
| DE | 41 02 684 A1 | 8/1992 |
| DE | 197 22 075 | 10/1998 |
| DE | 198 44 355 | 4/2000 |
| EP | 0020662 B1 | 7/1984 |
| EP | 0 355 186 A1 | 2/1990 |
| EP | 0 777 504 B1 | 8/1995 |
| EP | 0 853 950 B1 | 8/1995 |
| EP | 0 880 953 B1 | 5/1998 |
| EP | 777504 B1 | 10/1998 |
| EP | 853950 B1 | 10/2002 |
| EP | 1 488 816 A1 | 12/2004 |
| EP | 1 614 789 A1 | 1/2006 |
| FR | 1 163 907 | 10/1958 |
| GB | 114754 | 4/1918 |
| GB | 641061 | 8/1950 |
| GB | 1 224 009 A | 3/1971 |
| GB | 1 549 756 | 8/1979 |
| GB | 1549756 A | 8/1979 |
| GB | 2 195 255 A | 4/1988 |
| GB | 2 307 180 A | 5/1997 |
| GB | 2378392 A | 2/2003 |
| JP | 2001-314479 | 11/2001 |
| SU | 1251912 A1 | 4/1983 |
| WO | WO 84/01904 | 5/1984 |
| WO | WO 87/00759 | 2/1987 |
| WO | WO 90/11795 | 10/1990 |
| WO | WO 91/00718 | 1/1991 |
| WO | WO 92/19313 | 11/1992 |
| WO | WO 92/20299 | 11/1992 |
| WO | WO 93/09727 | 5/1993 |
| WO | WO 94/03214 | 2/1994 |
| WO | WO 98/13000 | 4/1998 |
| WO | WO 99//48621 | 9/1999 |
| WO | WO 99/56829 | 11/1999 |
| WO | WO 00/07653 | 2/2000 |
| WO | WO 00/50143 A | 8/2000 |
| WO | WO 01/37773 | 5/2001 |
| WO | WO 02/083046 A1 | 10/2002 |
| WO | WO 02/092783 | 11/2002 |
| WO | WO 03/072748 | 9/2003 |
| WO | WO 03/074100 | 9/2003 |
| WO | WO 03/101385 | 11/2003 |
| WO | WO 03/101508 | 12/2003 |
| WO | WO 2004/024300 | 3/2004 |
| WO | WO 2004/037334 | 5/2004 |
| WO | WO 2005/046760 | 5/2005 |
| WO | WO 2005/046761 | 5/2005 |
| WO | WO 2005/046762 | 5/2005 |
| WO | WO 2005/051461 | 6/2005 |
| WO | WO 2005/070480 | 8/2005 |
| WO | WO 2005/082435 | 9/2005 |
| WO | WO 2005/105174 | 11/2005 |
| WO | WO 2005/105175 | 11/2005 |
| WO | WO 2005/105176 | 11/2005 |
| WO | WO 2005/105180 | 11/2005 |
| WO | WO 2006/052745 | 5/2006 |
| WO | WO 2006/054323 | 5/2006 |
| WO | WO 2006/099137 | 9/2006 |
| WO | WO 2006/114638 | 11/2006 |
| WO | WO 2007/013064 | 2/2007 |
| WO | WO 2007/019038 | 2/2007 |
| WO | WO 2007/084792 A2 | 7/2007 |
| WO | WO 2008/005532 | 1/2008 |
| WO | WO 2008/005996 | 1/2008 |
| WO | WO 2008/0008032 | 1/2008 |
| WO | WO 2008/010094 | 1/2008 |
| WO | WO 2008/028975 | 3/2008 |
| WO | WO 2008/030872 | 3/2008 |
| WO | WO 2008/036360 | 3/2008 |
| WO | WO 2008/039314 | 4/2008 |
| WO | WO 2008/040020 | 4/2008 |
| WO | WO 2008/041926 | 4/2008 |

OTHER PUBLICATIONS

U.S. Appl. No. 10/599,725, filed Sep. 22, 2008, published as 2009/0069759, and its ongoing prosecution history including without limitation, Office Actions, Amendments, Remarks, and any other potentially relevant documents.

U.S. Appl. No. 12/094,963, filed Sep. 23, 2008, published as 2009/0105671, and its ongoing prosecution history including without limitation, Office Actions, Amendments, Remarks, and any other potentially relevant documents.

U.S. Appl. No. 12/066,730, filed Oct. 9, 2008, published as 2009/0143753, and its ongoing prosecution history including without limitation, Office Actions, Amendments, Remarks, and any other potentially relevant documents.

U.S. Appl. No. 12/066,585, filed Sep. 29, 2008, published as 2009/0204084, and its ongoing prosecution history including without limitation, Office Actions, Amendments, Remarks, and any other potentially relevant documents.

U.S. Appl. No. 12/066,578, filed Oct. 10, 2008, published as 2009/0221977, and its ongoing prosecution history including without limitation, Office Actions, Amendments, Remarks, and any other potentially relevant documents.

U.S. Appl. No. 12/416,829, filed Apr. 1, 2009, published as 2009/0254054, and its ongoing prosecution history including without limitation, Office Actions, Amendments, Remarks, and any other potentially relevant documents.

U.S. Appl. No. 11/919,355, filed Nov. 17, 2008, published as 2009/0306609, and its ongoing prosecution history including without limitation, Office Actions, Amendments, Remarks, and any other potentially relevant documents.

U.S. Appl. No. 11/919,354, filed Nov. 19, 2008, published as 2009/0306580, and its ongoing prosecution history including without limitation, Office Actions, Amendments, Remarks, and any other potentially relevant documents.

U.S. Appl. No. 11/919,369, filed Nov. 17, 2008, published as 2009/0312723, and its ongoing prosecution history including without limitation, Office Actions, Amendments, Remarks, and any other potentially relevant documents.

U.S. Appl. No. 12/762,250, filed Apr. 16, 2010, published as 2010/0274167, and its ongoing prosecution history including without limitation, Office Actions, Amendments, Remarks, and any other potentially relevant documents.

U.S. Appl. No. 12/832,002, filed Jul. 7, 2010, published as 2011/0004171, and its ongoing prosecution history including without limitation, Office Actions, Amendments, Remarks, and any other potentially relevant documents.

U.S. Appl. No. 12/832,032, filed Jul. 7, 2010, published as 2011/0009835, and its ongoing prosecution history including without limitation, Office Actions, Amendments, Remarks, and any other potentially relevant documents.

U.S. Appl. No. 12/940,788, filed Nov. 5, 2010, published as 2011/0054423, and its ongoing prosecution history including without limitation, Office Actions, Amendments, Remarks, and any other potentially relevant documents.

U.S. Appl. No. 12/976,935, filed Dec. 22 2010, and its ongoing prosecution history including without limitation, Office Actions, Amendments, Remarks, and any other potentially relevant documents.

U.S. Appl. No. 12/981,337, filed Dec. 29, 2010, published as 2011/0251567, and its ongoing prosecution history including without limitation, Office Actions, Amendments, Remarks, and any other potentially relevant documents.

U.S. Appl. No. 13/212,039, filed Aug. 17, 2011, and its ongoing prosecution history including without limitation, Office Actions, Amendments, Remarks, and any other potentially relevant documents, Blott et al.

U.S. Appl. No. 13/217,074, filed Aug. 24, 2011, and its ongoing prosecution history including without limitation, Office Actions, Amendments, Remarks, and any other potentially relevant documents, Blott et al.

U.S. Appl. No. 13/302,980, filed Nov. 22, 2011, and its ongoing prosecution history including without limitation, Office Actions, Amendments, Remarks, and any other potentially relevant documents, Blott et al.

Application for Modification to HCPCS Level II Code Set in the 2005-2006 Coding Cycle. www.cms.hhs.gov/medicare/hcpcs/.

Aubrey, D.A., et al., Treatment of the Perineal Wound after Proctectomy by Intermittent Irrigation, Arch. Surg., Oct. 1984, vol. 119, pp. 1141-1144.

Bagautdinov, N. A., "Variant of External Vacuum Aspiration in the Treatment of Purulent Diseases of Soft Tissues," in current Problems in Modern Clinical Surgery: Interdepartmental Collection, edited by V. Ye. Volkov et al. (Chuvashia State University, Cheboksary, USSR 1986) pp. 94-96 (with English translation).

Boretos, John W., Cellular Polymers for Medical Use: The Vital Role of Porosity and Permeability, Cellular Polymers, 1984, vol. 3, pp. 345-358.

Chariker, M.E., et al, Effective Management of Incisional and Cutaneous Fistulae with Closed Suction Wound Drainage, Contemporary Surgery, Jun. 1989, vol. 34 USA, pp. 59-63.

Chernavskii, V. A., B. M. Mirazimov, *exerpt from* Free Skin Plasty of Wounds and Ulcers using the Vacuum Method, Meditsina Publishers of the Uzbek SSR, Tashkent 1970, pp. 5-37.

Dilmaghani et al., A Method for Closed Irrigation and Suction Therapy in Deep Wound Infections, Journal of Bone and Joint Surgery, 1969, vol. 51-A, No. 2, pp. 323-342.

Fleischmann, W., et al. Vacuum Sealing for Treatment of Soft Tissue Injury in Open Fractures, Emergency Surgery, 1993, vol. 96, pp. 488-492.

Greene, M. A., et al. Laparotomy Wound Closure with Absorable Polyglycolic Acid Mesh, Surgery, Gynecology and Obsterics 1993, vol. 176, pp. 213-218.

Hartz, R.S., et al., Healing of the Perineal Wound, Arch. Surg., Apr. 1980, vol. 115, pp. 471-474.

International Preliminary Report for International Application No. PCT/GB2006/001551, Date of Report Issuance Oct. 30, 2007 in 8 pages.

International Preliminary Report for International Application No. PCT/GB2005/001603 Dated of Report Issuance Nov. 1, 2006 in 7 pages.

International Preliminary Report for International Application No. PCT/GB2006/003421, Date of Report Issuance Mar. 18, 2008, in 7 pages.

International Preliminary Report for International Application No. PCT/GB2005/004177 Date of Issuance of Report May 1, 2007 in 8 pages.

International Preliminary Report in Patentability, dated Nov. 1, 2006, received in International Application No. PCT/GB2005/001612 in 7 pages.

International Preliminary Report on Patentability, dated Mar. 18, 2008, received in International Application No. PCT/GB2006/03421 in 7 pages.

International Preliminary Report on Patentability, dated Mar. 18, 2008, received in International Application No. PCT/GB2006/03425 in 9 pages.

International Preliminary Report on Patentability, dated Mar. 18, 2008, received in International Application No. PCT/GB2006/03416 in 11 pages.

International Preliminary Report on Patentability, dated May 1, 2007, received in International Application No. PCT/GB2005/004177 in 8 pages.

International Preliminary Report on Patentability, dated Oct. 30, 2007, received in International Application No. PCT/GB2006/001551 in 8 pages.

International Preliminary Report on Patentability, dated Oct. 30, 2007, received in International Application No. PCT/GB2006/001625 in 8 pages.

International Preliminary Report on Patentability, dated Oct. 30, 2007, received in International Application No. PCT/GB2006/001552 in 8 pages.

International Preliminary Report on Patentability, dated Nov. 1, 2006, received International Application No. PCT/GB2005/001595 in 7 pages.

International Search Report for International Application No. PCT/GB2006/001551, Date of Mailing Jan. 19, 2007 in 4 pages.

International Search Report for International Application No. PCT/GB2006/001625, date of mailing Jan. 25, 2007 in 3 pages.

International Search Report for International Application No. PCT/GB2005/001603 Dated Jul. 27, 2005 in 4 pages.

International Search Report for International Application No. PCT/GB2006/003421, Date of Mailing Feb. 20, 2007, in 3 pages.

International Search Report for International Application No. PCT/GB2006/001552, date of mailing Jan. 17, 2007 in 4 pages.

International Search Report for International Application No. PCT/GB2005/001595, date of mailing of the International Search Report is Jul. 27, 2005, in 5 pages.

International Search Report in related PCT Application No. PCT/GB03/04647, date of mailing Feb. 25, 2004 in 3 pages.

International Search Report in related PCT Application No. PCT/GB2005/004177, date of mailing Jun. 29, 2006 in 4 pages.

International Search Report, dated Jan. 17, 2007, received in International Application No. PCT/GB2006/001552 in 4 pages.

International Search Report, dated Jan. 19, 2007, received in International Application No. PCT/GB2006/001551 in 4 pages.

International Search Report, dated Jan. 25, 2007, received in International Application No. PCT/GB2006/001625 in 3 pages.

International Search Report, dated Feb. 20, 2007, received in International Application No. PCT/GB2006/03421 in 3 pages.

International Search Report, dated Jun. 29, 2006, received in International Application No. PCT/GB2005/004177 in 4 pages.

International Search Report, dated Jul. 27, 2005, received in International Application No. PCT/GB2005/001595 in 5 pages.

International Search Report, dated Jul. 27, 2005, received in International Application No. PCT/GB2005/001612 in 4 pages.

International Search Report, dated Nov. 30, 2006, received in International Application No. PCT/GB2006/03416 in 4 pages.

International Search Report, dated Dec. 11, 2006, received in International Application No. PCT/GB2006/03425 in 5 pages.

Larichev, A.B., Vacuum Therapy of Wounds and Wound Infection, *1st. Ed., BlueSky Publishing, 2005*. 237 pgs.

Ma, Peter X. Scaffolds for Tissue Fabrication. Materials Today, Review, May 2004.

Middleton, J., A. Tipton (Mar. 1998). "Synthetic biodegradable polymers as medical devices" (HTML). Medical Plastics and Biomaterials Magazine.

Morykwas, M. J., et al., Vacuum-Assisted Closure: A New Method for Wound Control and Treatment: Animal Studies and Basic Foundation, Annals of Plastic Surgery, 1997, vol. 38, pp. 553-562.

Nursing75, Wound Suction: Better Drainage with Fewer Problems, Nursing, vol. 5, No. 10, Oct. 1975, pp. 52-55.

Solovev, V. A., et al., "The Method of Treatment of Immature External Fistulas in the Upper Gastrointestinal Tract—Guidelines" USSR Ministry of Health, S. M. Kirov Gorky State Medical Institute, 1987 (with English translation).

Stewart, Joanne, Ph.D., World Wide Wounds—Next generation of products for wound management—2002 (13 pages).

Svedman, P., A Dressing Allowing Continuous Treatment of a Biosurface, IRCS Med. Science: Biomed. Tech.; Clinic. Med.; Surg. and Transplantation, 1979, vol. 7, p. 221.

Svedman, P., Irrigation Treatment in Split-Thickness Skin Grafting of Intractable Leg Ulcers, Scand J. Plast. Reconst. Surg., 1985, vol. 19, pp. 211-213.

Svedman, P., Irrigation Treatment of Leg Ulcers, The Lancet, Sep. 1983, pp. 532-534.

Svedman, P. et al., A Dressing System Providing Fluid Supply and Suction Drainage Used for Continuous or Intermittent Irrigation, Annals of Plastic Surgery, vol. 17, No. 2, Aug. 1986, pp. 125-133.

Swift, et al, Quorum Sensing in *Aeromonas hydrophila and Aeromonas salmoncida*: Identification of LuxRI Homologs AhyRI and AsaRI and Their Cognate N-Acylhomoserine Lactone Signal Molecules, J. Bacteriol., 1997, vol. 179, No. 17, pp. 5271-5281.

Teder and Svedman et al., Continuous Wound Irrigation in the Pig, Journal of Investigative Surgery, 1990, vol. 3, pp. 399-407.

Thomas, Stephen, Wound Management and Dressings, 1990, pp. 35-42.

Tribble, David E. M.D., An Improved Sump Drain-Irrigation Device of Simple Construction, Archives of Surgery New York, 1972, vol. 105, pp. 511-513.

Urschel, J.D., et al., The Effect of Mechanical Stress on Soft and Hard Tissue Repair; A Review, Br. Journ. Plast. Surg., 1988, vol. 41, pp. 182-186.

Vijanto, J. and J. Raekallio, Local hyperalimentation of open wounds, British Journal Surgery, 1976, vol. 63, pp. 427-430.

Westaby, S., et al., A Wound Irrigation Device, The Lancet, Sep. 2, 1978, pp. 503-504.

Wooding-Scott, Margaret, et al., No Wound is Too Big for Resourceful Nurses, RN, USA, Dec. 1988, pp. 22-25.

Wound Suction, Nursing, Oct. 1975, USA pp. 52-53.

Written Opinion for International Application No. PCT/GB2005/001595 date of mailing Oct. 28, 2006 in 6 pages.

International Search Report in related PCT Application No. PCT/GB2004/004566, date of mailing Feb. 23, 2005 in 4 pages.

International Preliminary Report on Patentability, dated Dec. 13, 2005, received in International Application No. PCT/GB2004/004566 in 7 pages.

International Search Report in related PCT Application No. PCT/GB2004/004564, date of mailing Feb. 23, 2005 in 4 pages.

International Preliminary Report on Patentability, dated Dec. 13, 2005, received in International Application No. PCT/GB2004/004564 in 7 pages.

International Search Report in related PCT Application No. PCT/GB2004/004567, date of mailing Feb. 21, 2005 in 4 pages.

International Preliminary Report on Patentability, dated Dec. 13, 2005, received in International Application No. PCT/GB2004/004567 in 7 pages.

International Search Report in related PCT Application No. PCT/GB2005/001577, date of mailing Aug. 31, 2005 in 4 pages.

International Preliminary Report on Patentability, dated Nov. 1, 2006, received in International Application No. PCT/GB2005/001577 in 7 pages.

International Search Report in related PCT Application No. PCT/GB2005/001595, date of mailing Jul. 27, 2005 in 5 pages.

International Preliminary Report on Patentability, dated Nov. 1, 2006, received in International Application No. PCT/GB2005/001595 in 7 pages.

U.S. Appl. No. 10/652,074, filed Aug. 23, 2011, published as 2004/0073151, including its ongoing prosecution history, including without limitation Office Actions, Amendments, Remarks, and any other potentially relevant documents.

U.S. Appl. No. 10/576,263, filed Nov. 9, 2006, published as 2007/0141128, including its ongoing prosecution history, including without limitation Office Actions, Amendments, Remarks, and any other potentially relevant documents.

U.S. Appl. No. 10/599,725, filed Sep. 22, 2008, published as 2009/0069759, including its ongoing prosecution history, including without limitation Office Actions, Amendments, Remarks, and any other potentially relevant documents.

U.S. Appl. No. 12/066,585, filed Sep. 29, 2008, published as 2009/0204084, including its ongoing prosecution history, including without limitation Office Actions, Amendments, Remarks, and any other potentially relevant documents.

U.S. Appl. No. 11/919,355, filed Nov. 17, 2008, published as 2009/0306609, including its ongoing prosecution history, including without limitation Office Actions, Amendments, Remarks, and any other potentially relevant documents.

U.S. Appl. No. 12/762,250, filed Apr. 16, 2010, published as 2010/0274167, including its ongoing prosecution history, including without limitation Office Actions, Amendments, Remarks, and any other potentially relevant documents.

U.S. Appl. No. 10/599,722, filed Sep. 19, 2008, published as 2009/0012483, including its ongoing prosecution history, including without limitation Office Actions, Amendments, Remarks, and any other potentially relevant documents.

U.S. Appl. No. 13/212,039, filed Aug. 17, 2011, published as 2012/0041399, including its ongoing prosecution history, including without limitation Office Actions, Amendments, Remarks, and any other potentially relevant documents.

U.S. Appl. No. 13/302,980, filed Nov. 22, 2011, published as 2012/0109084, including its ongoing prosecution history, including without limitation Office Actions, Amendments, Remarks, and any other potentially relevant documents.

U.S. Appl. No. 13/213,491, filed Aug. 19, 2011, published as 2012/0004628, including its ongoing prosecution history, including without limitation Office Actions, Amendments, Remarks, and any other potentially relevant documents.

Bevan, Damon, et al.: "Diverse and potent activities of HGF/SF in skin wound repair", Journal of Pathology, J Pathol 2004; 203: 831-838.

Mitchell, Richard N., et al.: "Role of Stem Cells in Tissue Homeostasis", Pocket Companion to Robbins and Cotran Pathologic Basis of Disease, 7th Ed., 2006.

* cited by examiner

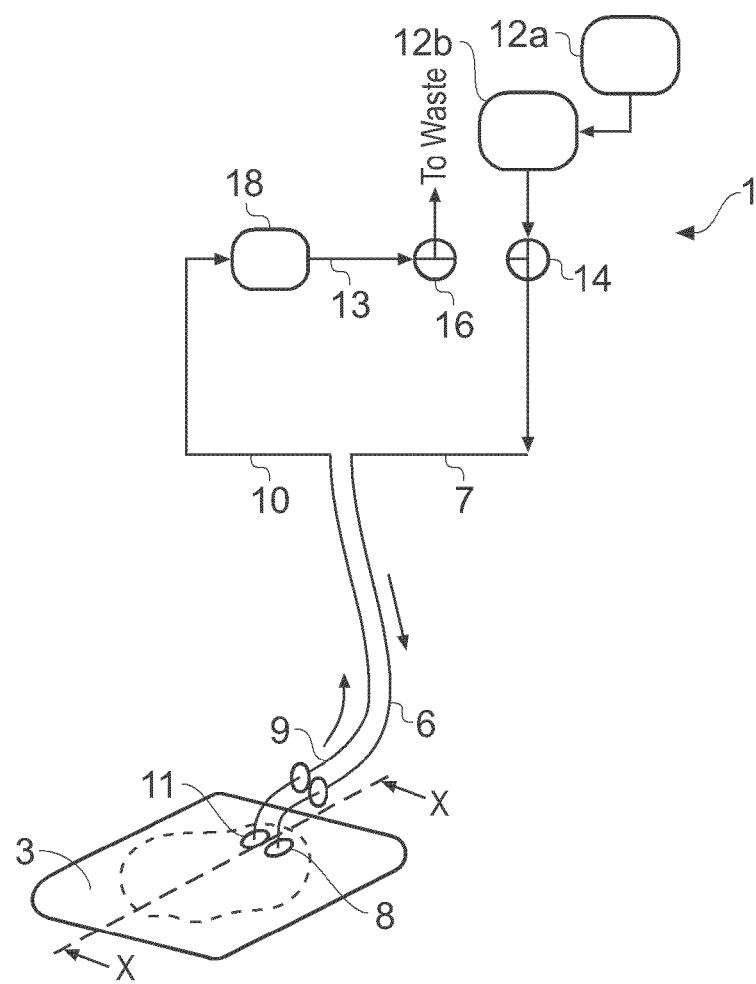
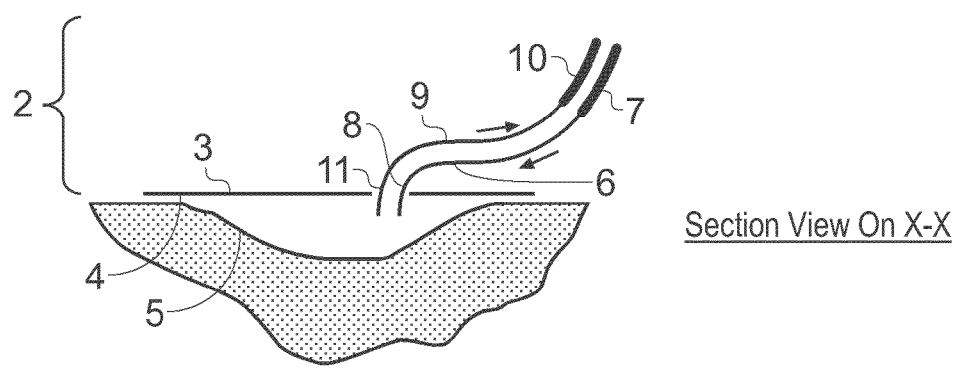
Fig. 1

Section Through X-X

Section Through X-X

Section Through X-X

Section Through X-X

Section Through X-X

Section Through X-X

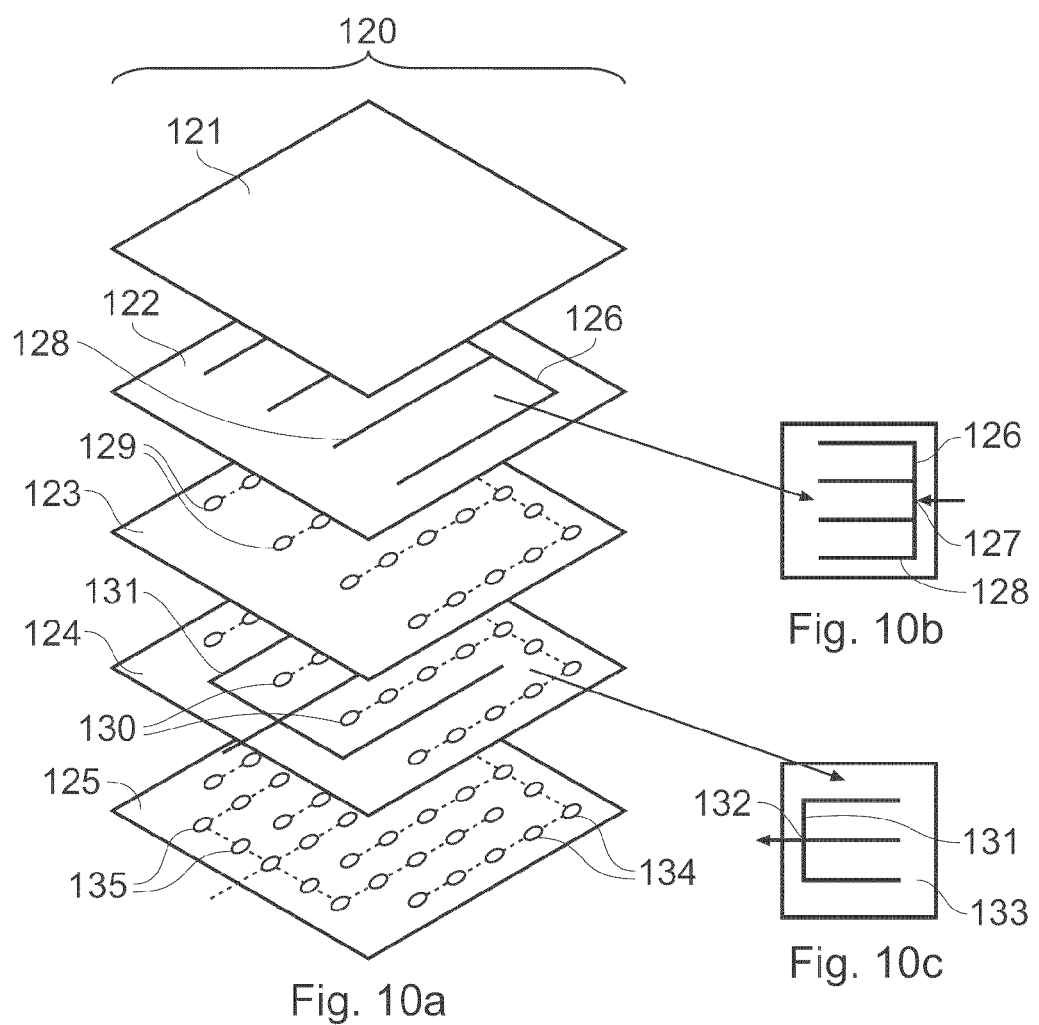

US 8,529,548 B2

WOUND TREATMENT APPARATUS AND METHOD

CROSS-REFERENCE TO RELATED APPLICATIONS

This application is a continuation-in-part of U.S. application Ser. No. 10/599,722, filed Sep. 19, 2008 now U.S. Pat. No. 8,105,295, which is a National Phase of PCT International Application No. PCT/GB2005/001603, filed Apr. 27, 2005, designating the United States and published on Mar. 11, 2005 as WO/2005/102415, which claims priority to Great Britain Patent Application No. 0409446.2, filed Apr. 28, 2004. This application is also a continuation-in-part of U.S. application Ser. No. 10/599,725, filed Sep. 22, 2008 now U.S. Pat. No. 8,348,910, which is a National Phase of PCT International Application No. PCT/GB2005/001595, filed Apr. 27, 2005, designating the United States and published on Oct. 11, 2005 as WO/2005/105179, which claims priority to Great Britain Application No. 0409444.7, filed Apr. 27, 2004. This application is also a continuation-in-part of U.S. application Ser. No. 10/599,728 filed Nov. 3, 2008 now abandoned, which is a U.S. National Phase of the PCT International Application No. PCT/GB2005/001612, filed on Apr. 27, 2005, designating the United States and published on Oct. 11, 2005 as WO/2005/105180, which claims priority to Great Britain Patent Application No. 0409443.9, filed Apr. 28, 2004. This application is also a continuation-in-part of U.S. application Ser. No. 11/577,642, filed Aug. 23, 2007 now U.S. Pat. No. 7,883,494, which is a National Phase of PCT International Application No. PCT/GB05/04177, filed Oct. 28, 2005, designating the United States and published on May 4, 2006 as WO/2006/046060, which claims priority to Great Britain Patent Application No. 0424046.1, filed Oct. 29, 2004. This application is also a continuation-in-part of U.S. application Ser. No. 11/919,355, filed Nov. 17, 2008 now U.S. Pat. No. 8,235,955, which is a National Phase of PCT International Application No. PCT/GB2006/001551, filed Apr. 27, 2006, designating the United States and published on Nov. 2, 2006 as WO/2006/114637, which claims priority to Great Britain Patent Application No. 0508528.7, filed Apr. 27, 2005. This application is also a continuation-in-part of U.S. application Ser. No. 11/919,369, filed Nov. 17, 2008 now abandoned, which is a National Phase of PCT International Application No. PCT/GB2006/001625, filed on Apr. 27, 2006, designating the United States and published on Nov. 2, 2006 as WO/2006/114648, which claims priority to Great Britain Patent Application No. 0508529.5, filed on Apr. 27, 2005. This application is also a continuation-in-part of U.S. application Ser. No. 12/066,578, filed Oct. 10, 2008 now abandoned, which is a U.S. National Phase of the PCT International Application No. PCT/GB06/03421, filed on Sep. 15, 2006, designating the United States and published on Mar. 22, 2007 as WO/2007/031762, which claims priority to Great Britain Patent Application No. 0518825.5, filed Sep. 15, 2005. The disclosures of these prior applications are hereby incorporated by reference in their entireties and should be considered part of this specification.

BACKGROUND OF THE INVENTION

1. Field of the Invention

The present invention relates to an apparatus and a medical wound dressing for aspirating, irrigating, and/or cleansing wounds, and a method of treating wounds using such apparatus for aspirating, irrigating, and/or cleansing wounds.

It relates in particular to such an apparatus, wound dressing and method that can be easily applied to a wide variety of, but in particular chronic, wounds, to cleanse them of materials that are deleterious to wound healing, whilst distributing materials that are beneficial in some therapeutic aspect, in particular to wound healing.

2. Description of the Related Art

Aspirating and/or irrigating apparatus are known, and tend to be used to remove wound exudate during wound therapy. In known forms of such wound therapy, aspiration and irrigation of the wound generally take place sequentially.

Such known forms of aspiration and/or irrigation therapy systems also often create a wound environment that may result in the loss of optimum performance of the body's own tissue healing processes, and slow healing, and/or in weak new tissue growth that does not have a strong three-dimensional structure adhering well to and growing from the wound bed. This is a significant disadvantage, in particular in chronic wounds.

SUMMARY OF THE INVENTION

Certain embodiments of the present invention are directed to an aspirating and/or irrigating apparatus that may be used to remove wound exudate during wound therapy. Each part of the therapy cycle is beneficial in promoting wound healing:

Aspiration applies a negative pressure to the wound, which is beneficial in itself in promoting wound healing by removing materials deleterious to wound healing with the wound exudate, reducing bacterial load, combating peri-wound oedema, increasing local blood flow to the wound and encouraging the formation of wound bed granulation tissue.

Irrigation cleanses wounds of materials that are deleterious to wound healing by diluting and moving wound exudate (which is typically relatively little fluid and may be of relatively high viscosity and particulate-filled).

Relatively little of beneficial materials involved in promoting wound healing (such as cytokines, enzymes, growth factors, extracellular cell matrix components and fragments thereof, biological signalling molecules and other physiologically active components of the exudate) are present in a wound, and are not well distributed in the wound, i.e. they are not necessarily present in parts of the wound bed where they can be potentially of most benefit. These may be distributed by irrigation of the wound and thus aid in promoting wound healing. The irrigant may contain active materials that are potentially or actually beneficial in respect of wound healing, such as nutrients for wound cells to aid proliferation, and gases, such as oxygen. These may be distributed by irrigation of the wound and thus aid in promoting wound healing.

If aspiration and irrigation therapy is applied sequentially to a wound, the two therapies, each of which is beneficial in promoting wound healing, can only be applied intermittently. Thus, the wound will lose the abovementioned known beneficial effects of aspiration therapy on wound healing, at least in part, while that aspiration is suspended during irrigation.

Additionally, for a given aspirate flow, whilst materials that are potentially or actually deleterious in respect of wound healing are removed from wound exudate, the removal in a given time period of application of the total irrigate and/or aspirate therapy will normally be less effective and/or slower than with continuous application of aspiration.

Even less to be desired, is that while aspiration is not applied to the wound, wound exudate and materials deleterious to wound healing (such as bacteria and debris, and iron II and iron III and for chronic wounds proteases, such as serine proteases) will pool on the wound bed and hinder wound healing, especially in a highly exuding wound. The influx of local oedema will also add to the chronicity of the wound. This is especially the case in chronic wounds.

Depending on the relative volumes of irrigant and wound exudate, the mixed exudate-irrigant fluid and may be of relatively high viscosity and/or particulate-filled. Once it is present and has pooled, it may be more difficult to shift by the application of aspiration in a conventional sequential aspirate—irrigate—dwell cycle than with continuous simultaneous aspiration and irrigation of the wound, owing to the viscosity and blockage in the system.

The wound will also lose the abovementioned beneficial effects of irrigation therapy on wound healing, at least in part, while that irrigation is suspended during aspiration. These benefits in promoting wound healing include the movement of materials that are beneficial in promoting wound healing, such as those mentioned above, and the supply in the irrigant of active amounts of materials that are beneficial in promoting wound healing which pass into and/or through the wound in contact with the wound bed.

Additionally, for a given irrigant flow, the cleansing of the wound and the distribution by irrigation of the wound of such beneficial materials and the supply in the irrigant of active amounts of materials that are beneficial in promoting wound healing in a given time period of application of the total irrigate and/or aspirate therapy when such therapy is in a conventional sequential aspirate—irrigate—dwell cycle will normally be less effective and/or slower than with continuous application of aspiration.

Additionally, aspirating and/or irrigating apparatus may be used for the delivery from cells or tissue of further materials that are beneficial in promoting wound healing. Examples of the latter include materials from cells or tissue, such as growth factors, extracellular matrix components and fragments thereof, selective proteases or fibrinolytic factors and combinations thereof.

It thus would be desirable to provide a system of aspiration and irrigation therapy for a wound, which can remove wound exudate and materials deleterious to wound healing from contact with the wound bed, whilst simultaneously cleansing it and distributing materials that are beneficial in promoting wound healing from cells or tissue across it. In some embodiments it would also be desirable to supply in the irrigant active amounts of materials that are beneficial in promoting wound healing which pass into and/or through the wound in contact with the wound bed. In some embodiments, it would be desirable to make the system portable.

Another advantage, in particular in chronic wounds, in providing apparatus for aspirating, irrigating, and/or cleansing a wound according to certain embodiments of the present invention is that it provides means for providing more than one therapy continuously in a single dressing. Embodiments of the present invention provide several further advantages.

One is that application of an irrigant to a wound under simultaneous aspiration and/or heating creates a wound environment that is exposed to the continuous beneficial effects of both aspects of the therapy for wound healing as opposed to the sequential intermittent application of irrigant flow and aspiration and/or heating in known aspirating and/or irrigating apparatus. The latter result in less than optimum performance of the body's own tissue healing processes, and slower healing, and/or weaker tissue growth that does not have a strong three-dimensional structure adhering well to and growing from the wound bed. This is a significant disadvantage, in particular in chronic wounds.

Thus, the use of the apparatus for aspirating, irrigating, and/or cleansing wounds retains and enhances the beneficial effects of aspiration in respect of wound healing by continuous and preferably constant aspiration. These include removing materials deleterious to wound healing with the wound exudate, reducing bacterial load, combating peri-wound oedema and encouraging the formation of wound bed granulation tissue.

Preferred embodiments of the apparatus for aspirating, irrigating, and/or cleansing chronic wounds apply a milder negative pressure than in conventional negative pressure therapy (which is too aggressive for the fragile tissues of many such wounds). This leads to increased patient comfort, and lessens the risk of inflammation of the wound. The removal of wound exudate in a given time period of application of the simultaneous irrigate and/or aspirate therapy will normally be more effective and/or faster than with a conventional sequential intermittent aspiration and/or irrigation therapy.

Even more desirably, since simultaneous aspiration and irrigation is applied to the wound, wound exudate and materials deleterious to wound healing (such as bacteria and debris, and iron II and iron III and for chronic wounds proteases) will not pool on the wound bed and hinder wound healing especially in a highly exuding wound. This is especially important in highly exuding wounds, e.g. chronic wounds. The resulting mixed exudate-irrigant fluid will usually be of relatively lower viscosity.

Because simultaneous aspiration and irrigation of the wound provides continuous removal at a constant relatively high speed, the fluid does not have to be accelerated cyclically from rest, and will be easier to shift than with known forms of aspiration and/or irrigation therapy systems with a conventional sequential aspirate—irrigate—dwell cycle. This will thus exert a greater net effect on the removal of adherent bacteria and debris. This is especially the case in those embodiments of the apparatus for aspirating, irrigating, and/or cleansing wounds where there is an inlet manifold (as described in further detail hereinafter) that covers and contacts most of the wound bed (scaffold) with openings that deliver the fluid directly to the wound bed (scaffold) over an extended area.

Additionally, it is generally believed that the body's own metabolic activities are at an optimum at or near the temperature naturally occurring in the relevant bodily part. Examples of metabolic molecules involved in tissue healing processes that are beneficial in promoting wound healing include enzymes, growth factors and anti-inflammatories, and other physiologically active components of the exudate from a wound. These are believed to act best at temperatures found in the relevant bodily part in which they occur, varying between normal temperatures found at the body surface and those at the body core. The body core is at a higher temperature than the surface, but surface temperatures at 33° C. and above are still relatively close to core body temperatures of 36 to 38° C. ('normothermic temperature'). Wounds, and in particular chronic wounds, may have a lower temperature, e.g. 24 to 26° C., i.e. substantially below the optimum temperature. Thus, the temperature of the wound itself is deleterious to wound healing.

This may result in slow wound healing, loss of cell proliferation, and/or growth that does not have a strong three-dimensional structure adhering well to and growing from the wound bed. Conventional wound aspiration and/or irrigation therapy systems thus often create a wound environment under a backing layer where (a) not only are beneficial materials lost to the site where they can be potentially of most benefit, i.e. the wound bed, when such therapy is applied, but (b) the wound healing processes, e.g. enzymic activity on tissue growth, are inhibited by sub-optimal temperatures. Heated dressings are known, but such forms of wound dressing do not simultaneously irrigate the wound environment under the backing layer. This will result in materials deleterious to wound healing in wound exudate being retained in the wound environment and hindering wound healing in spite of any stimulation of wound healing from wound temperature regulation.

There would thus be an advantage, in particular in chronic wounds, in providing means for more than one therapy in a single dressing (a) which not only removes materials deleterious to wound healing from wound exudate, whilst distributing materials that are beneficial in promoting wound healing in contact with the wound bed, but (b) promotes wound healing by creating a wound environment under the dressing with temperatures which stimulate the activity of metabolic molecules that are beneficial in promoting wound healing, e.g. temperatures near 36 to 38° C. ('normothermic temperature').

A disadvantage of known heated wound dressings is that it is imperative but not easy to avoid the heater, especially an electrical heater, from scorching the wound and/or surrounding surfaces. This is especially so when the dressing is in contact with the wound bed. Several devices for applying a dressing to the wound have been proposed. In one form, a stiff flange or lip extends around the periphery of the dressing to space the surface of the wound in use away from the heater. Such a wound dressing is cumbersome. Whilst it may be acceptable for hospital use, the stiff flange does little for patient comfort, and heightens the risk of inflammation of a wound and/or the leakage of wound exudate. There would be a further advantage in providing such a wound dressing that conforms to the shape of the bodily part to which it is applied.

In the prior art devices, vascular supply to, and circulation or aspiration in, tissue underlying and surrounding the wound is often compromised. Therefore, certain embodiments of the present invention provide a system of therapy that also promotes vascular supply to tissue underlying and surrounding a wound, promoting wound healing.

Certain embodiments of the present invention also provide a system of therapy which creates flow stress or strain across the wound bed surface, e.g. a shear flow gradient, e.g. by passing irrigant and/or wound exudate through the wound in a controllable stream, and optionally tissue surrounding the wound, e.g. by applying an optionally varying positive and/or negative pressure to the wound. Such a flow stress across a cell containing surface such as the wound bed, e.g. a shear flow gradient, has been found to result in effects that may be beneficial for wound healing.

According to one embodiment, an apparatus for aspirating, irrigating, and/or cleansing of wounds comprises (a) a fluid flow path, comprising a conformable wound dressing, having a backing layer which is capable of forming a relatively fluid-tight seal or closure over a wound and at least one inlet pipe for connection to a fluid supply tube, which passes through and/or under the wound-facing face, and at least one outlet pipe for connection to a fluid offtake tube, which passes through and/or under the wound-facing face to allow irrigation and/or aspiration of a wound, and wherein the point at which the at least one inlet pipe through and/or under the wound-facing face forming a relatively fluid-tight seal or closure over the wound; (b) a fluid reservoir connected by a fluid supply tube to an inlet pipe via optional means for supply flow regulation; (c) optionally means for aspirate flow regulation, connected to a fluid offtake tube; (d) optionally means for supplying physiologically active agents to the wound; and (e) at least one device for moving fluid through the wound dressing; characterised in that it comprises (f) means for providing simultaneous aspiration and irrigation of the wound, such that fluid may be supplied to fill the flowpath from the fluid reservoir via the fluid supply tube (optionally via means for supply flow regulation) while fluid is aspirated by a device through the fluid offtake tube (optionally or as necessary via means for aspirate flow regulation).

In another embodiment, the apparatus further comprises means for supplying thermal energy to the wound. In another embodiment, a biodegradable scaffold is located under the backing layer and configured to be placed in contact with a wound bed in use. In another embodiment, means for applying flow stress to the wound bed is also provided.

Where any pipe is described in connection with the operation of the apparatus as being connected or for connection to a (mating end of a) tube, e.g. a fluid supply tube, fluid offtake tube, the pipe and the tube may form a single integer in the flow path through which the circulating fluid from the wound passes.

Described below are examples of components and characteristics that may be included in the apparatus.

Fluid Reservoir and Container(s)

In one embodiment, the apparatus for aspirating, irrigating, and/or cleansing wounds is provided with means for admitting fluids directly or indirectly to the wound under the wound dressing in the form of a fluid supply tube to a fluid reservoir. The fluid reservoir may be of any conventional type, e.g. a tube, bag (such as a bag typically used for blood or blood products, e.g. plasma, or for infusion feeds, e.g. of nutrients), chamber, pouch or other structure, e.g. of polymer film, which can contain the irrigant fluid.

The reservoir may be made of a film, sheet or membrane, often with a (generally uniform) thickness similar to that of films or sheets used in conventional wound dressing backing layers, i.e. up to 100 micron, preferably up to 50 micron, more preferably up to 25 micron, and of 10 micron minimum thickness, and is often a resiliently flexible, e.g. elastomeric, and preferably soft, hollow body. In certain embodiments of the apparatus the type and material of the tubes throughout the apparatus for aspirating, irrigating, and/or cleansing wounds and the fluid reservoir will be largely determined by their function.

To be suitable for use, in particular on chronic timescales, the material should be non-toxic and biocompatible, inert to any active components, as appropriate of the irrigant from the fluid reservoir and/or wound exudate in the apparatus flow path, and, in any use of a two-phase system aspiration and irrigation unit, of the dialysate that moves into the aspirating fluid in the apparatus. When in contact with irrigant fluid, it should not allow any significant amounts of extractables to diffuse freely out of it in use of the apparatus.

It should be sterilizable by ultraviolet, gamma or electron beam irradiation and/or with fluid antiseptics, such as solutions of chemicals, fluid- and microbe-impermeable once in use, and flexible. Examples of suitable materials for the fluid reservoir include synthetic polymeric materials, such as polyolefins, such as polyethylene, e.g. high-density polyethylene and polypropylene. Suitable materials for the present purpose also include copolymers thereof, for example with vinyl acetate and mixtures thereof. Suitable materials for the present purpose further include medical grade poly(vinyl chloride).

Notwithstanding such polymeric materials, the fluid reservoir will often have a stiff area to resist any substantial play between it and components that are not mutually integral, such as the fluid supply tube towards the wound dressing, and may be stiffened, reinforced or otherwise strengthened, e.g. by a projecting boss.

The containers that contain the cell or tissue components may be, e.g. connected to a single supply tube by a Y-junction, and thence to the wound dressing, or they may, e.g. be connected to it by separate supply tubes, the two flows of physiologically active agents from cells or tissue optionally with irrigant and/or nutrient medium for the cells being optionally mutually admixed in the wound space under the wound dressing. In an alternative layout of this means for supplying physiologically active agents from cells or tissue to the wound, the first container, in which the first input cell or tissue type is contained, is in fluid communication in series with the second container, in which the second cell or tissue type is contained. Thus, they feed their physiologically active agents in series to the dressing and to the wound bed under the action of at least one device for moving fluid through the wound. In this layout of the means for supplying physiologically active agents from cells or tissue, the two containers effectively function as a single container.

Irrigant and/or nutrient medium for the cells or tissue is often fed through the containers of the cell or tissue components and thence to the wound dressing. In use, these layouts of the means for supplying physiologically active agents from cells or tissue to the wound will function in the apparatus exactly as for their analogues with a single cell or tissue type. The container that contains a cell or tissue component is often in the form of a hollow body such as an e.g. a canister, cartridge or cassette. It often has a chamber or compartment that contains a cell or tissue component, through which irrigant and/or a nutrient medium for the cells or tissue is passed. Where the container that contains a cell or tissue component lies outside the backing layer, the structure will often be made of glass, and/or synthetic polymeric materials. For example, such a structure may be a glass cylinder defining a chamber with axial inlet and outlet ports for throughflow, which contains cells or tissue on a scaffold.

Where the container that contains a cell or tissue component lies under the backing layer, the structure will often be made of a conformable synthetic polymeric material. Such a structure may still be a structure defining a chamber with an inlet port, which contains cells or tissue on a scaffold, and which communicates with the wound via at least one channel or conduit. The latter is/are for supplying physiologically active agents from cells or tissue and irrigant to the wound under the action of at least one device for moving fluid through the wound.

Where the container that contains a cell or tissue component is integral with the other components of the dressing, in particular the backing layer, it will usually be of the same polymeric material as the components. Where, alternatively, it is permanently or demountably attached to them/it, with an adhesive film, for example, or by heat-sealing, it may be of a different polymeric material. Any such structure may contain a cell or tissue component that is not bound to an insoluble and immobilised substrate over and/or through which the irrigant and/or wound exudate from the wound dressing passes. It then also appropriately comprises two or more integers which are permeable to the wound exudate or a mixture with irrigant, but have apertures, holes, openings, orifices, slits or pores of sufficiently small cross-dimension to hold the cell or tissue component, and to retain particulates, e.g. cell debris, in the hollow body. Each of the integers may then effectively form a macroscopic and/or microscopic filter.

Alternatively, it may contain a cell or tissue component that is bound to an insoluble and immobilised substrate over and/or through which the irrigant and/or wound exudate from the wound dressing passes, e.g. a scaffold. This will often be of a material that is not (cyto)toxic and is biocompatible and inert to any components that are beneficial in promoting wound healing, including natural and synthetic polymeric materials, which may typically in the form of a conformable film, sheet or membrane, often with apertures, holes, openings, orifices, slits or slots of small cross-dimension.

It may then effectively form a structure which is a mesh, grid, lattice, net or web. The container for cells or tissue may then not need to comprise two or more integers which are permeable to the wound exudate or a mixture with irrigant to hold the cell or tissue component in the hollow body, but they may be desirable to retain particulates, e.g. cell debris. The container that contains the tissue or cell component will normally be mounted within or in association with a device constructed to maintain the viability and activity of the cells. This would include but not be limited to the means for supplying nutrition and regulating the exchange of gases and maintaining an optimum temperature.

The means for supplying nutrition may comprise a conventional nutrient medium for the cells or tissue containing one or more physiologically active component materials that are beneficial in promoting cell proliferation in the cells or tissue in the container that contains the cells or tissue and/or the expression by such cells or tissue of one or more physiologically active component materials that are beneficial in promoting wound healing.

Simultaneous Aspiration and Irrigation

The means for providing simultaneous aspiration and irrigation of the wound often comprises (a) a (first) device for moving fluid through the wound applied to fluid downstream of and away from the wound dressing, in combination with at least one of (b) a second device for moving fluid through the wound applied to the irrigant in the fluid supply tube upstream of and towards the wound dressing; (c) means for aspirate flow regulation, connected to a fluid offtake tube, and (d) means for supply flow regulation, connected to a fluid supply tube.

The (first) device is applied to the fluid in the fluid tube and/or the fluid in the fluid offtake tube downstream of and away from the wound dressing, and will usually apply negative pressure (i.e. below-atmospheric pressure or vacuum) to the wound bed. The (first) device will apply negative pressure (i.e. below-atmospheric pressure or vacuum) to the wound bed. It may be applied to the aspirate in the fluid offtake tube downstream of and away from the wound dressing. It may have means for aspirate flow regulation, such as a regulator, such as a rotary valve connected between two parts of a fluid offtake tube, such that the desired supply flow regulation is achieved.

Alternatively or additionally, where appropriate, the aspirate in the fluid offtake tube downstream of the wound dressing may be aspirated into a collection vessel, and the first device may act on fluid such as air from the collection vessel. This prevents contact of the device with the aspirate.

The (first) device may be a fixed-throughput device, such as a fixed-speed pump, which will usually require a discrete means for aspirate flow regulation, connected to a fluid offtake tube, and/or means for supply flow regulation, connected to a fluid supply tube, in each case, e.g. a regulator, such as a rotary valve.

Alternatively, where appropriate the (first) device for moving fluid through the wound may be a variable-throughput device, such as a variable-speed pump, downstream of the wound dressing, thus effectively forming a combination of a (first) device for moving fluid through the wound with means for aspirate flow regulation and/or means for supply flow regulation in a single integer.

The (first) device for moving fluid through the wound will often be a pump of any of the following types, or a piped supply of vacuum, applied to fluid downstream of and away from the wound dressing. In the case of any pump it may be a fixed-speed pump, with (as above) a discrete means for aspirate flow regulation, connected to a fluid offtake tube, and/or means for supply flow regulation, connected to a fluid supply tube, in each case, e.g. a regulator, such as a rotary valve. Alternatively, where appropriate the pump may be a variable-throughput or variable-speed pump.

The following types of pump may be used as the (first) device: (a) reciprocating pumps, such as (i) Piston pumps—where pistons pump fluids through check valves, in particular for positive and/or negative pressure on the wound bed; and (ii) Diaphragm pumps—where pulsations of one or two flexible diaphragms displace liquid with check valves; and (b) Rotary pumps, such as: (i) Progressing cavity pumps with a cooperating screw rotor and stator, in particular for higher-viscosity and particulate-filled exudate; and (ii) Vacuum pumps—with pressure regulators.

The (first) device may be a diaphragm pump, e.g. preferably a small portable diaphragm pump. This is a preferred type of pump, in order in particular to reduce or eliminate contact of internal surfaces and moving parts of the pump with (chronic) wound exudate, and for ease of cleaning.

Where the pump is a diaphragm pump, and preferably a small portable diaphragm pump, the one or two flexible diaphragms that displace liquid may each be, for example a polymer film, sheet or membrane, that is connected to means for creating the pulsations. This may be provided in any form that is convenient, inter alia as a piezoelectric transducer, a core of a solenoid or a ferromagnetic integer and coil in which the direction of current flow alternates, a rotary cam and follower, and so on.

Where any second device is applied to the fluid in the fluid supply tube upstream of and towards the wound dressing, it will usually apply positive pressure (i.e. above-atmospheric pressure) to the wound bed. As with the (first) device, it may be a fixed-throughput device, such as a fixed-speed pump, which will usually require a discrete means for supply flow regulation, connected to a fluid supply tube, e.g. a regulator, such as a rotary valve.

Alternatively, where appropriate the second device for moving irrigant fluid to the wound may be a variable-throughput device, such as a variable-speed pump, upstream of the wound dressing, thus effectively forming a combination of a second device for moving fluid through the wound with means for supply flow regulation in a single integer.

The second device for moving fluid through the wound will often be a pump of any of the following types applied to the irrigant in the fluid supply tube upstream of and towards the wound dressing. It may be a fixed-speed pump, with (as above) a discrete means for supply flow regulation, connected to a fluid supply tube, e.g. a regulator, such as a rotary valve. Alternatively, where appropriate the pump may be a variable-throughput or variable-speed pump. It may have means for aspirate flow regulation, such as a regulator, such as a rotary valve connected between two parts of a fluid offtake tube, such that the desired supply flow regulation is achieved.

The following types of pump may be used as the second device: (a) Reciprocating pumps, such as (i) Shuttle pumps—with an oscillating shuttle mechanism to move fluids at rates from 2 to 50 ml per minute; and (b) Rotary pumps, such as: (i) Centrifugal pumps, (ii) Flexible impeller pumps—where elastomeric impeller traps fluid between impeller blades and a moulded housing that sweeps fluid through the pump housing, (iii) Peristaltic pumps—with peripheral rollers on rotor arms acting on a flexible fluid aspiration tube to urge fluid current flow in the tube in the direction of the rotor, (iv) Rotary vane pumps—with rotating vaned disk attached to a drive shaft moving fluid without pulsation as it spins. The outlet can be restricted without damaging the pump.

The second device may be a peristaltic pump, e.g. preferably a small portable peristaltic pump. This is a preferred type of pump, in order in particular to reduce or eliminate contact of internal surfaces and moving parts of the pump with irrigant, and for ease of cleaning. Where the pump is a peristaltic pump, this may be e.g. an Instech Model P720 miniature peristaltic pump, with a flow rate: of 0.2-180 ml/hr and a weight of <0.5 k. This is potentially useful for home and field hospital use.

Each such pump of any these types may also suitably be one that is capable of pulsed, continuous, variable and/or automated and/or programmable fluid movement. Less usually and less preferably, each such pump of any these types will be reversible.

As above, the means for supply flow regulation may be a regulator, such as a rotary valve. This is connected between two parts of a fluid supply tube, such that the desired supply flow regulation is achieved. If there are two or more inlet pipes, these may be connected to a single fluid supply tube with a single regulator, or to first, second, etc. fluid supply tubes, respectively having a first regulator, a second regulator, etc., e.g. a valve or other control device for admitting fluids into the wound.

As above, the means for aspirate flow regulation may be similarly provided in a form in which concomitant aspirate flow regulation is possible. It may be a regulator, such as a valve or other control device, e.g. a rotary valve. Multiple offtake tubes may be similarly provided with single or multiple regulators for aspiration of fluids from the apparatus, e.g. to an aspirate collection vessel, such as a collection bag. If there is no second device for moving fluid through the wound applied to the irrigant in the fluid supply tube upstream of and towards the wound dressing, it is only possible to apply a negative pressure to the wound, by means of the device for moving fluid through the wound applied to the aspirate in the fluid offtake tube downstream of and away from the wound dressing.

Operation may e.g. be carried out at a negative pressure of up to 50% atm., typically at a low negative pressure of up to 20% atm., more usually up to 10% atm. at the wound, as is described hereinafter.

Examples of suitable and preferred (first) devices include those types of pump that are so described hereinbefore in relation to the first device. This may be a diaphragm pump, e.g. preferably a small portable diaphragm pump. This is a preferred type of pump, in order in particular to reduce or eliminate contact of internal surfaces and moving parts of the pump with (chronic) wound exudate, and for ease of cleaning.

Alternatively, if it is desired to apply a net positive pressure to the wound, the means for providing simultaneous aspiration and irrigation of the wound should comprise not only (a) a first device for moving fluid through the wound applied to the aspirate in the fluid offtake tube downstream of and away from the wound dressing, but also (b) a second device for moving fluid through the wound applied to the irrigant in the fluid supply tube upstream of and towards the wound dressing.

Operation may then e.g. be carried out at a positive pressure of up to 50% atm., typically at a low positive pressure of up to 20% atm., more usually up to 10% atm. at the wound, as is described hereinafter.

Examples of suitable and preferred first devices include those types of pump that are so described hereinbefore in relation to the first device. This may be a diaphragm pump, e.g. preferably a small portable diaphragm pump. This is a preferred type of pump, in order in particular to reduce or eliminate contact of internal surfaces and moving parts of the pump with (chronic) wound exudate, and for ease of cleaning.

Examples of suitable and preferred second devices include those types of pump that are so described hereinbefore in relation to the second device. This may be a peristaltic pump, e.g. a miniature peristaltic pump. This is a preferred type of pump, in order to eliminate contact of internal surfaces and moving parts of the pump with irrigant in the fluid supply tube upstream of and towards the wound dressing, and for ease of cleaning.

It is of course equally possible to apply a negative pressure to the wound, by means of such a combination of (a) a first device for moving fluid through the wound applied to the aspirate in the fluid offtake tube downstream of and away from the wound dressing, and (b) a second device for moving fluid through the wound applied to the irrigant in the fluid supply tube upstream of and towards the wound dressing; optionally with (c) means for supply flow regulation, connected to a fluid supply tube; (d) means for aspirate flow regulation, connected to a fluid offtake tube.

Indeed, as noted below in this regard, preferred embodiments of the apparatus for aspirating, irrigating and/or cleansing chronic wounds that apply a negative pressure include such types of combination of (a) a first device, e.g. a diaphragm pump, e.g. preferably a small portable diaphragm pump, and (b) a second device, e.g. a peristaltic pump, preferably a miniature peristaltic pump, as described hereinbefore in relation to the device for moving fluid through the wound.

As noted above, either of the first device and the second device may be (a) a fixed-throughput device, such as a fixed-speed pump, which will usually require a discrete means for aspirate flow regulation, connected to a fluid offtake tube, and/or means for supply flow regulation, connected to a fluid supply tube, in each case, e.g. a regulator, such as a rotary valve, or (b) a variable-throughput device, such as a variable-speed pump, downstream of the wound dressing, thus effectively forming a combination of a (first) device for moving fluid through the wound with means for aspirate flow regulation and/or means for supply flow regulation in a single integer.

The higher end of the ranges of % positive and negative pressure and/or vacua noted above are potentially more suitable for hospital use, where they may only be used safely under professional supervision. The lower end is potentially more suitable for home use, where relatively high % positive and negative pressures and/or vacua cannot be used safely without professional supervision, or for field hospital use. In each case, the pressure on the wound may be held constant throughout the desired length of therapy, or may be varied cyclically in a desired positive or negative pressure regime.

As noted above, when it is desired to apply a negative pressure to the wound, it is preferred that the means for providing simultaneous aspiration and irrigation of the wound comprise not only (a) a (first) device for moving fluid through the wound applied to the aspirate in the fluid offtake tube downstream of and away from the wound dressing, but also (b) a second device for moving fluid through the wound applied to the irrigant in the fluid supply tube upstream of and towards the wound dressing.

Accordingly, one embodiment of the apparatus for irrigating, cleansing and/or aspirating wounds of the present invention is characterised in the means for providing simultaneous aspiration and irrigation of the wound comprises (a) a (first) device for moving fluid through the wound applied to fluid downstream of and away from the wound dressing, and (b) a second device for moving fluid through the wound applied to the irrigant in the fluid supply tube upstream of and towards the wound dressing, and in combination with at least one of (c) means for supply flow regulation, connected to a fluid supply tube, and (d) means for aspirate flow regulation, connected to a fluid offtake tube.

As noted above, either of the first device and the second device may be (a) a fixed-throughput device, such as a fixed-speed pump, which will usually require a discrete means for aspirate flow regulation, connected to a fluid offtake tube, and/or means for supply flow regulation, connected to a fluid supply tube, in each case, e.g. a regulator, such as a rotary valve, or (b) a variable-throughput device, such as a variable-speed pump, downstream of the wound dressing, thus effectively forming a combination of a (first) device for moving fluid through the wound with means for aspirate flow regulation and/or means for supply flow regulation in a single integer.

This combination of (a) a device for moving fluid through the wound applied to the aspirate in the fluid offtake tube downstream of and away from the wound dressing, and (b) a device for moving fluid through the wound applied to the fluid in the fluid supply tube upstream of and towards the wound dressing, may be used to apply an overall positive or negative, or even zero pressure to the wound.

At least one body in the flow path to, over and from the wound bed should have sufficient resilience against the pressure to allow any significant compression or decompression of the fluid occur. Thus, examples of suitable bodies include those which are or are defined by a film, sheet or membrane, such as inlet or offtake and/or tubes and structures such as bags, chambers and pouches, filled with irrigant fluid, and e.g. the backing layer of the wound dressing, made of elastically resilient thermoplastic materials.

It will be seen that the balance of fluid between aspirated fluid from the wound and irrigant supplied to the wound from the fluid reservoir will thus be largely determined by a means for providing simultaneous aspiration and irrigation of the wound which is a system comprising: (a) means for aspirate flow regulation and/or a device for moving fluid through the wound applied to fluid downstream of and away from the wound dressing, and (b) means for supply flow regulation and/or a device for moving fluid through the wound applied to the fluid in the fluid supply tube upstream of and towards the wound dressing.

As noted above, either of the first device and the second device may be (a) a fixed-throughput device, such as a fixed-speed pump, which will usually require a discrete means for aspirate flow regulation, connected to a fluid offtake tube, and/or means for supply flow regulation, connected to a fluid supply tube, in each case, e.g. a regulator, such as a rotary valve, or (b) a variable-throughput device, such as a variable-speed pump, downstream of the wound dressing, thus effectively forming a combination of a (first) device for moving fluid through the wound with means for aspirate flow regulation and/or means for supply flow regulation in a single integer.

At least one body in the flow path to, over and from the wound bed should have sufficient resilience against the pressure to allow any significant compression or decompression of the fluid occur. Thus, examples of suitable bodies include those which are or are defined by a film, sheet or membrane, such as inlet or offtake and/or tubes and structures such as bags, chambers and pouches, filled with irrigant fluid, and e.g. the backing layer of the wound dressing, made of elastically resilient thermoplastic materials.

It will be seen that the balance of fluid between aspirated fluid from the wound and irrigant supplied to the wound from the fluid reservoir will thus be largely determined by a means for providing simultaneous aspiration and irrigation of the wound which may be a system comprising: (a) means for aspirate flow regulation and/or a device for moving fluid through the wound applied to fluid downstream of and away from the wound dressing, and (b) means for supply flow regulation and/or a device for moving fluid through the wound applied to the fluid in the fluid supply tube upstream of and towards the wound dressing.

The same means may be used to apply an overall positive or negative, or even neutral pressure to the wound. The means may also be used to vary the pressure in the wound dressing (e.g. via a manifold) to apply stress to the wound bed and optionally areas surrounding the wound.

The appropriate flow rate through the supply tube will depend on a number of factors, such as (a) The components of the irrigant and/or wound exudate, the relative volumes of irrigant and wound exudate, (b) the viscosity and consistency of each of the irrigant, exudate and mixed exudate-irrigant fluid, and any changes as the wound heals; (c) the level of negative pressure on the wound bed, (d) whether the irrigant in the fluid supply tube upstream of and into the wound dressing is under positive pressure, and the level of such pressure; (e) the level of any pressure drop between the irrigant in the fluid supply tube upstream of the wound dressing and the wound bed, such as across a porous element, e.g. a membrane scaffold on the lower surface of an inlet manifold that delivers the fluid directly to the wound bed; means for supply flow regulation; and/or a second device for moving fluid through the wound applied to the fluid in the fluid supply tube upstream of and towards the wound dressing; (f) the depth and/or capacity of the wound and (g) the power consumption needed for a given desired fluid volume flow rate of irrigant and/or wound exudate through the wound.

It may also depend on the level of any pressure drop between the irrigant in the fluid supply tube upstream of the wound dressing and the wound bed, such as across a porous element, e.g. a membrane scaffold on the lower surface of an inlet manifold that delivers the fluid directly to the wound bed; means for supply flow regulation; and/or a second device for moving fluid through the wound applied to the fluid in the fluid supply tube upstream of and towards the wound dressing;

The dressing may comprise an inlet manifold (as described in further detail hereinafter) that covers and contacts a significant area, preferably most of the wound bed with openings that deliver the fluid directly to the wound bed over an extended area, in the form of one or more inflatable hollow bodies defined by a film sheet or membrane. In general a manifold will cover 50% of the wound, preferably 75% or more, though it is possible that it may cover a smaller area of the wound. The (usually small) positive pressure above atmospheric from the irrigation device when both devices are running together should be sufficient to inflate the manifold.

The desired fluid volume flow rate of irrigant and/or wound exudate is preferably that for optimum performance of the wound healing process. The flow rate will usually be in the range of 1 to 1500 ml/hr, such as 5 to 1000 ml/hr, e.g. 15 to 300 ml/hr, such as 35 to 200 ml/hr through the supply tube. The flow rate through the wound may be held constant throughout the desired length of therapy, or may be varied cyclically in a desired flow rate regime.

In practice, the offtake rate of flow of total irrigant and/or wound exudate will generally be of the order of 1 to 2000, e.g. 35 to 300 ml/24 hr/cm$^2$, where the cm$^2$ refers to the wound area, depending on whether the wound is in a highly exuding state.

In practice, the rate of exudate flow is typically only of the order of up to 75 microlitres/cm$^2$/hr (where cm$^2$ refers to the wound area), and the fluid can be highly mobile or not, depending on the level of proteases present). Exudate levels drop and consistency changes as the wound heals, e.g. to a level for the same wound that equates to 12.5-25 microlitres/cm$^2$/hr.

It will be seen that the aspirated fluid from the wound will typically contain a preponderance of irrigant from the fluid reservoir over wound exudate. The necessary adjustments to maintain the desired balance of fluid by means of (a) the means for aspirate flow regulation and/or downstream device, and (b) the means for supply flow regulation and/or upstream device for moving fluid will be apparent to the skilled person, bearing in mind that as noted above, either of the first device and the second device may be (i) a fixed-throughput device, such as a fixed-speed pump, which will usually require a discrete means for aspirate flow regulation, connected to a fluid offtake tube, and/or means for supply flow regulation, connected to a fluid supply tube, in each case, e.g. a regulator, such as a rotary valve, or (ii) a variable-throughput device, such as a variable-speed pump, downstream of the wound dressing, thus effectively forming a combination of a (first) device for moving fluid through the wound with means for aspirate flow regulation and/or means for supply flow regulation in a single integer.

The type and/or capacity of a suitable first device for moving fluid through the wound applied to the aspirate in the fluid offtake tube downstream of and away from the wound dressing and/or a suitable second device for moving fluid through the wound applied to the irrigant in the fluid supply tube upstream of and towards the wound dressing and/or will be largely determined by (a) the appropriate or desired fluid volume flow rate of irrigant and/or wound exudate from the wound, and (b) whether it is appropriate or desired to apply a positive or negative pressure to the wound bed, and the level of such pressure to the wound bed for optimum performance of the wound healing process, and by factors such as portability, power consumption and isolation from contamination.

As noted above, when it is desired to apply a negative pressure to the wound with the apparatus for aspirating, irrigating and/or cleansing wounds to provide simultaneous aspiration and irrigation of the wound, the means for providing simultaneous aspiration and irrigation of the wound may comprise (a) a single device for moving fluid through the wound applied to the aspirate in the fluid offtake tube downstream of and away from the wound dressing or in combination with at least one of (b) means for supply flow regulation, connected to a fluid supply tube, and (c) means for aspirate flow regulation, connected to a fluid offtake tube.

As noted above, the device may be (a) a fixed-throughput device, such as a fixed-speed pump, which will usually require a discrete means for aspirate flow regulation, connected to a fluid offtake tube, e.g. a regulator, such as a rotary valve, or (b) a variable-throughput device, such as a variable-speed pump, downstream of the wound dressing, thus effectively forming a combination of a device for moving fluid through the wound with means for aspirate flow regulation in a single integer.

In a preferred embodiment the apparatus has at least one inlet pipe and at least one outlet pipe, each of which passes through and/or under the wound-facing face. Such an embodiment allows for a method simultaneous and/or sequential irrigation/aspiration of the wound. In such an embodiment step (d) of the method comprises activating the at least one device of moving fluid through the wound dressing to move fluid (irrigant) through the at least one inlet and to move fluid (aspirate) out of the at least one outlet pipe.

In a preferred embodiment the irrigant is moved to the wound via the inlet pipe and aspirate removed from the outlet pipe simultaneously, i.e. simultaneous irrigation/aspiration. This may be carried out for substantially the entirety of the treatment of the wound, or alternately for portions of the treatment as desired.

Such an embodiment is also suitable for sequential (fill/empty) operation, and thus a method wherein sequential operation is carried out forms an alternative embodiment of the invention. In such an embodiment irrigation would be ceased by ceasing the device moving fluid through the at least one inlet and activating a device to move fluid from the wound through the outlet.

Suitable flow rates, parameters for operation of the means for applying stress and for operation of the apparatus in general are set out above. Further details are given below.

Conformable Wound Dressing

In certain embodiments of the apparatus for aspirating, irrigating, and/or cleansing wounds, a particular advantage is the tendency of the wound dressing to conform to the shape of the bodily part to which it is applied.

The wound dressing comprises (a) a backing layer with a wound-facing face which is capable of forming a relatively fluid-tight seal or closure over a wound and (b) at least one inlet pipe for connection to a fluid supply tube or tube, which passes through and/or under the wound-facing face, and (c) at least one outlet pipe for connection to a fluid offtake tube, which passes through and/or under the wound-facing face, the point at which the or each inlet pipe and the or each outlet pipe passes through and/or under the wound-facing face forming a relatively fluid-tight seal or closure.

The term 'relatively fluid-tight seal or closure' is used herein to indicate one which is fluid- and microbe-impermeable and permits a positive or negative pressure of up to 50% atm., more usually up to 20% atm., e.g. up to 10% atm. to be applied to the wound. The term 'fluid' is used herein to include gels, e.g. thick exudate, liquids, e.g. water, and gases, such as air, nitrogen, etc.

The shape of the backing layer that is applied may be any that is appropriate to aspirating, irrigating, and/or cleansing the wound across the area of the wound. Examples of such include a substantially flat film, sheet or membrane, or a bag, chamber, pouch or other structure of the backing layer, e.g. of polymer film, which can contain the fluid.

The backing layer may be a film, sheet or membrane, often with a (generally uniform) thickness of up to 100 micron, preferably up to 50 micron, more preferably up to 25 micron, and of 10 micron minimum thickness.

Its largest cross-dimension may be up to 500 mm (for example for large torso wounds), up to 100 mm (for example for axillary and inguinal wounds), and up to 200 mm for limb wounds (for example for chronic wounds, such as venous leg ulcers and diabetic foot ulcers.

Desirably the dressing is resiliently deformable, since this may result in increased patient comfort, and lessen the risk of inflammation of a wound. Suitable materials for it include synthetic polymeric materials that do not absorb aqueous fluids, such as polyolefins, such as polyethylene e.g. high-density polyethylene, polypropylene, copolymers thereof, for example with vinyl acetate and polyvinyl alcohol, and mixtures thereof; polysiloxanes; polyesters, such as polycarbonates; polyamides, e.g. 6-6 and 6-10, and hydrophobic polyurethanes. They may be hydrophilic, and thus also include hydrophilic polyurethanes. They also include thermoplastic elastomers and elastomer blends, for example copolymers, such as ethyl vinyl acetate, optionally or as necessary blended with high-impact polystyrene. They further include elastomeric polyurethane, particularly polyurethane formed by solution casting. Preferred materials for the present wound dressing include thermoplastic elastomers and curable systems.

The backing layer is capable of forming a relatively fluid-tight seal or closure over the wound and/or around the inlet and outlet pipe(s). The backing layer may be impermeable, semi-impermeable or otherwise.

However, in particular around the periphery of the wound dressing, outside the relatively fluid-tight seal, it is preferably of a material that has a high moisture vapour permeability, to prevent maceration of the skin around the wound. It may also be a switchable material that has a higher moisture vapour permeability when in contact with liquids, e.g. water, blood or wound exudate. This may, e.g. be a material that is used in Smith & Nephew's Allevyn™, IV3000™ and OpSite™ dressings.

The periphery of the wound-facing face of the backing layer may bear an adhesive film, for example, to attach it to the skin around the wound. This may, e.g. be a pressure-sensitive adhesive, if that is sufficient to hold the wound dressing in place in a fluid-tight seal around the periphery of the wound-facing face of the wound dressing.

Alternatively or additionally, where appropriate a light switchable adhesive could be used to secure the dressing in place to prevent leakage. (A light switchable adhesive is one the adhesion of which is reduced by photocuring. Its use can be beneficial in reducing the trauma of removal of the dressing.) Thus, the backing layer may have a flange or lip extending around the proximal face of the backing layer, of a transparent or translucent material (for which it will be understood that materials that are listed above are amongst those that are suitable). This bears a film of a light switchable adhesive to secure the dressing in place to prevent leakage on its proximal face, and a layer of opaque material on its distal face.

To remove the dressing and not cause excessive trauma in removal of the dressing, the layer of opaque material on the distal face of the flange or lip extending around the proximal wound is removed prior to application of radiation of an appropriate wavelength to the flange or lip.

If the periphery of the wound dressing, outside the relatively fluid-tight seal, that bears an adhesive film to attach it to the skin around the wound, may be of a material that has a high moisture vapour permeability or is a switchable material, then the adhesive film, if continuous, should also have a high or switchable moisture vapour permeability, e.g. be an adhesive such as used in Smith & Nephew's Allevyn™, IV3000™ and OpSite™ dressings.

Where a vacuum is applied to hold the wound dressing in place in a fluid-tight seal around the periphery of the wound-facing face of the wound dressing, the wound dressing may be provided with a silicone flange or lip to seal the dressing around the wound. This removes the need for adhesives and associated trauma to the patient's skin.

Where the interior of, and the flow of irrigant and/or wound exudate to and through, the dressing is under any significant positive pressure, which will tend to act at peripheral points to lift and remove the dressing off the skin around the wound. In such use of the apparatus, it may thus be necessary to provide means for forming and maintaining such a seal or closure over the wound against such positive pressure on the wound, to act at peripheral points for this purpose. Examples of such means include light switchable adhesives, as above, to secure the dressing in place to prevent leakage.

Since the adhesion of a light switchable adhesive is reduced by photocuring, thereby reducing the trauma of removal of the dressing, a film of a more aggressive adhesive may be used, e.g. on a flange, as above. Examples of suitable fluid adhesives for use in more extreme conditions where trauma to the patient's skin is tolerable include ones that consist essentially of cyanoacrylate and like tissue adhesives, applied around the edges of the wound and/or the proximal face of the backing layer of the wound dressing, e.g. on a flange or lip.

Further suitable examples of such securing means include adhesive (e.g. with pressure-sensitive adhesive) and non-adhesive, and elastic and non-elastic straps, bands, loops, strips, ties, bandages, e.g. compression bandages, sheets, covers, sleeves, jackets, sheaths, wraps, stockings and hose, e.g. elastic tubular hose or elastic tubular stockings that are a compressive fit over a limb wound to apply suitable pressure to it when the therapy is applied in this way; and inflatable cuffs, sleeves, jackets, trousers, sheaths, wraps, stockings and hose that are a compressive fit over a limb wound to apply suitable pressure to it when the therapy is applied in this way.

Such securing means may each be laid out over the wound dressing to extend beyond the periphery of the backing layer of the wound dressing, and as appropriate will be adhered or otherwise secured to the skin around the wound and/or itself and as appropriate will apply compression (e.g. with elastic bandages, stockings) to a degree that is sufficient to hold the wound dressing in place in a fluid-tight seal around the periphery of the wound, Such securing means may each be integral with the other components of the dressing, in particular the backing layer.

Alternatively, it may be permanently attached or releasably attached to the dressing, in particular the backing layer, with an adhesive film, for example, or these components may be a Velcro™, push snap or twist-lock fit with each other.

The securing means and the dressing may be separate structures, permanently unattached to each other.

In a more suitable layout for higher positive pressures on the wound, a stiff flange or lip extends around the periphery of the proximal face of the backing layer of the wound dressing as hereinbefore defined.

The flange or lip is concave on its proximal face to define a peripheral channel or conduit. It has a suction outlet that passes through the flange or lip to communicate with the channel or conduit and may be connected to a device for applying a vacuum, such as a pump or a piped supply of vacuum. The backing layer may be integral with or attached, for example by heat-sealing, to the flange or lip extending around its proximal face.

To form the relatively fluid-tight seal or closure over a wound that is needed and to prevent passage of irrigant and/or exudate under the periphery of the wound-facing face of the wound dressing, in use of the apparatus, the dressing is set on the skin around the wound.

The device then applies a vacuum to the interior of the flange or lip, thus forming and maintaining a seal or closure acting at peripheral points around the wound against the positive pressure on the wound.

With the foregoing means of attachment, and means for forming and maintaining a seal or closure over the wound, against positive or negative pressure on the wound at peripheral points around the wound, the wound dressing sealing periphery is preferably of a generally round shape, such as an ellipse, and in particular circular.

In certain embodiments there is provided a conformable wound dressing, characterised in one embodiment in that it comprises a backing layer with a wound-facing face which is capable of forming a relatively fluid-tight seal or closure over a wound and has (a) at least one inlet pipe for connection to a fluid supply tube, which passes through and/or under the wound-facing face, and (b) at least one outlet pipe for connection to a fluid offtake tube, which passes through and/or under the wound-facing face, (c) the point at which the or each inlet pipe and the or each outlet pipe passes through and/or under the wound-facing face forming a relatively fluid-tight seal or closure over the wound.

The dressing is advantageously provided for use in a bacteria-proof pouch.

The conformable wound dressing may be used for aspirating, irrigating and/or cleansing wounds in conjunction with a biodegradable scaffold, which permits fluid supply towards the wound bed from the wound dressing.

The dressings depicted and described in WO 03/004647 may be used in the apparatus of certain embodiments of the present invention with means for supplying thermal energy to the fluid in the wound, e.g. a conductive heater, acting on the irrigant liquid in the flowpath upstream of the wound dressing, e.g. in the fluid supply tube from the irrigant fluid reservoir, usually as close to the wound dressing backing layer as possible.

Embodiments of the present invention may also include: (a) a suction head having a first face; (b) a second face opposite said first face, wherein said second face is comprised of a plurality of projections, said projections defining a plurality of channels for facilitating flow of fluids to an opening in said second face and through said first face, wherein said opening is adapted for connection to a suction tube; and (c) a surgical drape having an aperture coincident said opening, said surgical drape extending over a region, and overlapping beyond the perimeter of said first face, and wherein said surgical drape comprises a flexible adhesive coated film adhered to said region of said first face and a release-coated backing extending over said second face and adhered to the overlapping portion of said surgical drape.

For distributing fluid across a wound surface, particular embodiments of the present invention may also include: (a) a suction head having a first face; (b) a second face opposite said first face; (c) a plurality of projections coincident from said second face, wherein said projections form a contact surface with the wound surface, and wherein a plurality of channels for facilitating flow of fluids are defined between said projections, said channels remaining out of contact with the wound surface; and (d) an aperture in fluid communication with said channels formed by said projections and formed through said first face and second face.

Embodiments of the present invention may also comprise: a method of using a therapeutic apparatus for stimulating the healing of wounds in mammals comprising the steps of: (a) inserting a porous pad into or on said wound such that said porous pad is in contact with said wound, wherein said porous pad has at least a partial outer surface and an inner body, said outer surface being adapted for contact with surface of said wound with small first pores no larger than about 100 microns in diameter to enhance biocompatibility; (b) securing said porous paid within said wound with the dressing cover to maintain a negative pressure at the site of said wound; (c) generating a negative pressure at said wound through said porous pad; and (d) collecting fluids from said wound through said porous pad.

Wound Filler

As also mentioned herein, the backing layer that is applied may be any that is appropriate to the present system of therapy and permits a positive or negative pressure of up to 50% atm., more usually up to 25% atm. to be applied to the wound.

It is thus often a microbe-impermeable film, sheet or membrane, which is substantially flat, depending on any pressure differential on it, and often with a (generally uniform) thickness similar to such films or sheets used in conventional wound dressings, i.e. up to 100 micron, preferably up to 50 micron, more preferably up to 25 micron, and of 10 micron minimum thickness.

The backing layer may often have a rigid and/or resiliently inflexible or stiff area to resist any substantial play between other components that are not mutually integral, and may be stiffened, reinforced or otherwise strengthened, e.g. by a projecting boss.

Such a form of dressing would not be very conformable to the scaffold and/or wound bed, and may effectively form a chamber, hollow or cavity defined by a backing layer and the scaffold and/or wound bed under the backing layer.

It may be desirable that the interior of the wound dressing conform to the scaffold and/or wound bed, even for a wound in a highly exuding state. Accordingly, one form of the dressing is provided with a wound filler under the backing layer. This is favourably a resiliently flexible, e.g. elastomeric, and preferably soft, structure with good conformability to wound shape. It is urged by its own resilience against the backing layer to apply gentle pressure on the scaffold and wound bed.

The wound filler may be integral with the other components of the dressing, in particular the backing layer. Alternatively, it may be permanently attached to them/it, with an adhesive film, for example, or by heat-sealing, e.g. to a flange or lip extending from the proximal face, so a not to disrupt the relatively fluid-tight seal or closure over the wound that is needed.

Less usually, the wound filler is releasably attached to the backing layer, with an adhesive film, for example, or these components may be a push, snap or twist-lock fit with each other. The wound filler and the backing layer may be separate structures, permanently unattached to each other.

The wound filler may be or comprise a solid integer, favourably a resiliently flexible, e.g. elastomeric, and preferably soft, structure with good conformability to wound shape. Examples of suitable forms of such wound fillers are foams formed of a suitable material, e.g. a resilient thermoplastic. Preferred materials for the fillers, or present wound dressing, include reticulated filtration polyurethane foams with small apertures or pores. Alternatively or additionally, it may be in the form of, or comprise one or more conformable hollow bodies defined by a film, sheet or membrane, such as a bag, chamber, pouch or other structure, filled with a fluid or solid that urges it to the wound shape.

The film, sheet or membrane, often has a (generally uniform) thickness similar to that of films or sheets used in conventional wound dressing backing layers. That is, up to 100 micron, preferably up to 50 micron, more preferably up to 25 micron, and of 10 micron minimum thickness, and is often resiliently flexible, e.g. elastomeric, and preferably soft. Such a filler is often integral with the other components of the dressing, in particular the backing layer, or permanently attached to them/it, with an adhesive film, for example, or by heat-sealing, e.g. to a flange Examples of suitable fluids contained in the hollow body or bodies defined by a film, sheet or membrane include gases, such as air, nitrogen and argon, more usually air, at a small positive pressure above atmospheric; and liquids, such as water, saline. Examples also include gels, such as silicone gels, e.g. CaviCare™ gel, or preferably cellulosic gels, for example hydrophilic cross-linked cellulosic gels, such as Intrasite™ cross-linked materials. Examples also include aerosol foams, where the gaseous phase of the aerosol system is air or an inert gas, such as nitrogen or argon, more usually air, at a small positive pressure above atmospheric; and solid particulates, such as plastics crumbs.

In an alternative embodiment the filler of the apparatus can conveniently be an expandable or contractible module which is the means to apply stress to the wound bed. In one preferred embodiment the module comprises an inflatable body, e.g. an inflatable pouch or bag. Of course, if the backing layer is a sufficiently conformable and/or e.g. an upwardly dished sheet, the backing layer may lie under the wound filler, rather than vice versa.

In this type of layout, in order for the wound filler to urge the wound dressing towards the scaffold and wound bed, it will usually have to be firmly adhered or otherwise releasably attached to the skin around the wound. This is especially the case in those embodiments where the wound filler and the backing layer are separate structures, permanently unattached to each other.

In such a layout for deeper wounds when the therapy is applied in this way, the means for such attachment may also form and maintain a seal or closure over the wound. Where the filler is over the backing layer, and the fluid inlet pipe(s) and outlet pipe(s) pass through the wound-facing face of the backing layer, they may run through or around the wound filler over the backing layer.

One form of the dressing is provided with a wound filler under the backing layer that is or comprises a resiliently flexible, e.g. elastomeric, and preferably soft, hollow body defined by a film, sheet or membrane, such as a bag, chamber, pouch or other structure. It has apertures, holes, openings, orifices, slits or slots, or tubes, pipes, tubules or nozzles. It communicates with at least one inlet or outlet pipe through at least one aperture, hole, opening, orifice, slit or slot.

The fluid contained in the hollow body may then be the aspirating or irrigating fluid in the apparatus. The hollow body or each of the hollow bodies then effectively forms an inlet pipe or outlet pipe manifold that delivers the aspirating fluid directly to the scaffold and wound bed or collects the fluid directly from the wound respectively via the holes, openings, orifices, slits or slots, or the tubes, pipes or hoses, etc. in the film, sheet or membrane.

When the therapy is applied in this way, the type of the filler may also be largely determined by the depth and/or capacity of the wound.

Thus, for shallower wounds, examples of suitable wound fillers as a component of a wound dressing include ones that consist essentially of one or more conformable hollow bodies defining an inlet pipe and/or outlet pipe manifold that delivers the aspirating fluid directly to the scaffold and wound bed or collects the fluid directly from the wound.

A more suitable wound filler for deeper wounds when the therapy is applied in this way may be one which comprises one or more conformable hollow bodies defined by, for example a polymer film, sheet or membrane, that at least partly surround(s) a solid integer. This may provide a system with better rigidity for convenient handling.

The wound filler under the backing layer may effectively form an inlet pipe or outlet pipe manifold. If not, in order for aspiration and/or irrigation of the wound bed to occur, it is appropriate for one or more bores, channels, conduits, passages, pipes, tubes, tubules and/or spaces, etc. to run from the point at which the fluid inlet pipe(s) and outlet pipe(s) pass through and/or under the wound-facing face of the backing layer through or around the wound filler under the backing layer.

Less usually, the wound filler is an open-cell foam with pores that may form such bores, channels, conduits, passages and/or spaces through the wound filler under the backing layer.

Where the filler is or comprises one or more conformable hollow bodies defined by, for example a polymer film, sheet or membrane, it may be provided with means for admitting fluids to the scaffold and wound bed under the wound dressing.

These may be in the form of pipes, tubes, tubules or nozzles running from the point at which the fluid inlet pipe(s) and outlet pipe(s) pass through and/or under the wound-facing face of the backing layer through or around the wound filler under the backing layer.

All of the suitable layouts for shallower wounds that comprise blind-bore, perforated inlet pipe or outlet pipe manifolds that aspirate fluid in the wound when the dressing is in use, that are described hereinbefore, may be used under a wound filler under the backing layer.

In brief, suitable layouts include ones where one or both manifolds are (a) annular or toroidal (regular, e.g. elliptical or circular or irregular), optionally with blind-bore, perforated radial tubes, pipes or nozzles, branching from the annulus or torus; and/or (b) in a meandering, tortuous, winding, zigzag, serpentine or boustrophedic (i.e. in the manner of a ploughed furrow) pattern, or (c) defined by slots in and apertures through layers attached to each other in a stack.

Inlet and Outlet Pipes

The apparatus for aspirating, irrigating, and/or cleansing comprises inlet and outlet pipes, or tubes, which carry the irrigating fluid to the wound and the aspirating fluid away from the wound.

The inlet and/or outlet tubes, the fluid tube and the fluid supply tube, etc. may be of conventional type, e.g. of elliptical or circular cross-section, and may suitably have a uniform cylindrical bore, channel, conduit or passage throughout their length, and suitably the largest cross-dimension of the bore may be up to 10 mm for large torso wounds, and up to 2 mm for limb wounds.

The tube walls should be suitably thick enough to withstand any positive or negative pressure on them, in particular if the volume of irrigant and/or wound exudate from the wound in is increased by continuing addition to it of wound exudate, and/or fluid passing from a cleansing fluid through a selectively permeable integer, for example the polymer film, sheet or membrane of a two-phase system, such as an aspiration and irrigation unit. However, the prime purpose of such tubes is to convey fluid irrigant and exudate through the length of the apparatus flow path, rather than to act as pressure vessels.

The tube walls may suitably be at least 25 micron thick. The bore or any perforations, apertures, holes, openings, orifices, slits or slots along the pipes, etc. or in the hollow body or each of the hollow bodies may be of small cross-dimension. They may then effectively form a macroscopic and/or microscopic filter for particulates including cell debris and micro-organisms, whilst allowing proteins and nutrients to pass through. Such tubes, pipes or hoses, etc. through and/or around the filler, whether the latter is a solid integer and/or one or more resiliently flexible or conformable hollow bodies, are described in further detail hereinbefore in connection with the inlet pipe(s) and outlet pipe(s). The whole length of the apparatus for aspirating, irrigating, and/or cleansing wounds should be microbe-impermeable once the wound dressing is over the wound in use.

To form the relatively fluid-tight seal or closure over a wound and around the inlet pipe(s) and outlet pipe(s) at the point at which they pass through and/or under the wound-facing face, the backing layer may be integral with these other components.

The components may alternatively just be a push, snap or twist-lock fit with each other, or adhered or heat-sealed together.

The or each inlet pipe or outlet pipe may be in the form of an aperture, such as a funnel, hole, opening, orifice, luer, slot or port for connection as a female member respectively to a mating end of (a) a fluid tube and/or fluid supply tube (optionally or as necessary via means for forming a tube, pipe or hose, or nozzle, hole, opening, orifice, luer, slot or port for connection as a male member respectively to a mating end of (b) a fluid tube and/or fluid supply tube (optionally or as necessary via means for supply flow regulation) or (c) a fluid offtake tube.

Where the components are integral they will usually be made of the same material (for which it will be understood that materials that are listed above are amongst those that are suitable).

Where, alternatively, they are a push, snap or twist-lock fit, the may be of the same material or of different materials. In either case, materials that are listed above are amongst those that are suitable for all the components.

The or each pipe will generally pass through, rather than under the backing layer. In such case, the backing layer may often have a rigid and/or resiliently inflexible or stiff area to resist any substantial play between the or each pipe and the or each mating tube, or deformation under pressure in any direction.

It may often be stiffened, reinforced or otherwise strengthened by a boss projecting distally (outwardly from the wound) around each relevant tube, pipe or hose, or nozzle, hole, opening, orifice, luer, slot or port for connection to a mating end of a fluid tube and/or fluid supply tube or fluid offtake tube.

Alternatively or additionally, where appropriate the backing layer may have a stiff flange or lip extending around the proximal face of the backing layer to stiffen, reinforce or otherwise strengthen the backing layer. The wound dressing may not comprise any integer under the backing layer in the wound in use, other than the scaffold mentioned herein.

Where a simple pipe is used to supply the irrigant to the wound, this may not provide a system to distribute irrigant over a sufficient functional surface area to irrigate the wound at a practical rate to be suitable for use, in particular in chronic wound aspiration and irrigation, with relatively high concentrations of materials that are deleterious to wound healing.

It may be advantageous to provide a system where wound irrigant may be distributed more evenly, or pass in a more convoluted path under the dressing over the wound bed and/or scaffold.

Accordingly, one form of the dressing is provided with a 'tree' form of pipes, tubes or tubules that radiate from an inlet manifold to the wound bed and/or scaffold to end in apertures and deliver the aspirating fluid directly to the scaffold and wound bed via the apertures. Similarly, there is optionally an outlet manifold from which tubules radiate and run to the wound bed and/or scaffold to end in openings and collect the fluid directly from the wound bed.

The pipes, etc. may radiate regularly or irregularly through the wound in use, respectively from the inlet or outlet manifold, although regularly may be preferred. A more suitable layout for deeper wounds is one in which the pipes, etc. radiate hemispherically and concentrically, to the wound bed and/or scaffold.

For shallower wounds, examples of suitable forms of such layout of the pipes, etc. include ones in which the pipes, etc. radiate in a flattened hemiellipsoid and concentrically, to the wound bed and/or scaffold.

Other suitable forms of layout of the pipes, etc. include one which have pipes, tubes or tubules extending from the inlet pipe(s) and/or outlet pipe(s) at the point at which they pass through and/or under the wound-facing face of the backing layer to run over the wound bed and/or scaffold. These may have a blind bore with perforations, apertures, holes, openings, orifices, slits or slots along the pipes, etc.

These pipes, etc. then effectively form an inlet pipe manifold that delivers the aspirating fluid directly to the scaffold and wound bed or outlet pipe or collects the fluid directly from the wound respectively. It does so via the holes, openings, orifices, slits or slots in the tubes, pipes, tubules, etc. over most of the wound bed and/or scaffold under the backing layer.

It may be desirable that the tubes, pipes or tubules are resiliently flexible, e.g. elastomeric, and preferably soft, structures with good conformability in the wound and the interior of the wound dressing.

When the therapy is applied in this way, the layout of the tubes, pipes, tubules, etc. may depend on the depth and/or capacity of the wound. Thus, for shallower wounds, examples of suitable forms of such layout of the tubes, pipes, tubules, etc. include ones that consist essentially of one or more of the tubes, etc in a spiral.

A more suitable layout for deeper wounds when the therapy is applied in this way may be one which comprises one or more of the tubes, etc in a helix or spiral helix. Other suitable layouts for shallower wounds include one which have blind-bore, perforated inlet pipe or outlet pipe manifolds that aspirate fluid in the wound when the dressing is in use. One or both of these may be such a form, the other may be, e.g. one or more straight blind-bore, perforated radial tubes, pipes or nozzles.

A preferred form of inlet pipe (or less usually) outlet pipe manifold that delivers the aspirating fluid directly to the scaffold and wound bed or collects the fluid directly from the wound respectively is one that comprise one or more conformable hollow bodies defined by a film, sheet or membrane, such as a bag, chamber, pouch or other structure, filled with the irrigant (or less usually) aspirate from the wound, passing through perforations, apertures, holes, openings, orifices, slits or slots in the film, sheet or membrane defining the hollow body or hollow bodies.

These may be of small cross-dimension, so that they may then effectively form microperforations, microapertures or pores in a permeable integer, for example the polymer film, sheet or membrane.

This type of manifold for irrigation (more usually) provides the highest uniformity in the flow distribution of irrigant over the wound at a practical rate to be suitable for use, in particular in chronic wound aspiration and irrigation, and hence to provide a system where materials that are beneficial in promoting wound healing, from cells or tissue, such as growth factors, cell matrix components, extracellular cell matrix components and fragments thereof, and other physiologically active components of the exudate from a wound, are distributed more evenly under the dressing over the wound bed.

This type of manifold for irrigation (more usually) is also capable of acting as a wound filler, and is noted below with regard to wound fillers under the backing layer, since it is a resiliently flexible, e.g. elastomeric, and soft, structure with good conformability to wound shape.

It is urged by its own resilience against the backing layer to apply gentle pressure on the scaffold and wound bed, and is therefore also capable of acting as a wound filler. The film, sheet or membrane, often has a (generally uniform) thickness similar to that of films or sheets used in conventional wound dressing backing layers.

Another suitable layout is one in which (a) an inlet pipe and/or outlet pipe manifold that delivers the aspirating fluid directly to the scaffold and wound bed or collects the fluid directly from the wound respectively (b) via inlet and/or outlet tubes, pipes or tubules, (c) and the inlet manifold and/or outlet manifold is formed by slots in layers permanently attached to each other in a stack, and (d) the inlet and/or outlet tubes, pipes or tubules are formed by apertures through layers permanently attached to each other in a stack. (In FIG. 10*a* there is shown an exploded isometric view of such a stack, which is non-limiting.)

Sterilization, Buffering, and Anti-Deposition

It is desirable that the wound dressing and the interior of the apparatus for aspirating, irrigating, and/or cleansing wounds is sterile.

The fluid may be sterilized in the fluid reservoir and/or the rest of the system in which the fluid moves by ultraviolet, gamma or electron beam irradiation (except for the integer that contains the tissue or cell component, since this may adversely affect the viability and activity of the cells). This way, in particular reduces or eliminates contact of internal surfaces and the fluid with any sterilizing agent.

Examples of other methods of sterilization of the fluid also include e.g. the use of (a) ultrafiltration through microapertures or micropores, e.g. of 0.22 to 0.45 micron maximum cross-dimension, to be selectively impermeable to microbes; and (b) fluid antiseptics, such as solutions of chemicals, such as chlorhexidine and povidone iodine; metal ion sources, such as silver salts, e.g. silver nitrate; and hydrogen peroxide; (c) although the latter involve contact of internal surfaces and the fluid with the sterilizing agent.

It may be desirable that the interior of the wound dressing, the rest of the system in which the fluid moves, and/or the scaffold and wound bed, even for a wound in a highly exuding state, are kept sterile after the fluid is sterilized in the fluid reservoir, or that at least naturally occurring microbial growth is inhibited. Thus, materials that are potentially or actually beneficial in this respect may be added to the irrigant initially, and as desired the amount in increased by continuing addition.

Examples of such materials include antibacterial agents (some of which are listed above), and antifungal agents. Amongst those that are suitable are, for example triclosan, iodine, metronidazole, cetrimide, chlorhexidine acetate, sodium undecylenate, chlorhexidine and iodine.

Buffering agents, such as potassium dihydrogen phosphate/disodium hydrogen phosphate may be added to adjust the pH, as may local analgesics/anaesthetics, such as lidocaine/lignocaine hydrochloride, xylocaine (adrenoline, lidocaine) and/or anti-inflammatories, to reduce wound pain or inflammation or pain associated with the dressing.

In order to combat the deposition of materials in the flow path from the irrigant, a repellent coating may be used at any point or on any integer in the path in direct contact with the fluid, e.g. on the means for providing simultaneous aspiration and irrigation of the wound or any desired tube or pipe.

Examples of coating materials for surfaces over which the aspirating fluid passes include (a) anticoagulants, such as heparin, and (b) high surface tension materials, such as PTFE, and polyamides, (c) which are useful for growth factors, enzymes and other proteins and derivatives.

Thermal Energy

In certain embodiments, the apparatus further for aspirating, irrigating and/or cleansing wounds further comprises a means for supplying thermal energy to the fluid in the wound. Examples of means for supplying thermal energy to the fluid in the wound include as may be appropriate conducted thermal energy, electromagnetic radiation of an appropriate wavelength, or (less often) as convected thermal energy. In the present apparatus, heat will usually be conducted to the wound bed by the irrigant and/or wound exudate within the dressing. However, thermal energy may as appropriate be supplied to the irrigant and/or wound exudate within the dressing, and may be applied to the fluid by any suitable means, at any suitable point, often depending on particular components and/or materials that are used.

Examples of such means include: (a) direct conductive contact of the irrigant and/or wound exudate with a heater and/or conductively heated component of the apparatus flow path; (b) direct electromagnetic irradiation at an appropriate wavelength, e.g. infrared and/or near infrared from a radiative heater of the irrigant fluid and/or wound exudate; and/or (c) electromagnetic irradiation from a radiative heater of a component of the apparatus flow path that absorbs electromagnetic irradiation at an appropriate wavelength, e.g. infrared and/or near infrared and is in direct conductive contact with the irrigant and/or wound exudate.

Accordingly, one embodiment of the present apparatus for irrigating, supplying thermal energy to and cleansing wounds supplying thermal energy to and cleansing wounds is characterised in that it comprises means for providing and conducting thermal energy to the fluid in the wound.

Another embodiment of the present apparatus for irrigating, supplying thermal energy to and cleansing wounds is characterised in that it comprises means for supplying electromagnetic radiation of an appropriate wavelength to the fluid in the wound.

Another embodiment of the present apparatus for irrigating, supplying thermal energy to and cleansing wounds is characterised in that it comprises means for supplying electromagnetic radiation of an appropriate wavelength to the fluid in the wound.

The heater of the irrigant fluid and/or wound exudate and/or heated component of the apparatus flow path may be at any convenient or appropriate position or component of the apparatus flow path. Examples include a heater and/or conductively heated component of the apparatus flow path upstream of any outlet pipe(s) that pass through and/or under the wound-facing face of the backing layer of the wound dressing, (a) mounted distally of the body on, in or inside of the dressing; (b) mounted in, on, at or near one or more of the fluid inlet pipe(s); (c) mounted in, on, at or near one or more of the connectors in the tubes that form the flow path of the apparatus; and/or (d) mounted in, on, at or near the reservoir.

As noted above, the irrigant and/or wound exudate fluid in the interior of the wound dressing is beneficially maintained at a temperature that is at or near the temperature naturally occurring in the relevant bodily part and/or normothermic temperature. The desired or optimum temperature of the wound will substantially determine (a) the position along the apparatus flow path or the component of the apparatus flow path where the heater and/or conductively heated component of the apparatus flow path is mounted relative to the dressing; (b) the flow rate of irrigant fluid and/or wound exudate; (c) the temperature to which the point of supply of thermal energy to apparatus is raised; (d) the thermal insulation of the system in which the fluid moves and heat is conducted to the wound; and/or (e) the nature of the heater.

In examples of direct conductive contact of the irrigant and/or wound exudate with a heater and/or conductively heated component of the apparatus flow path, the heater may be or be connected to a heat exchanger mounted in conductive contact with irrigant and/or wound exudate at an appropriate point in the system in which the fluid moves and heat is conducted to the wound. The heat exchanger may comprise an array of thermally conductive extended surfaces, such as fins, baffles or other like structures of conductive material in a more convoluted form with a relatively large surface area and which transfer thermal energy when a temperature drop is applied over them, mounted in conductive contact with irrigant and/or wound exudate, with spaces therebetween such that wound irrigant and/or wound exudate may move through the spaces.

Alternatively, where appropriate it may be provided in the form of a like array of conductive hollow structures, such as pipes, tubes or other like structures in the apparatus flow path, through which a heat exchanger fluid moves and transfers heat from a heat source to be conducted to the wound). The array of conductive hollow structures may consist essentially of small apertures or pores that may form such bores, channels, conduits and/or passages through a heated metal sinter, such as one of e.g. stainless steel. This is mounted in conductive contact with irrigant and/or wound exudate in the apparatus flow path, through which the fluid moves, so that heat is conducted to the wound. Such a heat exchanger may be outside the wound space and the backing layer or within the wound space and under the backing layer. If it is outside the wound space and the backing layer, it is preferably as close to the wound dressing backing layer as possible.

Examples of conductive heaters include:

(a) an electric heater mounted in conductive contact with irrigant and/or wound exudate (but electrically insulated from the fluid and the system in which the fluid moves and heat is conducted to the wound). The heater may inter alia comprise:

(i) an array of electrically resistive but conductive wires, fibres, filaments, strands or other like structures that generate thermal energy when a voltage drop is applied over them. The array may be a parallel array with spaces therebetween, and the wound irrigant and/or wound exudate may move through the spaces. Alternatively, where appropriate it may be provided in the form of non-woven or woven fabric, such as a woven layer or sheet. This may as appropriate be used essentially as a flat sheet or membrane of material in a more convoluted form, e.g. conformed to the form of other structures such as pipes, tubes, etc. in the apparatus flow path, as a duct, sheath, or casing, or other like structure. Depending on any pressure differential across it may require other materials on or in it to stiffen, reinforce or otherwise strengthen it. The material of the heater may have a positive or (less preferably) a negative thermal coefficient of resistance. A control feedback circuit is needed with a negative coefficient of resistance for temperature regulation.

Materials that are described by way of example herein to be suitable for use in certain embodiments of the present invention will be capable of this function. Depending on other components and/or materials that are present, examples of suitable materials include carbon fibres and fabric, such as a woven layer or sheet, which may as appropriate be made essentially of carbonised acrylate, such as polyacrylonitrile and copolymers thereof.

(ii) an electrically insulating flat sheet or membrane substrate that has sites on its surface that are connected by an array of electrically resistive but conductive tracks, traces, outlines, or other like structures, e.g. filled channels, conduit and the like, and, e.g. etched foil, which generate thermal energy when a voltage drop is applied over them. The array may be a parallel array with spaces therebetween, connected together at each end, or comprise or consist essentially of one or more such integers in a spiral, or in a meandering, tortuous, winding, zigzag, serpentine or boustrophedic (i.e. in the manner of a ploughed furrow) pattern. Examples of suitable materials for the array of electrically resistive but conductive tracks, traces, outlines, or other like structures include carbon and/or metals, such as Thermion™, a nickel-coated non-woven carbon fabric and resistance heating alloys, such as Kanthal™ Alkrothal™ Nikrothal™, and Nifethal™. For the electrically insulating flat sheet or membrane substrate, suitable materials include PTFE, polyamides, and (i) materials such as aromatic polysulphones, polyethersulphones, polyetherether-sulphones, polyketones, polyetherketones; and polyetherether-ketones, and sulphonated derivatives thereof, and mixtures thereof; and (ii) expoxy resins. The array of electrically resistive but conductive tracks, traces, outlines, or other like structures, may be generated by etching or engraving, e.g. with electron beam irradiation and/or with fluid chemicals. Alternatively, where appropriate it may be provided by printing, imprinting, stamping or vapour deposition of conventional type.

(iii) an array of electrically resistive but conductive, mutually connected thermocouples that are potentially capable of generating thermal energy by the Peltier effect when a voltage drop is applied over them. The array may be a parallel array with spaces therebetween, and the wound irrigant and/or wound exudate may move through the spaces. Alternatively, it may be permanently or releasably attached to the surface of a substrate of the type described by way of example under ii) as suitable for use in certain embodiments of the present invention. Depending on other components and/or materials that are present, examples of suitable materials include thermoelectric modules comprising pellets of bismuth telluride doped with selenium and antimony of different conductivity, the thermocouple pairs being connected in series and sandwiched between ceramic substrates. In the Peltier effect when a voltage drop is applied over a thermocouple, one part potentially undergoes heating, and can thus supply thermal energy to the wound through a heat transfer medium (the irrigant). The other part undergoes cooling and can thus act as a thermal pump from the ambient to the fluid irrigant and exudate in the apparatus flow path to the wound. However, thermal energy transfer in this highly controllable manner requires orientation of the thermocouple array such that the side capable of gaining thermal energy by the Peltier effect is in conductive contact with the irrigant and/or wound exudate. Examples of (a) (i) & (ii) include a foam reservoir dressing, such as Allevyn (™, Smith & Nephew) and Tielle (™, Johnson & Johnson), having an electrical heater, mounted distally of the body on it.

(b) an inductive heater element mounted in conductive contact with irrigant and/or wound exudate (but electrically insulated from the fluid and the system in which the fluid moves and heat is conducted to the wound). The heater may inter alia comprises a piece of ferromagnetic material, such as magnetic stainless steel in conductive contact with irrigant and/or wound exudate, and an inductive source that will be adjacent (but not necessarily attached) to the dressing in use, but may otherwise be remote from the wound). Examples of the latter include a ferromagnetic coil, spiral, helix or spiral helix, or loop or a more convoluted form, e.g. a meandering, tortuous, winding, zigzag, serpentine or boustrophedic (i.e. in the manner of a ploughed furrow) pattern, in particular in one plane, of an inductive often highly conductive material, connected to an alternating electrical potential source. This is potentially capable of generating thermal energy in the core when a varying potential is applied to the coil, spiral or spiral helix, or loop or a more convoluted form. This is often at mains voltage and frequency at the location where the device is used, though a range of either may be used.

(c) a heater mounted in conductive contact with irrigant and/or wound exudate to which it transfers thermal energy to the fluid in recirculation from a heat source within it, which is a fuel cell. In this, atmospheric oxygen and/or other molecules oxidise one or more species of fuel molecules, often in a catalytic bed. Examples of fuel materials that have a strong oxidation exotherm include gases, where the gaseous phase of the aerosol system is air and a fuel gas, such as hydrogen or an alkane, such as methane, ethane and butane. The catalyst is often solid particulates, such as composites of copper and rare earth oxides, such as optionally samaria doped ceria. comprised in a crystalline material for convenient handling; or platinum powder coated onto carbon paper or cloth.

(d) a heater mounted in conductive contact with irrigant and/or wound exudate to which it transfers thermal energy to the fluid in recirculation from a heat source within it, which is a material that undergoes a highly exothermal phase change. Examples of (d) include (i) a heater containing materials that undergo a highly exothermal crystallisation or solidification phase change, such as supersaturated solutions of chemicals, such as metal ion salts. Sodium thiosulphate is a source of a strong crystallisation exotherm, as is sodium acetate solution. The fluid or solid material is often comprised in one or more conformable hollow bodies. These may be defined by, for example a polymer film, sheet or membrane, such as a bag, chamber, pouch or other structure, of the backing layer, e.g. of polymer film, for convenient handling. In the case where the heat source is in the form of a crystallisation system, such as one based on sodium thiosulphate, the bag, chamber, pouch or other structure is often provided with a source of mechanical shock that is appropriate for inducing crystallisation. Examples include a catastrophically resiliently flexible or stiff metal button, such as one of e.g. aluminium or stainless steel. Such heaters are less preferred than an electrical heater, since electrical heating can give constant heating intensities in a highly controllable manner. In contrast, a strong crystallisation or solidification exotherm is less controllable or constant.

(ii) a heater containing materials that undergo an exothermal condensation phase change, i.e. from gaseous or volatile products, such as the Freon hydrocarbon series to liquids. Preferred materials include, in particular those that condense at or near normothermic temperature. Such a heater of the irrigant fluid and/or wound exudate may be operated as a heat pump that absorbs thermal energy, e.g. from the environment of a component of the apparatus flow path into the component of the apparatus flow path. In examples of (a) direct electromagnetic irradiation at an appropriate wavelength, e.g. infrared and/or near infrared from a radiative heater of the irrigant fluid and/or wound exudate; and/or (b) electromagnetic irradiation from a radiative heater of a component of the apparatus flow path that absorbs electromagnetic irradiation at an appropriate wavelength, e.g. infrared and/or near infrared and is in direct conductive contact with the irrigant and/or wound exudate. The heater usually works at such temperatures as will deliver 34 to 55° C., preferably 35 to 42° C., and optimally 36 to 38° C. at the wound bed. Examples of sources of direct or indirect electromagnetic irradiation of the irrigant fluid and/or wound exudate at an appropriate wavelength include infrared and/or near infrared from a radiative heater. In the apparatus the type and materials of the heater will be largely determined by its specific function and the wavelengths and intensities to be applied to the fluid within the far infrared, mid infrared or near infrared spectrum, and its position in the apparatus. Examples of suitable wavelengths to apply to the fluid include: (a) for the far infrared, 4 to 1000 micrometre, (b) for the mid infrared, 1.4 to 4 micrometre, and (c) for the near infrared, 0.75 to 1.5 micrometre. Examples of suitable levels of intensity include those conventionally used in medical applications and known to the skilled person. The higher end of these ranges are potentially more suitable for hospital use, where relatively high intensity infrared or near infrared irradiation at relevant wavelengths may be used safely under professional supervision. Such a device may also suitably be one that is capable of pulsed, continuous, variable, and/or automated and/or programmable operation. Examples include:

(i) a radiative heater that is an incandescent filament lamp, light or other like structure, which is a source of radiation at relevant wavelengths to be applied to the fluid, e.g. infrared or near infrared irradiation. Examples of (i) include a heater that is a small infrared lamp, mounted on an infra-red transparent dressing backing layer;

(ii) a radiative heater that is a high-thermal energy, high-intensity LED (light emitting diode) or other like structure, which is a source of radiation at relevant wavelengths to be applied to the fluid, e.g. infrared or near infrared irradiation; and (iii) a radiative heater that is a high-thermal energy, high-intensity source of radiation at relevant wavelengths to be applied to the fluid, e.g. infrared or near infrared irradiation. The type and materials of the heater will be largely determined by its specific function and the wavelengths and intensities to be applied to the fluid within the spectrum, and its position in the apparatus.

(e) Any r.f. and/or microwave frequency signal generator may be used provided temperatures at the wound do not exceed 38 to 40° C., and optimally 36 to 38° C. Examples of sources of direct or indirect electromagnetic irradiation of the irrigant fluid and/or wound exudate at an appropriate wavelength also include radio-frequency e.m.r. in a range of 3 to 300 MHz, such as 10 to 100 MHz, such as 20 to 50 MHz. Examples of preferred frequencies include microwave frequencies, using a microwave magnetron, in a range such as 1 to 300 GHz, such as 1 to 100 GHz, e.g. 1 to 50 GHz. It will be appreciated that at these frequencies, in the range of microwave frequencies in particular, thermal energy is not just transferred to the fluid by simply being absorbed by the fluid and conducted to the wound. It is induced in the molecules in the fluid in the wound by radiation at an optimum frequency for such materials.

In all the above radiative heaters of the irrigant fluid and/or wound exudate, the electromagnetic irradiation from a radiative heater may pass into the fluid in the flow path directly, usually through a 'window' that is transparent to the relevant wavelengths to be applied to the fluid.

Amongst those materials that are suitable are glass; carbon fibres (which may be in a parallel array with spaces therebetween) and carbon fabric, such as a woven layer or sheet. This may as appropriate be made essentially of carbonised acrylate, such as polyacrylonitrile and copolymers thereof; and various well-known polymers.

The transmissive structures may, alternatively or additionally, effectively be in the form of optical fibre(s) or waveguides of conventional type, e.g. (a) a tube, pipe, duct, fibre, filament, strand or other like structure, e.g. of carbon or the materials mentioned above, which is transparent to the relevant wavelengths to be applied to the fluid, (b) coated, enclosed or enveloped by a coating, layer, sheet, skin or concentric tube, pipe, duct, sheath, or casing, or other like structure, of material on its outer face that is opaque and reflective to the relevant wavelengths.

These may pass at any relevant position along the apparatus flow path into the apparatus flow path where the heat is desired to be applied. In one embodiment, they will pass under and/or through the backing layer of the dressing. The transmissive structures may effectively be in the form of optical fibre(s) formed by (a) at least one inlet pipe and/or fluid supply tube and/or and/or at least one outlet pipe and/or fluid offtake tube, which passes through and/or under the wound-facing face, and is transparent or translucent to the relevant wavelengths to be applied to the fluid in the wound, and preferably to those that are optimum for wound healing, (b) coated, enclosed or enveloped by a coating, layer, sheet, skin or concentric tube, pipe, duct, sheath, or casing, or other like structure, of material on its outer face that is opaque and reflective to the relevant wavelengths. An advantage of such wound dressings is that these optical fibres may also serve as diagnostic 'keyholes' into the dressing to the wound bed in order to inspect the wound and assess its status. This is a significant advantage, in particular in chronic wounds.

As noted above, radiative energy may be absorbed by a component of the apparatus flow path that absorbs electromagnetic irradiation at an appropriate wavelength, e.g. infrared and/or near infrared and is in direct conductive contact with the irrigant and/or wound exudate. Thus a radiative heater may be radiatively connected to a component of the apparatus flow path that absorbs electromagnetic irradiation at an appropriate wavelength, e.g. infrared and/or near infrared and is in direct conductive contact with the irrigant and/or wound exudate, e.g. by an air gap, the component containing a suitable absorbent and transmissive structure, e.g. an aqueous fluid, such as a hydrogel, that conducts heat through it to the irrigant fluid.

The temperature of the wound under the wound-facing face of the backing layer of the wound dressing is generally held at a desired level, often that for optimum performance of the wound healing process, such as a temperature found in the relevant bodily part, often within a range of temperatures such as 34 to 55° C., preferably 35 to 42° C., and optimally 36 to 38° C. at the wound bed. The temperature of the wound under the wound-facing face of the backing layer of the wound dressing is generally held at a constant level throughout the desired length of therapy, but may be varied cyclically in a desired regime.

However, the temperatures noted above, which are at or near the temperature naturally occurring in the relevant bodily part may not provide a system for optimum performance of the wound healing process. It may be desirable that the interior of the wound dressing is more beneficially maintained at a temperature that degrades such molecules in the fluid in the wound, e.g. an appropriate optimum degradation temperatures for such materials, rather than at normothermic temperature. This may be the case in particular in chronic wounds, with relatively high concentrations of materials that are deleterious to wound healing. Other molecules involved in wound processes that are detrimental to wound healing include or gaseous or volatile by-products, such as carbon dioxide. The irrigant may be warmed to a temperature that tends to degrade and/or outgas such molecules. The degradation or outgassing temperature of each detrimental gas, such as carbon dioxide, in aqueous media is either known or may readily be calculated.

Accordingly, another type of this apparatus for irrigating, supplying thermal energy to and cleansing wounds is provided with means for maintaining the wound at or near a temperature that is deleterious to molecules that are detrimental to wound healing. As noted above, other physiologically active components of the wound cells are beneficial in promoting wound healing and may be stimulated by radiation on the wound under the backing layer. Where these are enzymes, growth factors and anti-inflammatories, cell mitochondria and other physiologically active components of the exudate from a wound, examples of suitable wavelengths and intensities to apply to the fluid in the wound to favour such materials an cell components will be known to the skilled person.

Additionally, it is easy to avoid overheating of the wound and/or surrounding surfaces, especially by electrical heating, since the heating must always pass to the wound through a heat transfer medium (the irrigant). This eliminates direct contact of the wound bed with the heater, and irrigant may be used as a heat transfer medium in a highly controllable manner.

The apparatus is most favourable to the wound healing process in chronic wounds, and thus for irrigating, and/or cleansing wounds such as diabetic foot ulcers, and especially decubitus pressure ulcers.

In a preferred mode, certain embodiments of the present invention are used to provide a system of therapy which conveniently cleanses wounds, but also maintains them at or near normothermic temperature. Accordingly a preferred type of the apparatus for irrigating, and/or cleansing wounds is provided with means for maintaining the wound at or near normothermic temperatures.

As noted above, the apparatus for irrigating, and/or cleansing wounds has a direct effect on active components of fluid in contact with the wound, in particular solutes or disperse phase species that are beneficial in promoting wound healing that are in contact with the wound bed. Additionally, cell mitochondria aid proliferation and hence wound healing, in particular in chronic wounds, and are stimulated by near infrared radiation. Application of such radiation to the wound resulting in an increase in cell proliferation in the tissue underlying to the wound, and in the breaking strength of the new tissue. Other physiologically active components of the cells in the tissue underlying the wound that are beneficial in promoting wound healing may also be stimulated by radiation on the wound.

Physiologically Active Materials

The apparatus for aspirating, irrigating, and/or cleansing wounds may, in certain embodiments, further comprise means for supplying physiologically cative materials to the wound. The present form of aspiration and/or irrigation therapy systems also often create a wound environment for better distribution of materials that are beneficial in some therapeutic aspect, in particular to wound healing, that are present in a wound, but may not be well distributed in the wound, e.g. in a highly exuding wound (These include cytokines, enzymes, growth factors, cell matrix components, biological signalling molecules and other physiologically active components of the exudate.), and or materials contained in the irrigant that are potentially or actually beneficial in respect of wound healing, such as nutrients for wound cells to aid proliferation, and gases, such as oxygen, and such as those noted below in this regard, e.g. growth factors and other physiologically active materials. These may aid wound cell proliferation and new tissue growth that has a strong three-dimensional structure adhering well to and growing from the wound bed. This is a significant advantage, in particular in chronic wounds. This is especially the case in those embodiments of the apparatus for aspirating, irrigating, and/or cleansing wounds where there is an inlet manifold as described below. This covers and contacts most of the wound bed with openings that deliver the fluid directly to the wound bed over an extended area.

It will be seen that the balance of fluid between fluid aspirated from the wound and irrigant supplied to the wound from the irrigant reservoir may provide a predetermined steady state concentration equilibrium of materials beneficial in promoting wound healing over the wound bed. Simultaneous aspiration of wound fluid and irrigation at a controlled flow rate aids in the attainment and maintenance of this equilibrium.

This confers an advantage over the wound dressings in use before the present invention with means for supplying physiologically active agents under conventional sequential aspiration and irrigation of the wound. In these, the physiologically active agents are often supplied to the wound bed through a foam, which acts as a baffle to reduce the rate of diffusion, thus creating a concentration gradient of the physiologically active agents from a high concentration at the inlet point on the dressing to a low concentration at the wound bed. It is therefore difficult to predict the concentration of actives at the wound bed. This effect is exacerbated by a counter-flow of exudate from the wound bed. Many such dressings with means for supplying physiologically active agents to the wound bed also have a concentration gradient of the physiologically active agents across the wound bed from a high concentration at the inlet point to a low concentration at the outlet point. It is therefore difficult to supply a uniform concentration of actives across the wound bed.

The inlet manifold in the wound dressings used in certain embodiments of the present invention covers and contacts most of the wound bed with openings that deliver the fluid directly to the wound bed over an extended area, and therefore reduces the concentration gradient. It is thus easy to predict the concentration of actives at the wound bed, and there tends to be no counter-flow of exudate from the wound bed. It is also easy to supply a uniform concentration of actives across the wound bed.

Simultaneous aspiration and irrigation of the wound provides advantages over topical bolus instillation, such as the pooled delivery of fluid to the wound bed by the application of a conventional sequential aspirate—irrigate—dwell cycle. These include (in addition to greater bioavailability to all areas of the wound surface as above), prolonged delivery between dressing changes and optimal dosing. In the latter case, sequentially irrigating and aspirating a wound means the need to flood the wound with one or more static fluid physiologically active component in higher dosage concentration than is necessary to achieve a therapeutically active level of such actives on the wound bed.

This is just to maintain a desired average therapeutically active level of such actives on the wound bed during the dwell time period of sequentially irrigating and aspirating a wound, since these dosage concentrations levels tend to drop during this dwell time period in the cycle. It will be seen that normally the level of such actives is effectively reduced to zero by the conventional sequential subsequent aspiration of the wound.

Less desirably, it has been observed that some of such physiologically active components, for example factors such as TGFβ show different effects at high and low concentrations. An unnecessarily high dose to ensure activity during the residence between typical bolus instillations in conventional sequential irrigation—aspiration of the wound may result in less than optimum dosing and performance of the body's own tissue healing processes. Even less desirably, some of such physiologically active components may have adverse effects at higher concentrations. An unnecessarily high dose to ensure activity during the residence between typical bolus instillations in conventional sequential operation may result in undesirable effects on the wound bed. All of this may result in slow healing and/or slowing down of the healing, and growth lacking a strong three-dimensional structure adhering well to and growing from the wound bed. This is a significant disadvantage, in particular in chronic wounds.

Some embodiments of the apparatus for aspirating, irrigating and/or cleansing wounds with supply to the wound bed under a positive pressure may be advantageous. Application of a positive pressure to the wound under the backing layer may make it possible to flood the tissue underlying the wound with one or more physiologically active components in therapeutically active amounts. This may promote greater wound healing than by treatment with static fluid physiologically active component(s) alone or by sequential intermittent application of irrigant flow and aspiration The prolonged delivery of such physiologically active components in therapeutically active amounts in a precise and time-controlled manner by simultaneous aspiration and irrigation, together with (a) the removal of materials deleterious to wound healing from wound exudate, (b) without substantially diluting materials that are beneficial in promoting wound healing in contact with the wound bed, and (c) the continuously supply of such materials to the wound, promotes greater wound healing than (i) by treatment with the fluid physiologically active component(s) alone, or (ii) by topical bolus instillation in known aspirating and irrigating apparatus.

The supply of physiologically active materials may be effected at any appropriate point for this purpose along the apparatus flow path. It is often convenient to effect such supply to the wound via the fluid passing through the wound dressing from irrigant in the fluid reservoir that contains them.

Thus, one embodiment of the apparatus for irrigating, cleansing and/or aspirating wounds of the present invention is characterised in that it comprises an irrigant fluid in the fluid reservoir which in turn comprises one or more physiologically active components in amounts to promote wound healing. The prolonged delivery of such physiologically active components in therapeutically active amounts in a precise and time-controlled manner by simultaneous aspiration and irrigation, together with (a) the removal of materials deleterious to wound healing from the wound, and (b) the continuous supply of materials that are beneficial in promoting wound healing (that have been added using cells or tissue) to the wound bed, promotes greater wound healing than (i) by treatment with the fluid physiologically active component(s) alone, or (ii) by topical bolus delivery in known aspirating and irrigating apparatus. Advantages over topical bolus delivery include greater bioavailability to all areas of the wound surface, prolonged delivery between dressing changes and optimal dosing.

For example, factors such as TGFβ show different effects at high and low concentrations. Consequently, undesirable affects may be the result of an unnecessarily high dose to ensure prolonged residence between topical applications.

Supply to the wound bed under a positive pressure may be advantageous, as appplication of a positive pressure to the wound under the backing layer may make it possible to flood the tissue underlying the wound with one or more physiologically active components, added using cells or tissue, in therapeutically active amounts, to promote greater wound healing, than by treatment with physiologically active component(s) in static fluid alone.

It is foreseen that the actives to be added to the wound bed may be the nutrient medium, that human or mammalian cells e.g. keratinocytes, fibroblast or a mixture of these cells, or others for instance, have grown in conditioned media. The cells will release beneficial actives to the media e.g. TGFβ that would benefit the wound bed and aid healing of the wound.

In some embodiments of the present invention the actual cells themselves with or without the cells growth media, may be used as an active to the wound bed to aid healing. In particular embodiments of the present invention different types of cells maybe used as actives at different times of the healing process. For example, fibroblast type cells maybe used as an active to the wound bed to aid healing initially in order to help would remodelling and aid the wound to lay down structural fibres. Then keratinocytes or a larger proportion of keratinocytes than initially used before could be used as an active flowing along the wound bed to aid healing. Other cells could be used as well or combination thereof.

It is foreseen that the cells (keratinocytes or fibroblasts) can aid healing of the wound by giving beneficial healing components or by sticking to the wound bed and aiding healing directly.

When conditioned media is used, (the media that has had cells grown in it) different conditioned media from different cell source may be used and it is envisaged that having a particular order to which conditioned media to use may be important and aid healing. For example, conditioned media from fibroblast type cells or a mixture of cells comprising a high proportion of fibroblast cells may be used initially followed by a conditioned media from keratinocyte type cells or a mixture of cells comprising a higher proportion of keratinocyte than used before. It is foreseen that this will aid healing of the wound.

Moving wound fluid aids in movement of biological signalling molecules involved in wound healing (including such materials that have been added using cells or tissue) to locations in the wound bed that are favourable to (a) wound healing and/or to (b) cells that would otherwise not be exposed to them, e.g. in a highly exuding wound. This is especially the case in those embodiments of the apparatus for aspirating, irrigating and/or cleansing wounds where there is an inlet manifold that delivers the fluid directly to the wound bed over an extended area. Such materials include cytokines, enzymes, nutrients for wound cells to aid proliferation, oxygen, and other molecules that are beneficially involved in wound healing (including such materials that have been added using cells or tissue), such as growth factors, and others having beneficial effects (which may be further enhanced) in causing chemotaxis.

The apparatus for irrigating and/or aspirating wounds may be used cyclically and/or with reversal of flow. The means for supplying physiologically active agents from cells or tissue often conveniently comprises (a) an irrigant reservoir, (b) a container that contains a cell or tissue component, and (c) at least one supply tube for supplying physiologically active agents from cells or tissue and/or irrigant to the wound under the action of at least one device for moving fluid through the wound.

In use, irrigant is passed from the reservoir through the container that contains the cells or tissue and exits from it containing one or more physiologically active component materials that are beneficial in promoting wound healing that are expressed by the cells or tissue. The modified irrigant (including such physiologically active agents as have been added from the cells or tissue) is moved by a device for moving fluid through the supply tube and dressing to the wound. Then in admixture with wound exudate it is moved along the flow path, through the offtake tube.

In another embodiment of the apparatus for irrigating, cleansing and/or aspirating wounds of the present invention, the means for supplying physiologically active agents from cells or tissue to the wound comprises (a) an irrigant reservoir, and (b) a container that contains a cell or tissue component, (c) both connected in parallel to a supply tube for supplying physiologically active agents from cells or tissue and irrigant to the wound under the action of at least one device for moving fluid through the wound.

In this embodiment of the apparatus, the irrigant reservoir and the container that contains a cell or tissue component may be, e.g. connected to the supply tube by a Y-junction. In use, irrigant is passed from the reservoir to the supply tube, and a fluid (which may be a nutrient medium for the cells or tissue) containing one or more physiologically active component materials that are beneficial in promoting wound healing that are expressed by the cells or tissue is passed from the container that contains the cells or tissue to the supply tube. The irrigant in admixture with such physiologically active agents as have been added from the cells or tissue is moved by a device for moving fluid through the wound to and through the wound.

In yet another embodiment of the apparatus for irrigating, cleansing and/or aspirating wounds of the present invention, the means for supplying physiologically active agents from cells or tissue to the wound comprises (a) an irrigant reservoir, connected to (b) a first supply tube for supplying irrigant to the wound under the action of at least one device for moving fluid through the wound, and (c) a container that contains a cell or tissue component, connected to (d) a second supply tube for supplying physiologically active agents from the cells or tissue the wound dressing.

In use, irrigant is passed from the reservoir to the first supply tube for supplying irrigant to the wound. The fluid containing one or more physiologically active component materials that are beneficial in promoting wound healing that are expressed by the cells or tissue is passed from the container that contains the cells or tissue to the second supply tube for supplying physiologically active agents from the cells or tissue the wound dressing. Each is moved by a device for moving fluid through the wound to and through the wound. The irrigant is admixed in the wound space with the physiologically active agents that have been added from the cells or tissue.

In a further embodiment of the apparatus for irrigating, cleansing and/or aspirating wounds of the present invention, the means for supplying physiologically active agents from cells or tissue to the wound comprises (a) an irrigant reservoir connected to (b) a container that contains a cell or tissue component, under the backing layer, and which communicates with the wound via at least one channel or conduit for supplying physiologically active agents from cells or tissue and irrigant to the wound under the action of at least one device for moving fluid through the wound.

The container that contains a cell or tissue component may be integral with the other components of the dressing, in particular the backing layer. Alternatively, it may be permanently or demountably attached to them/it, with an adhesive film, for example, or by heat-sealing. In use, irrigant is passed from the reservoir through the container that contains the cells or tissue and exits from it into the wound space under the backing layer proximal face containing one or more physiologically active component materials that are beneficial in promoting wound healing that are expressed by the cells or tissue.

In yet a further embodiment of the apparatus for irrigating, cleansing and/or aspirating wounds of the present invention, the means for supplying physiologically active agents from cells or tissue to the wound comprises (a) a first irrigant reservoir connected to (b) a supply tube for supplying irrigant to the wound under the action of at least one device for moving fluid through the wound, and (c) a second irrigant reservoir connected to (d) a container that contains a cell or tissue component, under the backing layer, and which communicates with the wound via at least one channel or conduit for supplying physiologically active agents from cells or tissue and irrigant to the wound under the action of at least one device for moving fluid through the wound. The container that contains a cell or tissue component may be integral with the other components of the dressing, in particular the backing layer. Alternatively, it may be permanently or demountably attached to them/it, with an adhesive film, for example, or by heat-sealing.

In use, irrigant is passed from the first reservoir to the supply tube for supplying irrigant to the wound. Irrigant is also passed from the second reservoir to the container. The fluid containing one or more physiologically active component materials that are beneficial in promoting wound healing that are expressed by the cells or tissue is passed from the container that contains the cells or tissue to the second supply tube for supplying physiologically active agents from the cells or tissue the wound dressing. Each is moved by a device for moving fluid through the wound to and through the wound. The irrigant is admixed in the wound space with the modified irrigant containing physiologically active agents that have been added from the cells or tissue.

All of these embodiments of the means for supplying physiologically active agents from cells or tissue to the wound may use cells or tissues of two or more different types. In such systems, a first input cell or tissue type is often contained in a first container, and a second input cell or tissue type is often contained in a second container. The two input cell or tissue types and containers may feed physiologically active agents in parallel to the dressing and to the wound bed under the action of at least one device for moving fluid through the wound.

To achieve therapeutically effective amounts of materials that are beneficial in promoting wound healing, a fluid flow though and/or over the cells or tissue may have to be maintained over multiple cycles, with significant dwell times and/or over significant periods of time.

Thus, in those embodiments of the means for supplying physiologically active agents from cells or tissue to the wound described above, the container that contains a cell or tissue component may be provided with (a) means for recycling nutrient medium for the cells or tissue from and back to a nutrient medium reservoir, e.g. a loop comprising the reservoir, connected to the container that contains the cells or tissue, with a pump, and in particular (b) means for switching fluid flow between recycling around the loop comprising the reservoir and the container and supply to the relevant supply tube. Such means for switching fluid flow may comprise at least one one-way valve in the loop and in the fluid supply tube, or a two way valve connecting the supply tube and the loop.

In use, nutrient medium for the cells or tissue is recycled from and back to a nutrient medium reservoir in the loop comprising the reservoir and the container that contains the cells or tissue, with a pump, over multiple cycles, with significant dwell times and/or over significant periods of time until the cell proliferation in the cells or tissue in the container that contains the cells or tissue and/or the expression by such cells or tissue of one or more physiologically active component materials that are beneficial in promoting wound healing have achieved the desired levels.

Recycling nutrient medium for the cells or tissue from and back to the nutrient medium reservoir is then stopped, and supply to the relevant supply tube is started.

This may be achieved by stopping the pump and/or closing a one-way valve in the loop and opening on in the supply tube, or by switching a two way valve connecting the supply tube and the loop. The necessary desired levels of physiologically active component materials, valves, pumps, number of cycles, dwell times and/or time periods will be apparent to the skilled person.

As noted above, in another embodiment of the apparatus for aspirating, irrigating and/or cleansing wounds, a particular advantage is that the means for supplying physiologically active agents from cells or tissue to the wound lies within the wound dressing. In use, irrigant is passed from the reservoir through the cells or tissue component for supplying physiologically active agents to the wound which lies within the wound dressing, and exits from it containing one or more component physiologically active component materials that are beneficial in promoting wound healing that are expressed by the cells or tissue. The modified irrigant (including such physiologically active agents as have been added from the cells or tissue) in admixture with wound exudate is moved by the device for moving fluid through the offtake tube along the flow path.

Thus, one embodiment of the apparatus for irrigating, cleansing and/or aspirating wounds of the present invention is characterised in that it the means for supplying physiologically active agents from cells or tissue to the wound comprises (a) an irrigant reservoir fluidically connected to (b) a wound dressing that contains a cell or tissue component.

The wound dressing backing layer, which is capable of forming a relatively fluid-tight seal or closure over a wound, and the wound bed define a wound space, which contains cells or tissue. As noted above for a separate container, the wound space may contain a cell or tissue component that is not bound to an insoluble and immobilised substrate over and/or through which the irrigant and/or wound exudate from the wound passes. It then also appropriately comprises two or more integers which are permeable to the wound exudate or a mixture with irrigant, but have apertures, holes, openings, orifices, slits or pores of sufficiently small cross-dimension to hold the cell or tissue component, and to retain particulates, e.g. cell debris, in the hollow body.

Each of the integers may then effectively form a macroscopic and/or microscopic filter. Alternatively, it may contain a cell or tissue component that is bound to an insoluble and immobilised substrate over and/or through which the irrigant and/or wound exudate from the wound passes, e.g. a scaffold. This will often be of a material, and may typically be in the form, noted above as amongst those that are suitable for such components of a separate container that contains a cell or tissue component.

The wound space may contain a cell or tissue component at any appropriate point in contact with the irrigant and/or wound exudate, and the component may be as appropriate, adhered or otherwise secured to any integer of the wound dressing, e.g. the dressing backing layer or a wound filler, or it may be a separate structures, permanently unattached. It may often lie in contact with the wound bed. Where it does so, it may be advantageous if it is (a) bound to an insoluble and immobilised substrate over and/or through which the irrigant and/or wound exudate from the wound passes, or (b) not bound to an insoluble and immobilised substrate, but comprised in two or more integers which are permeable to the wound exudate or a mixture with irrigant, and (c) comprises a biodegradable mesh, grid, lattice, net or web, with apertures, holes, openings, orifices, slits or pores of small cross-dimension in contact with the wound bed.

The cell or tissue component in contact with continuously supplied irrigant and/or wound exudate has the ability to add elements beneficial to wound healing to the irrigant, but the same elements also aid proliferation of wound bed cells into the apertures, holes, openings, orifices, slits or pores of small cross-dimension of the biodegradable mesh, grid, lattice, net or web, which is also beneficial to wound healing.

In general, the tissue component has the ability to elaborate or express materials beneficial to wound healing to the irrigant to modify the irrigant. As described in further detail hereinafter, such elements beneficial to wound healing may be biochemical, e.g. enzymatic or physical antagonists to elements detrimental to wound healing in the exudate and/or exudate and irrigant.

An additional embodiment of the apparatus for irrigating, cleansing and/or aspirating wounds of the present invention is characterised in that the physiologically active components that have been added using cells or tissue in amounts to promote wound healing comprise materials that are beneficial in promoting wound healing by removing materials or by regulating, limiting or inhibiting processes deleterious to wound healing.

Depending on the particular type of wound being treated and the particular cells or tissue used in the present apparatus for aspirating, irrigating and/or cleansing wounds, the deleterious materials to be removed may include (a) proteases, such as serine proteases, e.g. elastase and thrombin; cysteine proteases; matrix metalloproteases, e.g. collagenase; and carboxyl (acid) proteases; (b) inhibitors of angiogenesis such as thrombospondin-1 (TSP-1), Plasminogen activator inhibitor, or angiostatin (plasminogen fragment); (c) pro-inflammatory cytokines such as tumour necrosis factor alpha (TNFα) and interleukin 1 beta (IL-1β); and (d) inflammatories, such as lipopolysaccharides, and e.g. histamine.

Materials deleterious to wound healing that are removed using the apparatus may also include: (a) oxidants, such as free radicals, e.g. peroxide and superoxide; (b) iron II and iron III; (c) all involved in oxidative stress on the wound bed; (d) proteases, such as serine proteases, e.g. elastase and thrombin; cysteine proteases; matrix metalloproteases, e.g. collagenase; and carboxyl (acid) proteases; (e) endotoxins, such as lipopolysaccharides; (f) autoinducer signalling molecules, such as homoserine lactone derivatives, e.g. oxo-alkyl derivatives; (g) inhibitors of angiogenesis such as thrombospondin-1 (TSP-1), plasminogen activator inhibitor, or angiostatin (plasminogen fragment); (h) pro-inflammatory cytokines such as tumour necrosis factor alpha (TNFα) and interleukin 1 beta (IL-1β), (i) oxidants, such as free radicals, e.g., e.g. peroxide and superoxide; and (j) metal ions, e.g. iron II and iron III, all involved in oxidative stress on the wound bed.

It is believed that aspirating wound fluid aids in removal from of the materials deleterious to wound healing from wound exudate and/or irrigant, whilst distributing materials that are beneficial in promoting wound healing in contact with the wound. A steady state concentration equilibrium of materials beneficial in promoting wound healing may be set up between in the irrigant and/or wound exudate. Aspirating wound fluid aids in the quicker attainment of this equilibrium Materials beneficial to wound healing that are distributed include (a) cytokines, enzymes, growth factors, cell matrix components, biological signalling molecules and other physiologically active components of the exudate and/or (b) materials in the irrigant that are potentially or actually beneficial in respect of wound healing, such as nutrients for wound cells to aid proliferation, gases, such as oxygen.

Again, depending on the particular type of wound being treated and the particular cells or tissue used in the present apparatus for aspirating, irrigating and/or cleansing wounds, the beneficial materials to be added may include antagonists to the materials deleterious to wound healing in the wound exudate, such as, for example (a) enzymes or others, such as protease inhibitors, such as serine protease inhibitors, cysteine protease inhibitors; matrix metalloprotease inhibitors; and carboxyl (acid) protease inhibitors; (b) binders and/or degraders, such as anti-inflammatory materials to bind or destroy lipopolysaccharides, e.g. peptidomimetics. They further include (a) peptides (including cytokines, e.g. bacterial cytokines, such as α-amino-γ-butyrolactone and L-homocarnosine); and (b) other physiologically active components.

Examples of antagonists to such materials also include (a) natural proteins or recombinant-produced protein, proteinase inhibitors, such as tissue inhibitors of metalloproteinases (TIMP 1 to 4) and alpha 1-antitrypsin (AAT), aprotinin, α-2-macroglogulin; (b) antibodies or other molecules at inappropriate levels that inhibit or inactivate processes or materials deleterious to wound healing, such as matrix metalloproteinases (MMPs), neutrophil elastase, inhibitors of new blood vessel formation (angiogenesis) such as thrombospondin or kallistatin and combinations thereof.

The irrigant may alternatively or additionally, where appropriate, deliver a steady supply of natural proteins or recombinant-produced protein debriding agents to remove and limit eschar, necrotic cells and tissues from the wound bed. Examples of such include stretoptokinase, plasmin, trypsin, collagenases, and other selective proteases or fibrinolytic factors and combinations thereof.

The irrigant supplied to the wound dressing may alternatively or additionally, where appropriate, contain materials added using cells or tissue such as (a) antioxidants, such as ascorbic acid or stable derivatives thereof and (b) free radical scavengers, such as gutathione or natural proteins or recombinant-produced proteins such as superoxide dismutase (SOD), or (c) free radical generators to balance the oxidative stress and oxidant potential of the wound bed in order to maximize the opportunity for wound healing.

The active material may act beneficially on the wound bed and have the ability to aid wound healing, as it is passed by the device through the flow path, through biochemical, enzymatic or physical means without any such role as a biochemical, enzymatic or physical antagonist. Examples of such components (however supplied) include: (a) autologous, allogeneic or xenogeneic blood or blood products, such as platelet lysates, plasma or serum; (b) natural purified proteins or recombinant-produced protein growth factors, such as platelet derived growth factor (PDGF), vascular endothelial growth factor (VEGF), transforming growth factor alpha (TGFα) or transforming growth factor beta (TGFβ-1, 2 or 3), basic-fibroblast growth factor (b-FGF also known as FGF2), epidermal growth factor (EGF), granulocyte-macrophage colony-stimulating factor (GM-CSF); insulin like growth factor-1 (IGF-1) and keratinocyte growth factor 2 KGF2 (also known as FGF7); (c) natural purified proteins or recombinant produced protein cytokines such as the interleukin 1β (IL1β), or interleukin 8 (IL-8) and (d) other physiologically active agents whether present normally in acute or chronic wounds, that can be augmented in the irrigant fluid to be of benefit to the wound bed, when such therapy is applied, and combinations thereof.

An additional embodiment of the apparatus for irrigating, cleansing and/or aspirating wounds of the present invention is characterised in the physiologically active components in amounts to promote wound healing comprise materials that are beneficial in promoting wound healing by removing materials or by regulating, limiting or inhibiting processes deleterious to wound healing from wound exudate.

Examples of such materials include (a) natural purified proteins or recombinant-produced protein, proteinase inhibitors, such as tissue inhibitors of metalloproteinases (TIMP 1 to 4) and alpha 1-antitrypsin (AAT), aprotinin, α-2-macroglogulin; (b) antibodies or chemically synthesised molecules at inappropriate levels that inhibit or inactivate processes or materials deleterious to wound healing from wound exudate, such as matrix metalloproteinases (MMPs), neutrophil elastase, inhibitors of new blood vessel formation (angiogenesis) such as thrombospondin or kallistatin and combinations thereof.

The irrigant may alternatively or additionally, where appropriate, deliver a steady supply of natural purified proteins or recombinant-produced protein debriding agents to remove and limit eschar, necrotic cells and tissues from the wound bed. Examples of such include stretoptokinase, plasmin, trypsin, collagenases, and other selective proteases or fibrinolytic factors and combinations thereof.

The irrigant supplied to the wound dressing, optionally under a positive pressure on the wound bed, may alternatively or additionally, where appropriate, contain (a) antioxidants, such as ascorbic acid or stable derivatives thereof and (b) free radical scavengers, such as gutathione or natural purified proteins or recombinant-produced proteins such as superoxide dismutase (SOD) or (c) free radical generators (such as hydrogen peroxide) to balance the oxidative stress and oxidant potential of the wound bed in order to maximize the opportunity for wound healing.

The irrigant supplied to the wound dressing under a negative or positive pressure on the wound bed may alternatively or additionally, where appropriate, contain nutrients for wound cells to aid proliferation or migration or the synthesis of matrix components or factors beneficial to wound healing, such as sugars, amino acids, purines, pyrimidines, vitamins, metal ions or minerals, or any such ingredients that may be found in either serum containing or serum-free cell culture medium or might be used as nutritional supplements.

The irrigant supplied to the wound dressing under a negative or positive pressure on the wound bed may alternatively or additionally, where appropriate, contain medicaments, such as antimicrobials, examples of which include antibacterial agents, for example triclosan, iodine, metronidazole, cetrimide, chlorhexidine acetate; antifungal agents, for example sodium undecylenate, chlorhexidine, iodine or clotrimoxazole; antibiotics such as ciprofloxacin or clindamycin.

The irrigant supplied to the wound dressing under a negative or positive pressure on the wound bed may alternatively or additionally, where appropriate, include local analgesics/ anaesthetics, such as lignocaine, bupivicaine, or diclofenac to reduce wound pain or pain associated with the dressing:

The irrigant supplied to the wound dressing under a negative or positive pressure on the wound bed may alternatively or additionally, where appropriate supply materials to achieve the delivery of nucleic acid molecules as active genes or gene-containing vectors (DNA, RNA or modified versions thereof), as naked molecules, molecules complexed with nucleic acid binding carriers, molecules within liposomes or as virus vectors to give steady, measured delivery of gene therapeutic molecules to wound bed cells.

In the means for supplying physiologically active agents from cells or tissue to the wound, the irrigant from the reservoir that passes into and through the cell or tissue component often conveniently comprises cell culture medium species. Examples of the latter include (a) trace elements and/or other nutrients such as amino acids, sugars, low molecular weight tissue building blocks, purines, pyrimidines, vitamins, metal ions or minerals, and/or (b) gases, such as air, nitrogen, oxygen and/or nitric oxide, (c) to aid proliferation of the cells or tissue in the means and/or steady, measured expression and supply of physiologically active agents. In such case, materials that are listed above are also suitable therapeutic molecules to supply to wound bed cells to aid proliferation of the cells or tissue, and/or which are otherwise beneficial to wound healing. In such case, it may be desirable to provide a system in which the irrigant from the reservoir that passes into and through the cell or tissue component comprises cell culture medium species and thereafter is supplied to the wound bed via a supply tube into the flowpath wherever appropriate, so that such cell culture medium species pass with the irrigant to the wound bed.

The irrigant from the reservoir may be used to maintain an optimum temperature of the cells or tissue and/or for regulating the exchange of gases in a conventional manner apparent to the skilled person. It is necessary for such a system to also irrigate the wound at a practical rate with the physiologically active components in therapeutically active amounts.

Automated, programmable systems which can regulate the wound irrigant parameters and functions listed above in a precise and time-controlled manner are amongst those that are particularly suitable for use.

The tissue component may be an ex vivo (autologous, allogeneic or xenogenic) uncultured tissue explant. Alternatively the tissue component may be formed from separated or partially separated cells which have either been used without a period of culture or they may have been cultured in vitro. The process of culture may involve growth and proliferation or just incubation in culture. The source tissues may be tissue from any organ such as skin, muscle, bone, neural, connective tissue, intestinal, liver or amniotic tissue and other organs or combinations thereof, whose cells and tissue retain the appropriate properties. The cells or tissue may be fully viable or viable, but rendered non-dividing through irradiation or chemical treatment, or rendered non-viable after an appropriate period of culture.

Alternatively, the cells or tissue may be genetically modified to increase production of a particular material, e.g. a protein that is beneficial in promoting wound healing, such as a growth factor, an extracellular matrix component or fragments thereof, and other physiologically active components, or a biochemical, e.g. enzymatic or physical antagonists to elements detrimental to wound healing in the exudate and/or exudate and irrigant.

The tissue component that provides the active material that acts beneficially on the wound bed may consist of a co-culture. A co-culture encompasses the in vitro or ex vivo culture of two or more cell types or tissue explants. This might be with one or both input cells or tissues fully viable or viable, but rendered non-dividing, through irradiation or chemical treatment, or rendered non-viable after an appropriate period of culture. Alternatively, the cells or tissue may be genetically modified to increase production of a particular material, e.g. a protein that is beneficial in promoting wound healing, such as a growth factor, an extracellular matrix component or fragments thereof, and other physiologically active components, or a biochemical, e.g. enzymatic or physical antagonists to elements detrimental to wound healing in the exudate and/or irrigant.

The input cells or tissues may be intimately mixed or intermingled, or they may be present as layers one on the other. In some systems a semi permeable membrane or matrix between the component cells or tissues allows communication through biochemicals or proteins or other signals, but no cell apposition between the input cell types. In further systems modified irrigant is collected from one input cell or tissue type and given to the second input cell or type and given back to the first input cell type (sequentially or continuously) to generate the optimal output.

The cell or tissue component may be activated either singly or repeatedly through the delivery of biochemical, protein, enzymatic or physical means or through electromagnetic irradiation, ultrasonic or electrical stimulation. Preferably the present apparatus for aspirating, irrigating and/or cleansing wounds is a conventionally automated, programmable system which can cleanse the wound with minimal supervision.

Scaffold

In certain embodiments, the apparatus for aspirating, irrigating, and/or cleansing wounds further comprises a biodegradable scaffold.

A significant advantage, in particular in chronic wounds, is that in use granulation tissue is encouraged to grow onto and/or into a scaffold that lies between the wound dressing and the wound bed. The effect may be further enhanced by the circulation over the wound bed of irrigant from the fluid reservoir which contains nutrients for wound cells to aid proliferation, and other molecules that are beneficially involved in wound healing and/or that are favourable to the wound healing process.

A particular advantage is that it is unnecessary to remove this granulation tissue in-growth on dressing change, as the scaffold is left between the wound film dressing and the wound bed to biodegrade. This minimizes trauma and any need for debridement. A more specific advantage is that the scaffold prevents the overgrowth of tissue in the wound area. Another advantage of this apparatus is its use with pressure sores: the device can be placed in the depths of the wound and the patient can lie upon it without either affecting the utility of the device or further damaging the wound. This becomes critical if the patient cannot be moved from this posture for medical reasons.

In use, the scaffold is placed over substantially the expanse of the wound, and its size and configuration can be adjusted to fit the individual wound. It can be formed from a variety of apertured, semi-rigid materials. By 'apertured' herein is meant materials that are porous, apertured, holed, open-mesh, slit, incised and/or cut and the like. The material should be sufficiently apertured to allow for invasion by all manner of cells involved in the process of tissue repair and wound healing, and/or for the inward growth of blood vessels, and sufficiently rigid to prevent wound overgrowth and collapse under suction.

Suitable biomaterials for the biodegradable scaffold include poli(hydroxyl acids) and esters thereof, such as poly (glycolic acid), poly(L-lactic acid), poly(D-lactic acid) and esters thereof, and copolymers and blends of the aforementioned. Additionally, biologically sourced biodegradable polymeric materials such as substantially protein based polymers, for example; collagens, fibronectins, or fibrins, either as whole molecules or those subjected to proteolytic or chemical treatments, in either degraded or native conformations, or modified proteins produced by nucleic acids recombinant techniques, or combination thereof. Further acceptable scaffolds will be combinations of protein-based scaffolds and carbohydrate based polymers such as glycosoaminoglycans, chitosans, cellulose or alginate molecules. Suitable materials also include human or animal derived tissues processed in means to make them acceptable in placement into the wound such as skin, alimentary tract or connective tissues. The scaffold may be formed in a variety of apertured, semi-rigid forms.

These forms may be essentially two-dimensional, such as sheets, layers, films, flexible panels, meshes, nets, webs or lattices. They may be placed in the wound as dry, hydrated or gel based formulations. One embodiment of apertured or holed scaffold comprises a section of honeycombed polymer sheet cut to the shape of the wound.

Where the scaffold is in an essentially two-dimensional apertured, semi-rigid form, such as a sheet, layer, film, flexible panel, mesh, net, web or lattice, it may be designed in a configuration that is able to conform well to the wound bed on insertion into the wound. This conforming to shape is then a particular advantage in those embodiments where the wound dressing is used on deeper wounds, especially where a wound filler is used to urge the wound dressing towards the scaffold and wound bed, as described hereinafter in connection with the wound dressing.

By way of example, such a scaffold may be in the form of a deeply indented circular disc much like a multiple Maltese cross or a stylised rose, as is described hereinafter in connection with an inlet manifold shown in FIG. 18b. This form is able to conform well to the wound bed on insertion into the wound, especially a deeper wound, by the arms closing in and possibly overlapping. The form of the scaffold may also be three-dimensional, such as sheets, layers, films, flexible panels, meshes, nets, webs and lattices, folded, creased, pleated, tucked, crinkled, crumpled, screwed up or twisted into a three-dimensional form. Alternatively, these forms may be inherently three-dimensional, such as multilayers of films, flexible panels, meshes, nets, webs and lattices, or three-dimensional meshes, nets, webs and lattices, and favourably foams. They may be placed in the wound as dry, hydrated or gel based formulations.

One embodiment of an apertured or holed scaffold comprises a section of biodegradable polymer mesh, which permits (a) fluid supply towards the wound bed, (2) the withdrawal of tissue fluid through the pores of the scaffold and (3) the ingrowth of cells to yield the eventual replacement of the scaffold with new tissue under the influence of the suction force. A favoured embodiment of this apparatus comprises a section of knitted two- or three-dimensional mesh, in particular three-dimensional mesh. A preferred embodiment of this apparatus comprises a section of three-dimensional sponge as the biodegradable scaffold. Such scaffold can vary in thickness and rigidity, although it is preferred that a soft material be used for the patient's comfort if the patient must lie upon the device during its operation. Where the biodegradable scaffold comprises a mesh, the latter may be unwoven, woven or knitted, preferably knitted, and preferably three-dimensional.

Flow Stress

In some embodiments, the apparatus may include means for providing flow stress. The motion of fluids across a surface results in shear stresses within the surface. On a microscopic level such flow may cause other localised or general forces on areas of the surface. These forces or stresses are encompassed in the term flow stress as used herein. These are effects such as, but not limited to an increase in cell proliferation, debridement of necrotic tissue, removal of slough and to allow alignment of collagen fibres. This leads to improved breaking strength of tissue growth, to a strong three-dimensional structure adhering well to and growing from the wound bed, and reduction of wound recurrence.

The terms stress and strain have slightly different meanings, but in the context of this application, are often used interchangeably. "Stress" refers to a physical force acting upon a surface or structure, in this case a wound bed. Stress is typically defined as force per unit area on a surface. "Strain" refers to a mechanical deflection of a surface or structure caused by stress, again in this case a wound bed. Stress may cause strain, or vice versa, but in the context of the present application, where the term stress is used, it should be understood to refer to stress or strain of the wound bed. For example, applying a positive pressure to a wound bed will apply a stress to the surface of the wound bed, but will also apply a strain as the wound bed is a resilient structure which will deflect as a result of the pressure. On the other hand deflection of the wound bed in one area (i.e. applying a strain) may cause stress and/or strain in another area. Accordingly where the term stress or strain is used in the present application, they should not be taken in their strict mechanical meaning (although that may be appropriate) but should be understood to mean the deflection or application of force to the cells of the wound bed and or surrounding areas.

Such a stress or strain across the wound bed and optionally tissue surrounding the wound, e.g. an optionally varying positive and/or negative pressure applied to the wound, has been found to result in an increase in improvements to wound healing, such as an increase in cell proliferation, revascularisation, improved breaking strength and reduction of wound recurrence.

The resultant tissue growth has a strong three-dimensional structure adhering well to and growing from the wound bed. It also stimulates blood flow in underlying tissue and optionally tissue surrounding the wound.

Removal of fluid by optionally varying negative pressure leads to reduction of interstitial oedema and pressure directly affecting the lymphatic and capillary system, restoring lymph function.

All of these are beneficial to wound healing.

The application of stress and/or strain to a wound bed to improve healing is equally applicable to both sequential systems (i.e. empty/fill cycles) or simultaneous irrigate/aspirate systems. Although it is generally preferred to use a simultaneous system due to the benefits of such a system, there may be circumstances where a sequential system is preferred, e.g. due to cost.

Removal of excess fluid assists with the reduction of interstitial oedema and pressure directly affecting the lymphatic and capillary system, restoring lymph function and stimulating blood flow.

The means for applying flow stress to the wound bed in the apparatus for aspirating, irrigating and/or cleansing a wound according to an embodiment of the present invention include means for applying, controlling and/or varying fluid (i.e. irrigant and/or wound exudate) flow under the wound dressing as hereinbefore defined at any appropriate points across the wound bed.

These include (a) features in the conformation of the wound dressing, in particular in the wound facing face of the dressing in relation to the wound bed in use, and/or (b) features in the rest of the system in which the fluid moves, in particular the throughput of the device for moving fluid through the wound which give the appropriate or desired fluid flow rate or velocity of the irrigant and/or wound exudate under the wound dressing to cause flow stress at any appropriate points across the wound bed. These are described in detail hereinafter in connection with the operation of the apparatus.

It is sufficient to note here that features in the conformation of the wound dressing, in particular in the wound facing face of the dressing in relation to the wound bed in use, which give the appropriate or desired fluid flow rate or velocity of the irrigant and/or wound exudate under the wound dressing to cause flow stress at any appropriate points across the wound bed include irrigant inlet manifolds which contact or lie very close to the wound bed, irrigant inlet or outlet manifolds comprised in the dressing, which have apertures or pores by the wound bed that are of suitable total area over an extended area, projections, such as bulges or protuberances on the wound-facing face of the dressing, that are capable of directing flow.

Features in the rest of the system in which the fluid moves, in particular the throughput of the device for moving fluid through the wound, which give the appropriate or desired fluid flow rate or velocity of the fluid (i.e. irrigant and/or wound exudate) under the wound dressing to cause flow stress at any appropriate points across the wound bed include devices which impose: (i) relatively high flow rates or velocities, or rates of change in the flow rates or velocities, of irrigant and/or wound exudate flow under the wound dressing at any appropriate points across the wound bed; and/or (ii) a relatively high pressure drop between the interior of an inlet manifolds comprised in the dressing and the wound bed.

Change in the flow velocities of fluid (i.e. irrigant and/or wound exudate) flow under the wound dressing at any appropriate points across the wound bed include changes from positive to negative over the wound bed, i.e. reversing flow, in particular with relatively high rates of flow across the wound bed.

As noted hereinbefore, certain embodiments of the present invention advantageously provides a means for combining more than one therapy in a single dressing system, such as (a) removal of materials deleterious to wound healing from wound exudate, and (b) promoting wound healing, by stimulating new tissue growth adhering well to and growing from the wound bed, by creating stress across the wound bed and optionally tissue surrounding the wound.

Such flow stress across the wound bed may also advantageously act against wound bacteria, by (a) breaking up biofilm growth before it develops a strong three-dimensional structure adhering well to and growing from the wound bed and/or (b) releasing them to be attacked by the body in the wound. It may aid in the debridement of slough, eschar and necrotic tissue growth from the wound, and in preventing adhesion of wound tissue to the dressing.

Examples of suitable ways in which flow stress can be achieved include applying (a) an optionally varying and/or reversing linear flow and/or (b) a relatively high rate of irrigant flow across the area of the wound bed. That is, flow stress across the wound may be provided by means of (a) a linear flow of irrigant across the wound bed, (b) a relatively high rate of irrigant flow across the wound bed, or (c) a combination of the two.

Generally simultaneous irrigate/aspirate systems lead themselves to including flow stress as fluid can be induced to flow between an inlet and outlet as required (this is described in more detail below). However, sequential systems are also suitable for inducing flow stresses. In particular these stresses may be induced during the filling and emptying cycles.

When used herein, the term 'linear' refers to flow that is locally linear on a cellular scale, and thus includes not only parallel flow, but also radial streaming, and spiral, helical, spirohelical and circular streaming. Preferred linear flows include radial streaming from the center out and from the periphery in to center, in particular from the periphery in to the center as this may increase the cell motility velocity of keratinocytes towards the center, and so promote re-epithelialisation. It is also preferred that the flow rate is relatively uniform across the wound to achieve a uniform stimulation applied across the wound bed.

The velocity of the fluid thereover may be constant, but it may be varied, preferably cyclically, either randomly or regularly. Usually the direction of the wound irrigant and/or wound exudate is held constant, but the flow rate may be varied positively and negatively, preferably cyclically, and either randomly or regularly.

Cyclical application of flow stress across the wound bed may result in a further increase in cell proliferation and in the breaking strength of tissue growth, and in a strong three-dimensional structure of tissue adhering well to and growing from the wound bed.

The stimulation of the healing of wounds may also be effected by regularly or randomly pulsing a flow velocity applied to the wound at any appropriate point for this purpose. The frequencies of such pulsed flow stressing across the wound will be (a) substantially higher than those of the cycles of flow velocity to the wound bed for the stimulation of the healing of wounds referred to above, but (b) less (generally substantially less) than the frequencies of ultrasound that may be used on the wound bed in alternative methods of therapy. Pulsing the flow over the wound may advantageously also provide a means to over-ride pain, similar to TENS.

Stimulus to the wound bed by applying an optionally varying flow velocity (i.e. cyclical) and agitation of the wound bed to stimulate the cells by regularly or randomly pulsing any flow applied to the wound are mutually compatible. They may, as appropriate, be applied alone or together. Flow may be applied continually or in periodic episodes between which the apparatus is operating in lower flow regimes, or indeed where the apparatus is working on a sequential (fill/empty) basis.

Thus, an embodiment of the apparatus for irrigating, flow stressing and/or cleansing wounds is characterised in that it comprises means for supplying optionally varying linear flow velocity, which is optionally pulsed, to a wound bed for the stimulation of the healing of the wound. Examples of suitable linear velocities are up to 0.03 m/s in a 100 micrometre gap or channel between wound bed and dressing creating a shear stress on the wound bed of the order of 12-13 dynes/cm$^2$. In practice, such a velocity will be of the order of 0.06 to 6, e.g. 0.2 to 2, for example 0.6 mm/s in a 100 micrometer channel between wound bed and dressing creating a shear stress on the wound bed of the order of 0.06 to 20, e.g. 0.6 to 6, for example 0.6-2 dynes/cm$^2$, for a typical wound exudate and/or isotonic saline irrigant. By way of example, a fluid velocity of e.g. 0.3 m/s will typically be a flow rate of 70-200 ml/hr for a 100 mm diameter wound.

It will be appreciated that the shear stress (and consequentially flow stress) on the wound bed will increase with the viscosity of the fluid passing across it. This property may be used to increase or decrease the flow stress generated by a given flow velocity.

Another embodiment of the apparatus for irrigating, flow stressing and/or cleansing wounds is characterised in that it comprises means for supplying optionally varying relatively high flow velocity, which is optionally pulsed, to a wound bed for the stimulation of the healing of the wound.

As noted hereinbefore, in certain embodiments of the present invention, the flow velocity of the fluid may be constant, but may be varied, preferably cyclically, either randomly or regularly. In both embodiments:

Examples of suitable frequencies of such regular cycles of flow velocities for the stimulation of the healing of wounds include 1 to 48 per 24 hr.

Examples of preferred frequencies of such regular cycles of flow velocities for the stimulation of the healing of wounds include 12 to 24 per 24 hr, e.g. 2 to 1 per hr.

Examples of suitable waveforms of such cycles either regularly or randomly for the stimulation of the healing of wounds include curved, e.g. sinusoidal, and sawtooth for higher frequencies, and usually square for lower frequencies.

Examples of means for applying flow stress to the wound bed include supplying irrigant to, and letting out irrigant and/or wound exudate from, the wound dressing in regular or random cycles and/or pulsed either regularly or randomly.

Examples of suitable frequencies of such regular pulses for the stimulation of the healing of wounds include 1 to 60 per min, e.g. 5 to 10 per min.

Examples of preferred frequencies of such regular pulses for the stimulation of the healing of wounds include 30 to 60 per min, e.g. 10 to 20 per min.

Examples of suitable waveforms of such pulses either regularly or randomly for the stimulation of the healing of wounds include curved, e.g. sinusoidal, sawtooth, square and a systolic-diastolic asymmetric sawtooth.

Examples of means for applying an optionally varying linear flow velocity at any appropriate point for flow stressing the wound include a wound dressing as hereinbefore described defined that comprises one or more modules capable of imposing linear flow on the irrigant at any appropriate point across the wound bed.

Thus, one favoured embodiment of the apparatus for irrigating, stressing and/or cleansing wounds is characterised in that it comprises a wound dressing as hereinbefore defined that comprises one or more modules capable of imposing linear flow on the irrigant across the wound bed at any appropriate point for flow stressing the wound.

Examples of suitable modules capable of imposing linear flow on the irrigant across the wound bed at any appropriate point for stressing the wound include the following in conjunction with a wound-facing face of the dressing that is in contact with or very close to the wound bed.

A plurality of inlet and/or outlet pipes maybe disposed in an array under the wound-facing face of the dressing, so as to allow passage of irrigant and/or wound exudate through the wound to take place in a controllable linear stream.

Irrigant inlet and/or outlet manifolds with respectively a plurality of inlet and/or outlet apertures, and connected in turn to at least one irrigant inlet pipe(s) and/or outlet pipe(s) may be provided under the wound-facing face of the wound dressing. (Fluid passes between these structures and they assist in channelling flow of irrigant and/or wound exudate through the wound in a controllable stream.) These may, for example, include tubules in an array connecting into a manifold.

Projections, such as bulges or protuberances, may be provided on the wound-facing face of the dressing. Alternatively or additionally, where appropriate depressions may be provided on the wound-facing face of the dressing. Both will often run within the wound between the inlet pipe(s) and the outlet pipe(s) (or manifolds) under the wound-facing face of the wound dressing. Fluid-inflatable bodies that lie in the wound in use and form projections are described hereinafter in greater detail. Of particular interest are fluid-inflatable irrigant inlet manifolds comprised in the dressing, which are inflated by admitting irrigant fluid. Examples of preferred such modules include fluid-inflatable irrigant inlet manifolds comprised in the dressing as described hereinafter in greater detail. The modules and backing layer may be completely separate integers, separate integers which are attached, for example by heat sealing, to each other, or they may be integral, i.e. may be formed of a single piece of material. In all cases the modules may be disposed to impose linear flow between the inlet pipe(s) (or manifold) and the outlet pipe(s) (or manifold) under the wound-facing face of the wound dressing, as hereinbefore describe, in a number of different modes.

Examples of forms of linear flow imposed on the irrigant across the wound bed at any appropriate point for stressing the wound include not only parallel flow, but also radial streaming, and spiral, helical, spirohelical and circular streaming. Preferred linear flows include radial streaming. Preferred linear flows include radial streaming from the center out and from the periphery in to center, in particular from the periphery in to the center as this may increase the cell motility velocity of keratinocytes towards the center, and so promote re-epithelialisation.

Thus, the modules may comprise a plurality of inlet and/or outlet pipes (or manifold(s)) disposed in an array under the wound-facing face of the dressing, so as to allow passage of irrigant and/or wound exudate through the wound to take place in a controllable linear stream.

Two arrays of inlet pipe(s) and/or outlet pipe(s) (or manifold(s)) under the wound-facing face of the wound dressing may be aligned parallel to each other, opposing each other diametrically across the wound, so that when fluid passes between these structures they assist in channelling flow of irrigant and/or wound exudate across the wound in a parallel stream.

Preferably, a plurality of inlet pipe(s) or outlet pipe(s) (or manifold(s)) is disposed to surround respectively one or more centrally disposed outlet or inlet pipes. (These may be at the geometric center of the backing layer of the wound dressing as hereinbefore defined, rather than generally centrally disposed therein.) The purpose is to allow passage of irrigant and/or wound exudate through the wound to take place in a controllable radial stream. Such a stream applies flow stress radially across the wound bed.

The plurality of inlet and/or outlet pores or apertures respectively in irrigant inlet and/or outlet manifolds, connected in turn to at least one irrigant inlet pipe(s) and/or outlet pipe(s) under the wound dressing can be considered as equivalent to the above plurality of inlet pipe(s) or outlet pipe(s). Again, the purpose is to allow passage of irrigant and/or wound exudate through the wound to take place in a controllable linear stream.

As above, such irrigant inlet and/or outlet manifolds may be aligned parallel to each other, opposing each other diametrically across the wound, so that when fluid passes between these structures they assist in channelling flow of irrigant and/or wound exudate across the wound in a parallel stream. Alternatively they may be arranged in a concentric arrangement or similar wherein an inlet/outlet manifold surrounds a corresponding inlet/outlet manifold.

Preferably, an irrigant inlet and/or outlet manifold with respectively a plurality of inlet and/or outlet apertures is disposed to surround respectively at least one more-centrally disposed outlet or inlet pipes. (These may be at the geometric center of the backing layer of the wound dressing as hereinbefore defined, rather than generally centrally disposed therein.)

Preferably, an irrigant outlet and/or inlet manifold with respectively a plurality of inlet and/or outlet pores or apertures is connected respectively to the at least one more-centrally disposed outlet or inlet pipes.

The purpose in both cases is to allow passage of irrigant and/or wound exudate through the wound to take place in a controllable radial stream. As above, such a stream applies flow stress radially across the wound bed. As noted above, such irrigant inlet manifolds may be fluid-inflatable bodies that lie in the wound in use and form projections, as described hereinafter in greater detail. These are inflated by admitting irrigant fluid, and they assist in channelling flow of irrigant and/or wound exudate through the wound.

In such cases of radial streaming, the surrounding apertures could be at or near the periphery of the wound-facing face of the dressing, and the more-centrally disposed apertures could be at or near the center. However, each are often disposed regularly or irregularly across the dressing, in the manner of a shower-head, and they are preferably disposed regularly across it, as this favours a constant flow rate over all parts of the wound bed.

Thus, according to another embodiment of the present invention there is provided an apparatus for irrigating and/or cleansing wounds, characterised in that it comprises a conformable wound dressing as hereinbefore defined having at least one (and preferably a plurality) of inlet or outlet apertures more-centrally disposed therein and a plurality of respectively outlet or inlet apertures disposed to surround the more-centrally disposed apertures.

The apertures may include the outlets of tubules of an array connecting into a manifold. More usually, however, in embodiments comprising such manifolds, they are formed of porous film or microporous membrane. The apertures or pores by the wound bed are preferably distributed evenly over the underside of the dressing and/or over the wound bed in use. To achieve a relatively high flow rate, and depending on the appropriate or desired flow rate, of the moving fluid over the wound bed, the apertures or pores by the wound bed may suitably form of the order of 0.5 to 30% of the area of the wound-facing face of the dressing by the wound bed, such as 0.7 to 10%, e.g. 0.9 to 3%, for example about 1%. They may have an average cross-dimension of 1 to 1000 µm, such as 3 to 300 µm, e.g. 5 to 100 µm, for example 6 to 60 µm.

To the same end, in certain embodiments of the present invention, the pressure differential across the porous film or microporous membrane with the apertures or pores by the wound bed on the underside of the dressing in use may suitably be of the order of 1 to 500 mmHg, such as 3 to 250 mmHg, e.g. 10 to 125 mmHg, for example about 80 mmHg.

Alternatively or additionally, where appropriate there may be projections, such as bulges or protuberances, and/or where appropriate depressions, effectively on the wound-facing face of the dressing. Both will often run within the wound between the inlet pipe(s) and the outlet pipe(s) under the wound-facing face of the wound dressing. (Fluid passes between these structures and they assist in channelling flow of irrigant and/or wound exudate through the wound in a controllable stream.)

The projections may have a significantly three-dimensional structure, such as points, bosses, ribs and ridges. Such bosses may be circular, elliptical or polygonal in plan view, such as triangular, rectangular or hexagonal. These may be may be, e.g. an integral net with elongate apertures e.g. formed by fibrillation of an embossed film, sheet or membrane of a polymeric material or by casting the material. These are preferably projections in a substantially radiating array under the wound-facing face of the wound dressing. The projections may be disposed regularly or irregularly across the dressing, although they are often disposed regularly across it.

Again, the depressions may have a significantly three-dimensional structure, such as grooves, channels or conduits. The structures are preferably in a substantially radial array. Suitably, these may be formed by embossing a sheet, film or membrane. It will be apparent that any features of inflation of the wound facing face of the dressing may be used to help direct or guide fluid flow to provide linear flow. Fluid-inflatable bodies that lie in the wound in use may form such projections, in particular such inlet manifolds, as described hereinafter in greater detail. These are inflated by admitting irrigant fluid, and they assist in channelling flow of irrigant and/or wound exudate through the wound in a controllable stream. As noted above, they may be formed of porous film or microporous membrane. The inflated manifolds may have a significantly three-dimensional structure, such as points, bosses, ribs and ridges. Such bosses may be circular, elliptical or polygonal in plan view, such as triangular, rectangular or hexagonal. The backing layer and modules may be of the same or different materials, but each should be of a material that does not absorb aqueous fluids such as water, blood, wound exudate, etc. and is soft and resiliently deformable.

According to another embodiment of the present invention there is provided a apparatus for irrigating and/or cleansing wounds, characterised in that it comprises a conformable wound dressing as hereinbefore defined having projecting or depressed structures disposed between the inlet pipe(s) and the outlet pipe(s) under the wound-facing face of the wound dressing.

In the embodiment of the apparatus that is characterised in that it comprises means for supplying optionally varying flow velocity, which is optionally pulsed, to a wound bed for the stimulation of the healing of the wound, the relatively high flow rates are typically provided by the device for moving fluid through the wound.

The type and/or capacity of a suitable device for moving fluid through the wound at the desired velocity will be largely determined by the appropriate or desired fluid flow rate and the flow resistance of the flow path. Suitable devices are indicated below.

As noted hereinbefore, in certain embodiments of the present invention, the flow velocity of the fluid may be constant, but may be varied, preferably cyclically, either randomly or regularly. To achieve this, the present apparatus additionally, where appropriate, comprises a system which can regulate the pump output to the wound bed under the wound dressing. Preferably such a system is a conventional automated, programmable system which can maintain the wound at or near an appropriate, desired flow stress to the wound bed and regularly or randomly pulse a flow velocity applied to the wound at any appropriate point for this purpose. Such pulsed flow across the wound may be provided by some types of the device for moving fluid through the wound.

Certain diaphragm pumps described hereinafter in greater detail will be appropriate for this purpose, as are peristaltic pumps, an electrically pulsable valve on the fluid reservoir, and an electromechanical oscillator directly coupled to the wound dressing.

It will of course be apparent that the apparatus may comprise more than one of the means described above to induce flow stress. For example the apparatus may have means to vary fluid flow and means to improve linear flow in a desired form.

Pressure Regulation

In relevant embodiments of the present apparatus for aspirating, irrigating and/or cleansing wounds, it is advantageous that it additionally, where appropriate, comprises a system which can regulate the pressure on the wound bed, under the wound dressing.

Preferably such a system is a conventional automated, programmable system which can maintain the wound at or near an appropriate, desired stress to the wound bed and optionally tissue surrounding the wound, to an appropriate, desired program while moving fluid over the wound bed at an appropriate, desired rate.

Examples of suitable means for the stimulation of the healing of wounds and tissue adhering well to and growing from the wound bed include applying mechanical stimulus to the wound bed and optionally tissue surrounding the wound via the wound dressing and/or via the fluid under dressing. Examples of suitable ways in which this can in turn be achieved include applying an optionally varying positive and/or negative pressure at any appropriate point for stressing the wound.

The amplitude of the positive and/or negative pressure on the wound bed and optionally tissue surrounding the wound and/or the fluid thereover may be constant, but more usually is varied, preferably cyclically, either randomly or regularly. Such cyclical variation of the pressure applied to the wound is effectively the application of an amplitude waveform at a desired frequency to apply a desired level of stress to the wound bed and optionally tissue surrounding the wound (it should be noted that application of a varying pressure may cause strain to the surface of the wound, i.e. deflection of the wound bed, but this is envisaged in the term stress as used herein).

The desired level and regime of stress to the wound bed and optionally tissue surrounding the wound may be applied conventionally by varying the positive and/or negative pressure applied to the wound bed, e.g. by (a) varying the rate of the means for moving fluid over the wound bed as appropriate or desired, e.g. the rate of any pump used to apply positive or negative pressure to the wound bed at any appropriate point for stressing the wound, (b) bleeding fluids, especially gases, such as air and nitrogen, but not excluding liquids, such as water and saline, or gas in liquid aerosols; and gels into the flowpath in any appropriate part of the apparatus to vary the pressure applied to the wound to a desired level and/or program, and/or (c) varying the pressure in any inflatable filler within the wound dressing as appropriate or desired, as described in more detail hereinafter. Preferably, such regular or random variation of the positive and/or negative pressure applied to the wound will be effected by conventional process control devices and/or software.

The stimulation of the healing of wounds in certain embodiments of the present invention may also be effected by agitation of the wound bed and/or creating intermittent flow and/or turbulence to stimulate the cells. This can be done preferably by regularly or randomly pulsing a positive and/or negative pressure applied to the wound at any appropriate point for this purpose. Such pulsed variation of the pressure applied to the wound is again effectively the application of an amplitude waveform at a desired frequency to apply a desired level of stress to the wound bed and optionally tissue surrounding the wound.

Pulsing the pressure on the wound may advantageously also provide a means to over-ride pain, similar to TENS. The range of variation of the pulsed positive and/or negative pressure applied to the wound will be substantially less than the maximum levels of pressure referred to below, i.e. less than 50% atm and typically significantly lower. The frequencies of such pulsed stressing across the wound will be substantially higher than those of the cycles of positive and/or negative pressure to the wound bed and optionally tissue surrounding the wound for the stimulation of the healing of wounds referred to above.

The range of variation of the pulsed positive and/or negative pressure applied to the wound will generally be substantially less than the maximum levels of pressure and than the range of variation in the levels of pressure referred to below in respect of cycles of positive and/or negative pressure.

To clarify there are two forms of stress generally envisaged as being useful, i.e. those achieved by a slow cycling of pressure, and those achieved by a more rapid pulsing of pressures. The range of pressure in a "cycle" is typically significantly greater than that of a "pulse". An analogy is a carrier wave (the cycle) containing the pulse superimposed upon it.

Regularly or randomly pulsing any pressure applied to the wound may be effected essentially as described hereinbefore in connection with the variation of the positive and/or negative pressure applied to the wound. Again, such regular or random pulsing of the positive and/or negative pressure applied to the wound may be effected by conventional process control devices and/or software. Such pulsing of any pressure applied to the wound may be applied as an amplitude modulation of the positive and/or negative pressure applied to the wound bed and optionally tissue surrounding the wound, which in turn may be held constant, but more usually is varied, preferably cyclically, either randomly or regularly (i.e. the carrier wave referred to above may in fact be a constant positive or negative pressure), but this is generally less preferred.

Where the levels of such pressure above or below atmospheric are held constant, this is often achieved in the present apparatus, where appropriate, by use of a control device that can regulate the pressure in the wound dressing by bleeding fluids, especially gases, such as air and nitrogen, but not excluding liquids, such as water and saline, or gas in liquid aerosols; and gels into the flowpath in any appropriate part of the apparatus to vary the pressure applied to the wound to a desired level and/or program.

This often results in any device for moving fluid through the wound that is downstream of the dressing and that applies an overall negative pressure in the wound space, e.g. a vacuum pump, pumping a heterogeneous mixture of liquid wound exudate and irrigant from the wound dressing with bleed gases, such as air and nitrogen. This can result in pulsing of any pressure applied to the wound.

The pumping rate and the dimensions of the offtake and/or supply tubes may be adjusted to maintain the desired balance of pulsing pressure amplitude and frequencies on the wound. Preferably such a system is a conventional automated, programmable system which can maintain the appropriate pulse regimen to the wound. Stimulus to the wound bed and optionally tissue surrounding the wound by applying an optionally varying positive and/or negative pressure and agitation of the wound bed to stimulate the cells by regularly or randomly pulsing any pressure applied to the wound are mutually compatible. They may, as appropriate, be applied alone or together.

Thus, an embodiment of the apparatus for irrigating, stressing and/or cleansing wounds is characterised in that it comprises means for supplying optionally varying positive and/or negative pressure, which is optionally pulsed, to a wound bed and optionally tissue surrounding the wound for the stimulation of the healing of the wound.

As noted hereinbefore, in certain embodiments of the present invention, the positive and/or negative pressure on the wound bed and/or the fluid thereover and optionally tissue surrounding the wound may be constant, but more usually is varied, preferably cyclically, either randomly or regularly. Where the pressure on the wound bed and/or the fluid thereover and optionally tissue surrounding is varied, it may be a varying positive or negative pressure, or it may as appropriate vary from positive to negative or vice versa, again preferably cyclically, and either randomly or regularly. It may vary about a constant positive or negative baseline pressure, or less usually about a varying baseline pressure. Examples of maximum levels of such pressure above and below atmospheric include 50% atm. e.g. between 5 and 40% atm., e.g. between 15 and 35% atm.

Examples of suitable frequencies of such regular cycles of pressure for the stimulation of the healing of wounds include 1 to 48 per 24 hr, such as 12 to 24 per 24 hr, e.g. 2 to 1 per hr.

Examples of suitable waveforms of such cycles either regularly or randomly for the stimulation of the healing of wounds include curved, e.g. sinusoidal, random white noise and sawtooth for higher frequencies, and usually square for lower frequencies.

Examples of suitable frequencies of regular pulses for the stimulation of the healing of wounds include 1 to 3000 per min (0.016-50 Hz), e.g. 30 to 60 per min, e.g. 3 to 20 per min, i.e. 0.05 to 0.33 Hz, such as 5 to 10 per min.

Such pulses may be varying positive or negative pressure pulses, or they may as appropriate vary from positive to negative or vice versa, again preferably cyclically, and either randomly or regularly. They may vary about a constant positive or negative baseline pressure or about a varying baseline pressure. Examples of maximum amplitudes for such pulses are up to 10 mm Hg above and below the constant positive or negative baseline pressure, e.g up to 7 mm Hg or up to 3 mm Hg. Examples of suitable waveforms of such pulses either regularly or randomly for the stimulation of the healing of wounds include curved, e.g. sinusoidal, random white noise sawtooth, square and a systolic-diastolic asymmetric sawtooth.

Where the amplitude of regular cycles of pressure is modulated by superimposed regular pulses for the stimulation of the healing of wounds, examples of suitable frequencies of the combination include those where the carrier frequency is 1 to 48 per 24 hours and the superimposed frequency of the pressure pulses is 1 to 0.05 Hz, both with the respective amplitudes noted above. Examples of suitable waveforms of the cycles and the superimposed pulses may be regular or random and include curved, e.g. sinusoidal, random white noise, sawtooth, square and a systolic-diastolic asymmetric sawtooth.

Examples of means for applying an optionally varying positive and/or negative pressure at any appropriate point for stressing the wound and/or regularly or randomly pulsing any pressure applied to the wound for promoting wound healing, whether applied alone or together, include a wound dressing as hereinbefore defined that comprises one or more expandable and contractible modules capable of applying pressure to the wound bed and optionally tissue surrounding the wound at any appropriate point for stressing the wound.

Examples of other suitable means of applying mechanical stimulus to the wound by optionally varying positive and/or negative pressure include a magnetic fluid in a chamber or other hollow structure under the backing layer of the dressing in contact with the wound bed and/or the fluid thereover. A regularly or randomly (preferably cyclically) varying and/or pulsing external magnetic field is applied to the magnetic fluid. However, such means are generally less favoured.

Thus, one favoured embodiment of the apparatus for irrigating, stressing and/or cleansing wounds is characterised in that it comprises a wound dressing as hereinbefore defined that comprises one or more expandable and contractible modules. Such a module is capable of applying pressure to the wound bed and optionally tissue surrounding the wound at any appropriate point for stressing the wound. It should be capable of maintaining the pressure on the wound bed and/or the fluid thereover and optionally tissue surrounding the wound at a constant level, but more usually it should be capable of regularly or randomly (preferably cyclically) varying and/or pulsing the pressure applied to the wound, all at or near an appropriate, desired level of stress to the wound bed and optionally tissue surrounding the wound, to an appropriate, desired program while moving fluid over the wound bed at an appropriate, desired rate.

Examples of suitable modules capable of applying pressure to the wound bed at any appropriate point for stressing the wound include a module in the wound dressing may be made of a polymer that can be electrically stimulated to change shape repeatedly at appropriate frequencies. A preferred module is a fluid-inflatable body that lies in the wound in use.

Thus, one favoured embodiment of the apparatus for irrigating, stressing and/or cleansing wounds is characterised in that it comprises a wound dressing as hereinbefore defined that comprises one or more fluid-inflatable modules capable of applying pressure to the wound bed at any appropriate point for stressing the wound.

This is capable of maintaining the pressure on the wound bed and/or the fluid thereover at a constant level, but more usually it is also capable of regularly or randomly (preferably cyclically) varying and/or pulsing the pressure applied to the wound, all at or near an appropriate, desired level of stress to the wound bed, to an appropriate, desired program while moving fluid over the wound bed. The module or modules is/are (usually cyclically) inflated and deflated by admitting and releasing fluid. Once the inflatable body has been inflated, it may be deflated as appropriate or desired, and then reinflated to again apply a positive pressure to the wound, and the cycle may be repeated as appropriate or desired.

Alternatively, it may be partially filled with an elastically resilient material, such as an elastomeric foam, that in its rest state is capable of applying a working pressure to the wound bed. The body may then be deflated as appropriate or desired, and then reinflated under the action of its filler material to again apply a positive pressure to the wound, and the cycle may be repeated as appropriate or desired.

Examples of forms of the body that are suitable such expandable and contractible modules capable of applying pressure to the wound bed at any appropriate point for stressing the wound include fluid-inflatable fillers and fluid-inflatable irrigant inlet manifolds comprised in the dressing, as described hereinafter in greater detail. Where the module is a fluid-inflatable filler, examples of suitable fluids include gases, such as air and nitrogen; liquids, such as water and saline; gas in liquid aerosols; and gels such as those described in greater detail hereinafter. Preferred fluids include gases, such as air or nitrogen. Where the module is a fluid-inflatable irrigant inlet manifold comprised in the dressing as described hereinafter in greater detail, it will be stimulated to change shape as appropriate and optionally at desired frequencies by inflation with irrigant, followed as desired by deflation. Examples of both are included hereinafter.

Examples of such fillers include a substantially flat film, sheet or membrane, defining a chamber, pouch or other structure of the backing layer, e.g. of polymer film, which can contain the inflation fluid. It is provided with an inflation device for moving inflation fluid to the filler, and is connected to it by an inflation tube which communicates with its internal space. The inflation device may also serve as a deflation device for moving inflation fluid from the filler, and the inflation tube also serves as a deflation tube.

Alternatively or additionally, where appropriate the filler as hereinbefore defined may have a deflation pipe and a bleed valve to waste, e.g. to a collection bag if a non-gaseous fluid is used. The inflation device for moving inflation fluid then only serves as an inflation device to apply a positive pressure on the wound bed. Less usually, the filler may have an inflation device and a deflation device. Where it lies under the backing layer of the wound dressing of the apparatus, the inflation tube may run to the filler within the wound under the wound-facing face of the wound dressing.

However, the inflation tube may be connected to an inflation pipe that passes through the wound-facing face of the backing layer, the point at which the inflation pipe passes through the wound-facing face forming a relatively fluid-tight seal. The inflation pipe may be in the form of an aperture, such as a funnel hole, opening, orifice, luer, slot or port for connection as a female member respectively to a mating end of the inflation tube (optionally or as necessary via means for forming a tube, pipe or hose, or nozzle).

Where the pipe passes through, rather than under the backing layer, the backing layer may often have a rigid and/or resiliently inflexible or stiff area to resist any substantial play between the or each pipe and the or each mating tube, or deformation under pressure in any direction. It may often be stiffened, reinforced or otherwise strengthened by a boss projecting distally (outwardly from the wound) around each relevant tube, pipe or hose, or nozzle, hole, opening, orifice, luer, slot or port for connection to a mating end of the inflation tube. The components may be a push, snap or twist-lock fit with each other. The minimum calibre of the inflation tube and pipe should be sufficient for them to permit as rapid inflation and deflation of the filler as is desired. Suitably the range of cross-dimensions of the bore (i.e. calibre) may be 0.5 to 6 mm, e.g. 1.5 to 2 mm. Each should be resiliently flexible, and preferably soft with good conformability. This can be done for example by forming it of a suitable material, e.g. a resilient thermoplastic.

Examples of suitable inflation device for moving fluid into the filler include pumps. As noted above, the inflation device may also serve as a deflation device for moving inflation fluid from the filler, and the inflation tube also serves as a deflation tube. In such case, the pump should be a reversible pump used to increase and decrease the pressure on the wound bed as desired.

Subject to this consideration, the type and/or capacity of the device will also be largely determined by (a) the appropriate or desired positive or negative pressure to the wound bed, (b) the nature of the fluid, i.e. whether it is a gas, such as air and nitrogen; a liquid, such as water and saline; a gas in liquid aerosol; or a gel; (c) the desired frequencies and waveforms of such cycles either regularly or randomly.

The following types of pump may be used to apply positive pressure, as desired to the filler through an inflation tube which communicates with its internal space: (a) Reciprocating Pumps, such as: (i) Syringe or piston pumps—providing high pressure and high accuracy; (ii) Diaphragm pumps—where pulsations of one or two flexible diaphragms displace liquid while check valves control the direction of the fluid flow e.g. preferably a small portable diaphragm pump; and (b) Rotary pumps, such as: (i) Centrifugal pumps—with rotating vaned disk attached to a drive shaft moving fluid without pulsation as it spins. The outlet can be restricted without damaging the pump; (ii) Peristaltic pumps—with rollers on a rotor acting on fluid in a tube, e.g. preferably a small portable peristaltic pump.

Of these, only piston pumps and rotary pumps, such as centrifugal pumps and peristaltic pumps are readily reversible pumps that may be used to increase and decrease the pressure on the wound bed as desired. Subject to this consideration, preferred reversible pumps include a small portable peristaltic pump.

Preferred non-reversible pumps to be used with a bleed valve to the filler then include a small portable syringe pump (which is often used once and then disposed of) or small portable diaphragm pump, e.g. a sphygmometric pump.

Where the module is a fluid-inflatable irrigant inlet manifold comprised in the dressing as described herein after in greater detail, it will be stimulated to change shape as appropriate and optionally at desired frequencies by inflation with irrigant, followed as desired by partial deflation. It should be noted that the use of such a system is more suited to a simultaneous system but could be applied to a sequential (i.e. fill/empty cycle) system. When the manifold is inflated it will influence the pressure applied to the surface of the wound, and when deflated the pressure will be reduced (i.e. relative to the baseline of the system).

The device for moving fluid through the wound is used to move irrigant to inflate the inlet manifold and apply a positive pressure to the wound bed. As noted hereinafter, the device may suitably be a pump. As noted hereinbefore, the pressure on the wound bed may be constant, but may be varied, preferably cyclically, either randomly or regularly. To achieve this, the present apparatus, where appropriate, comprises a system that can regulate the pump output to the inlet manifold in the wound dressing. Preferably such a system is a conventional automated, programmable system which can maintain the wound at or near an appropriate, desired flow stress to the wound bed to an appropriate, desired program while moving fluid over the wound bed.

As noted hereinbefore, stimulation of the healing of wounds in certain embodiments of the present invention may also be effected by regularly or randomly pulsing a pressure applied to the wound at any appropriate point for this purpose. Such pulsed flow across the wound may be provided by some types of the device for moving fluid through the wound. Certain diaphragm pumps described hereinafter in greater detail will be appropriate for this purpose, as are certain peristaltic pumps, and an electromechanical oscillator directly coupled to the wound dressing, would also be suitable.

Suitable materials for such modules (i.e. fillers, manifolds etc) of any type include synthetic polymeric materials that do not absorb aqueous fluids, such as polyolefins, polysiloxanes and polyesters. They may be hydrophilic, and thus also include hydrophilic polyurethanes. They also include thermoplastic elastomers and elastomer blends, for example copolymers, such as ethyl vinyl acetate polystyrene and elastomeric polyurethane formed by solution casting.

Operation of a Typical Apparatus

The operation of a typical apparatus of this type for simultaneous aspiration and irrigation of a wound at a low negative pressure of up to 20% atm., more usually up to 10% atm. at the wound, with one pump may involve the following steps. As mentioned previously, the application of negative pressure has beneficial effects in wound healing.

Before starting the apparatus for aspirating, irrigating and/or cleansing wounds, the backing layer of the wound dressing is applied over the wound and conformed to the shape of the bodily part in which the wound is to form a relatively fluid-tight seal or closure.

The means for supply flow regulation, connected to a fluid supply tube, such as a regulator, such as a rotary valve, is usually closed, and the means for aspirate flow regulation (if any), connected to a fluid offtake tube, is opened.

The aspiration pump is started and run to give a negative pressure of up to 50% atm., more usually up to 20% atm., e.g. up to 10% atm. to be applied applies a vacuum to the interior of the dressing and the wound.

The irrigation pump flow rate and any means for fluid supply regulation are then adjusted, and/or where the aspiration pump and/or the irrigation pump is a variable-speed pump, downstream of the wound dressing, either or both is/are adjusted, to maintain the desired balance of fluid at a controlled nominal flow rate and to maintain the desired negative pressure in the interior of the wound dressing.

Optionally, the means for applying flow stress may then be activated. Suitable forms of means for applying flow stress are set out above. The means for applying flow stress may be used to apply flow stress constantly or periodically, depending on the desired treatment regime.

Alternatively or additionally, the means of applying stress may then optionally be activated. Typically the means for applying stress comprises at least one expandable or contractible module capable of applying pressure to the wound bed. In one embodiment such a module comprises an inflatable body which lies within the wound in use. The inflatable body may be used to apply a constant pressure (and hence stress) to the wound or, preferably, may be used to apply a cyclical pressure. The module may be inflated and deflated be introducing and removing fluid to the body. Further details of suitable modules and their operation are given above.

The apparatus is then run for the desired length of therapy and with the desired negative pressure and stress regime. After this period, the aspiration pump is stopped.

In one embodiment, the means for supplying physiologically active materials to the wound is activated at such time as may be appropriate.

In one embodiment, the means for supplying thermal energy to the fluid in the wound in the present apparatus is activated at such time as may be appropriate. This is often once the pump is running, and the means for supply flow regulation is opened.

(These means for supplying thermal energy to the fluid in the wound in the present apparatus include a heater and/or conductively heated component of the apparatus flow path upstream of any outlet pipe(s) that pass through and/or under the wound-facing face of the backing layer of the wound dressing, which may supply conducted thermal energy, electromagnetic radiation of an appropriate wavelength, or (less often) convected thermal energy.)

The operation of a typical apparatus for simultaneous aspiration and irrigation of a wound at a low negative pressure of up to 20% atm., more usually up to 10% atm. at the wound, with two pumps may involve the following steps.

The necessary changes where the mode of operation is at a net positive pressure of e.g. up to 15% atm., more usually up to 10% atm. at the wound will be apparent to the skilled person.

Such a typical apparatus for simultaneous aspiration and irrigation of a wound at a low negative pressure of up to 20% atm., more usually up to 10% atm. at the wound comprises means for providing simultaneous aspiration and irrigation of the wound which is a combination of (a) a first device for moving fluid through the wound applied to the aspirate in the fluid offtake tube downstream of and away from the wound dressing, with optional means for aspirate flow regulation, connected to a fluid offtake tube: and (b) a second device for moving fluid through the wound applied to the irrigant in the fluid supply tube upstream of and towards the wound dressing, with optional means for supply flow regulation, connected to a fluid supply tube.

As noted above, either device may be (a) a fixed-throughput device, such as a fixed-speed pump, which will usually require a discrete means for aspirate flow regulation, connected to a fluid offtake tube, e.g. a regulator, such as a rotary valve, or for irrigant flow regulation, connected to a fluid supply tube, either e.g. a regulator, such as a rotary valve, or (b) a variable-throughput device, such as a variable-speed pump, thus effectively forming a combination of a device for moving fluid through the wound with means for flow regulation in a single integer.

As noted above, the apparatus may be (a) a single device for moving fluid through the wound applied to the aspirate in the fluid offtake tube downstream of and away from the wound dressing, in combination with (b) means for supply flow regulation, connected to a fluid supply tube, and (c) means for aspirate flow regulation, connected to a fluid offtake tube.

Before starting the apparatus for aspirating, irrigating and/or cleansing wounds, the backing layer of the wound dressing is applied over the wound and conformed to the shape of the bodily part in which the wound is to form a relatively fluid-tight seal or closure.

Any means for supply flow regulation, connected to a fluid supply tube, such as a regulator, such as a rotary valve, is usually closed, and any means for aspirate flow regulation, connected to a fluid offtake tube, is opened.

The aspiration pump is started and run to apply a negative pressure of up to 50% atm., more usually up to 20% atm., e.g. up to 10% atm., to the interior of the dressing and the wound.

The irrigation pump is then started, so that both pumps are running together, and any means for supply flow regulation is opened.

The irrigation pump flow rate and any means for fluid supply regulation are then adjusted and/or where the aspiration pump and/or the irrigation pump is a variable-speed pump, either or both is/are is adjusted, to maintain the desired balance of fluid at a controlled nominal flow rate and to maintain the desired negative pressure in the interior of the wound dressing.

Optionally, the means for applying stress may then be activated, as described above.

In one embodiment, the means for supplying physiologically active materials to the wound is activated at such time as may be appropriate.

Alternatively or additionally, the means for supplying thermal energy to the fluid in the wound in the present apparatus is optionally activated at such time as may be appropriate.

This is often once the pump is running, and the means for supply flow regulation is opened.

(These means for supplying thermal energy to the fluid in the wound in the present apparatus may include a heater and/or conductively heated component of the apparatus flow path upstream of any outlet pipe(s) that pass through and/or under the wound-facing face of the backing layer of the wound dressing, which may supply conducted thermal energy, electromagnetic radiation of an appropriate wavelength, or (less often) convected thermal energy.)

BRIEF DESCRIPTION OF THE DRAWINGS

The present invention will now be described by way of example only with reference to the accompanying drawings in which, in pertinent schematics, the means for applying stress to the wound bed is omitted for clarity. Additionally, the means for supplying conducted thermal energy which acts on the irrigant fluid in the flowpath upstream of the wound dressing in the fluid supply tube from the irrigant fluid reservoir as close to the wound dressing backing layer as possible is omitted from pertinent schematics for clarity.

FIG. 1 is a schematic view of an apparatus for aspirating, irrigating, and/or cleansing a wound according to embodiments of the present invention that have a single device for moving fluid through the wound applied to the aspirate in the fluid offtake tube downstream of and away from the wound dressing, in combination with means for supply flow regulation, connected to a fluid supply tube, and means for aspirate flow regulation, connected to a fluid offtake tube.

FIGS. 3 to 7 are cross-sectional views of conformable wound dressings, of certain embodiments of the present invention for aspirating and/or irrigating wounds. In these.

FIGS. 8 to 10 are various views of inlet and outlet manifold layouts for the wound dressings of certain embodiments of the present invention for respectively delivering fluid to, and collecting fluid from, the wound.

DETAILED DESCRIPTION OF THE EMBODIMENTS

Figure 2:
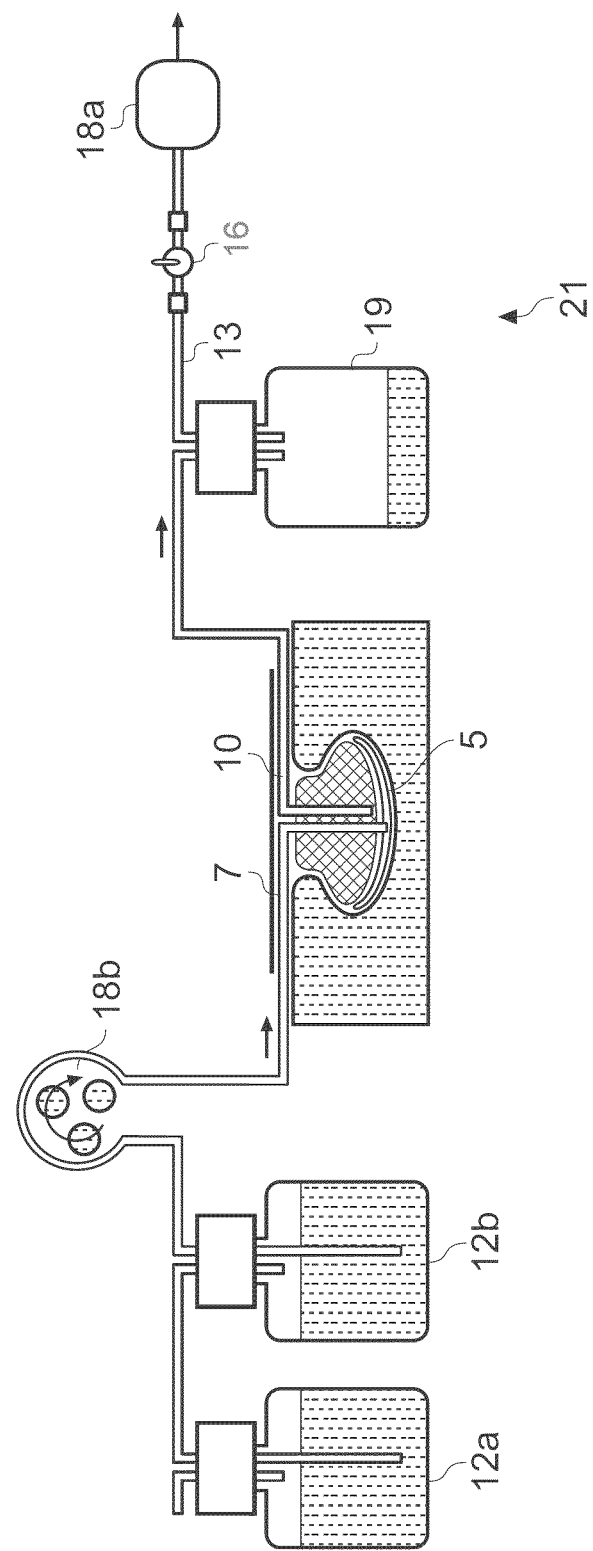
FIG. 2 is a schematic view of another apparatus for aspirating, irrigating, and/or cleansing a wound according to the one embodiment of the present invention that has a first device for moving fluid through the wound applied to the aspirate in the fluid offtake tube downstream of and away from the wound dressing, with means for aspirate flow regulation, connected to a fluid offtake tube; and a second device for moving fluid through the wound applied to the irrigant in the fluid supply tube upstream of and towards the wound dressing.

In all of the Figures, whether showing a schematic view of an apparatus for aspirating, irrigating and/or cleansing a wound according to a first aspect of the invention, or a view of conformable wound dressings of a second aspect of the present invention, a biodegradable scaffold may, in certain embodiments, be located under the wound dressing in use in contact with and conforming to the wound bed. It is omitted throughout for clarity.

Additionally, in all of the Figures, the integers (12A), the means for supplying physiologically active agents from cells or tissue to the wound, and (12B), a container that contains a cell or tissue component, may, in alternative embodiments, be replaced by a single fluid reservoir (12).

Referring to FIG. 1, the apparatus (1) for aspirating, irrigating, and/or cleansing wounds comprises a conformable wound dressing (2), having a backing layer (3) which is capable of forming a relatively fluid-tight seal or closure (4) over a wound (5) and one inlet pipe (6) for connection to a fluid supply tube (7), which passes through the wound-facing face of the backing layer (3) at (8), and one outlet pipe (9) for connection to a fluid offtake tube (10), which passes through the backing layer (3) at (11), the points (8), (11) at which the inlet pipe and the outlet pipe passes through and/or under the backing layer (3) forming a relatively fluid-tight seal or closure over the wound; the inlet pipe being connected via means for supply flow regulation, here a valve (14), by the fluid supply tube (7) to means for supplying physiologically active agents from cells or tissue to the wound, here a fluid reservoir (12a), and in one optional embodiment a container that contains a cell or tissue component (12b) connected to the supply tube (7), and the outlet pipe (9) being connected via means for aspirate flow regulation, here a valve (16) and a fluid offtake tube (10) to waste, e.g. to a collection bag (not shown); a device for moving fluid through the wound (5), here a diaphragm pump (18), e.g. preferably a small portable diaphragm pump, acting on the fluid offtake tube (10) to apply a low negative pressure on the wound; and the valve (14) in the fluid supply tube (7), the valve (16) in the aspiration tube (13), and the diaphragm pump (18), providing means for providing simultaneous aspiration and irrigation of the wound (5), such that fluid may be supplied to fill the flowpath from the fluid reservoir via the container that contains the cell or tissue component, in turn connected to a supply tube, fluid supply tube (via the means for supply flow regulation) and moved by the device through the flow path.

The operation of the apparatus is as described hereinbefore. In use, the inlet pipe, means for supply flow regulation, here valve (14), the fluid supply tube (7) and the container for cells or tissue (12b) may contain physiologically active components from the cells or tissue in therapeutically active amounts to promote wound healing, and adds such materials into the flowpath.

The supply of such physiologically active materials is here effected to the wound via the fluid passing through the wound dressing from irrigant in the container that contains the cells or tissue.

Referring to FIG. 2, the apparatus (21) is a variant two-pump system with essentially identical, and identically numbered, components as in FIG. 1, except that there is no means such as a valve for supply flow regulation in the fluid supply tube (7) from the fluid reservoir (12a), and a container that contains a cell or tissue component (12b) connected to the supply tube (7), and there is a first device for moving fluid through the wound (5), here a diaphragm pump (18a), e.g. preferably a small portable diaphragm pump, acting on the fluid aspiration tube (13) downstream of and away from the wound dressing to apply a low negative pressure on the wound; with means for negative pressure and/or aspirate flow regulation, here a valve (16) connected to the vacuum or fluid aspiration tube (13) and a vacuum vessel (aspirate collection jar) (19); and a second device for moving fluid through the wound (5), here a peristaltic pump (18b), e.g. preferably a small portable diaphragm or peristaltic pump, applied to the irrigant in the fluid supply tube (7) upstream of and towards the wound dressing, the first device (18a) and second device (18b), and the valve (16) in the vacuum or fluid aspiration tube (10), and the diaphragm pump (18a), providing means for providing simultaneous (or sequential) aspiration and irrigation of the wound (5), such that fluid may be supplied to fill the flowpath from the fluid reservoir via the fluid supply tube (via the means for supply flow regulation) and moved by the devices through the flow path.

The operation of the apparatus is as described hereinbefore.

Referring to FIGS. 3 to 6, each dressing is in the form of a conformable body defined by a microbe-impermeable film backing layer (42) with a uniform thickness of 25 micron. It has a wound-facing face, which is capable of forming a relatively fluid-tight seal or closure over a wound. The backing layer (42) extends in use on a wound over the skin around the wound.

On the proximal face of the backing layer (42) on the overlap, it bears an adhesive film (not shown), to attach it to the skin sufficiently to hold the wound dressing in place in a fluid-tight seal around the periphery of the backing layer (42) of the wound dressing.

There is one inlet pipe (46) for connection to a fluid supply tube (not shown), which passes through and/or under the backing layer (42), and one outlet pipe (47) for connection to a fluid offtake tube (not shown), which passes through and/or under the backing layer (42).

Figure 3A:
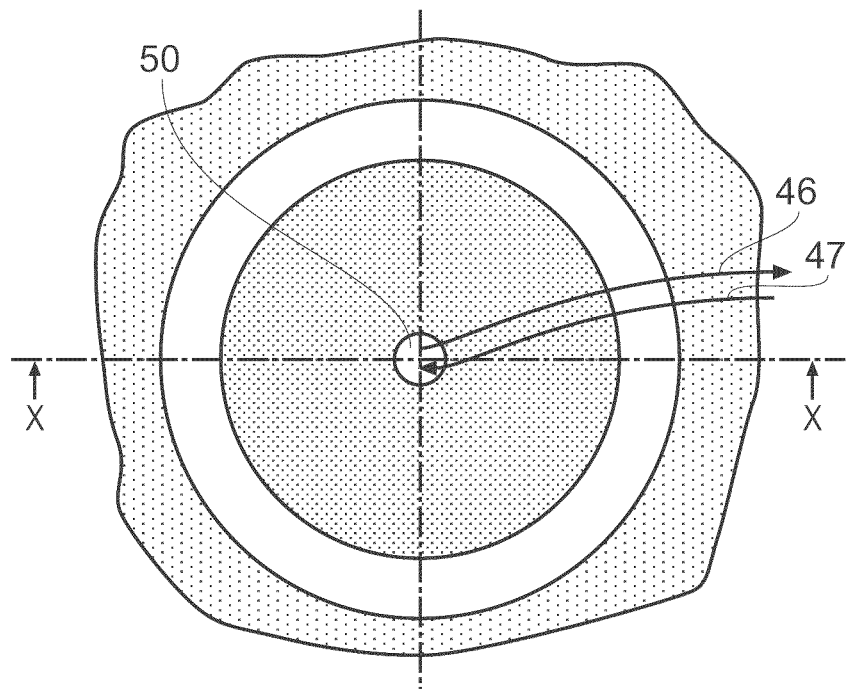
FIGS. 3a, 4a, 5a, 6a, and 7a are cross-sectional plan views of the wound dressings.
Figure 3B:
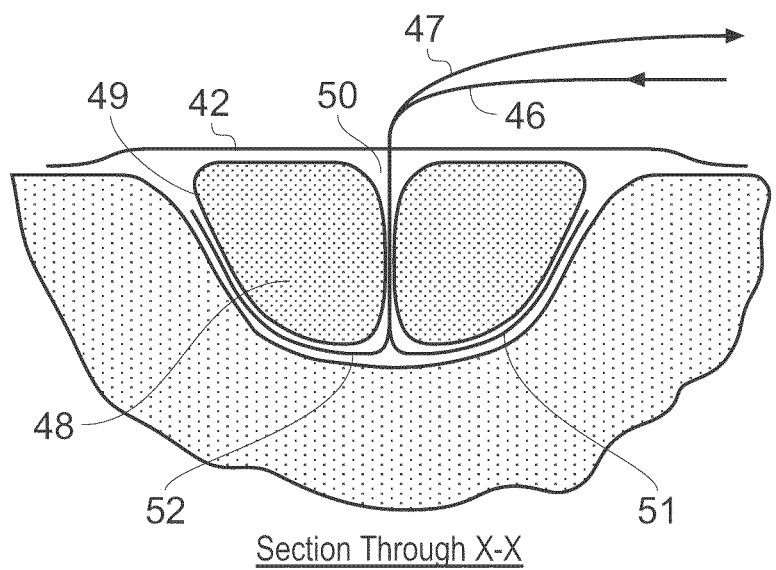
FIGS. 3b, 4b, 5b, 6b, and 7b are cross-sectional side views of the wound dressings.

Referring to FIGS. 3a and 3b, one form of the dressing is provided with a wound filler (48) under a circular backing layer (42). This comprises a generally frustroconical, toroidal conformable hollow body, defined by a membrane (49) which is filled with a fluid, here air or nitrogen, that urges it to the wound shape. The filler (48) may be permanently attached to the backing layer with an adhesive film (not shown) or by heat-sealing.

The inlet pipe (46) and outlet pipe (47) are mounted centrally in the backing layer (42) above the central tunnel (50) of the toroidal hollow body (48) and each passes through the backing layer (42). In other embodiments the inlet (46) and outlet (47) pipes may pass under the backing layer (42).

Each extends in pipes (51) and (52) respectively through the tunnel (50) of the toroidal hollow body (48) and then radially in diametrically opposite directions under the body (48).

This form of the dressing is a more suitable layout for deeper wounds.

Figure 4A:
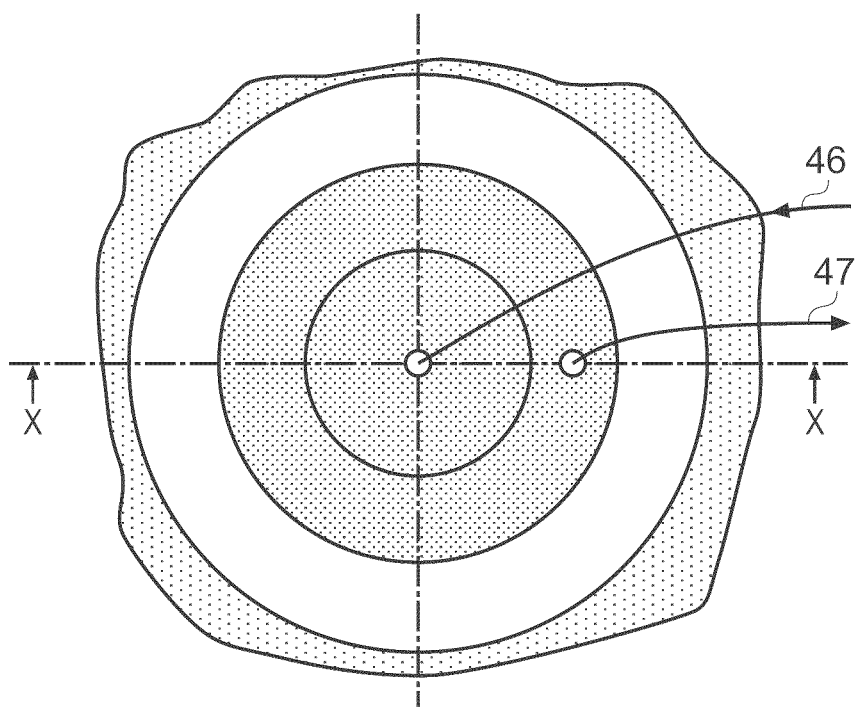
Figure 4B:
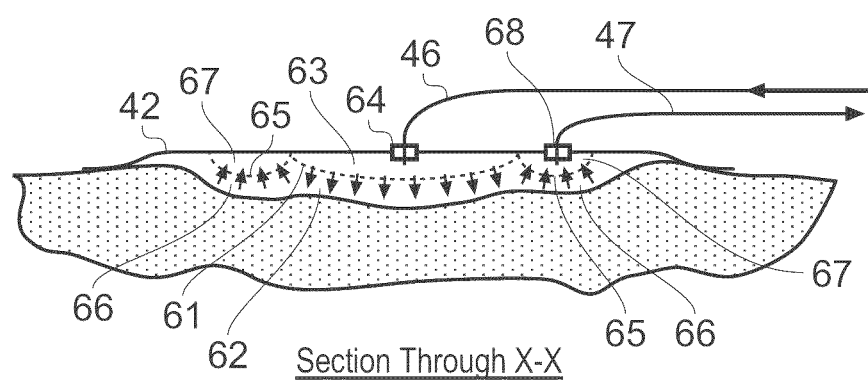

Referring to FIGS. 4a and 4b, a more suitable form for shallower wounds is shown.

This comprises a circular backing layer (42) and a circular upwardly dished first membrane (61) with apertures (62) that is permanently attached to the backing layer (42) by heat-sealing to form a circular pouch (63).

The pouch (63) communicates with the inlet pipe (46) through a hole (64), and thus effectively forms an inlet pipe manifold that delivers the circulating or aspirating fluid directly to the wound when the dressing is in use.

An annular second membrane (65) with openings (66) is permanently attached to the backing layer (42) by heat-sealing to form an annular chamber (67) with the layer (42).

The chamber (67) communicates with the outlet pipe (47) through an orifice (68), and thus effectively forms an outlet pipe manifold that collects the fluid directly from the wound when the dressing is in use.

Figure 5A:
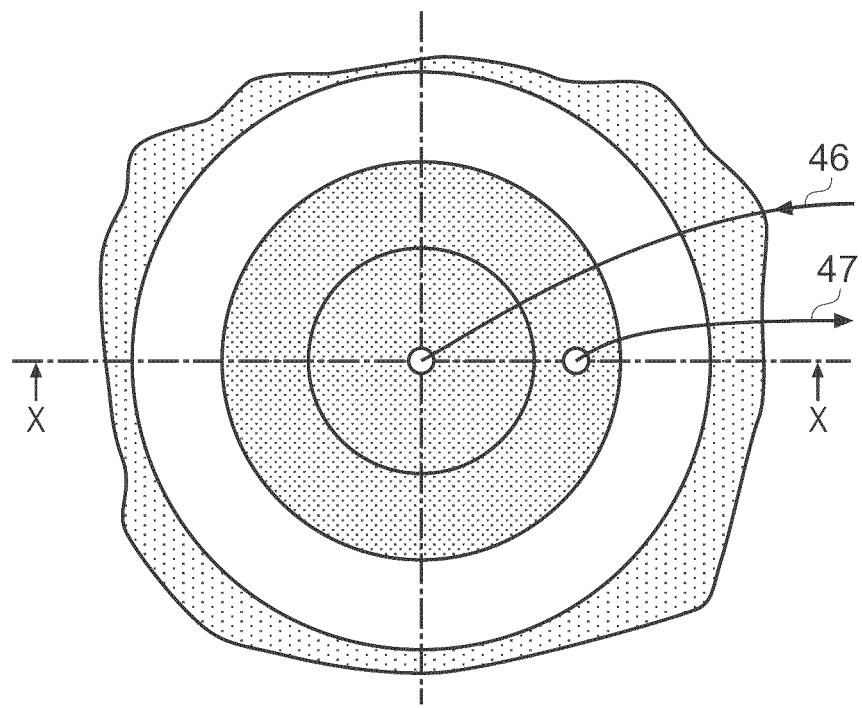
Figure 5B:
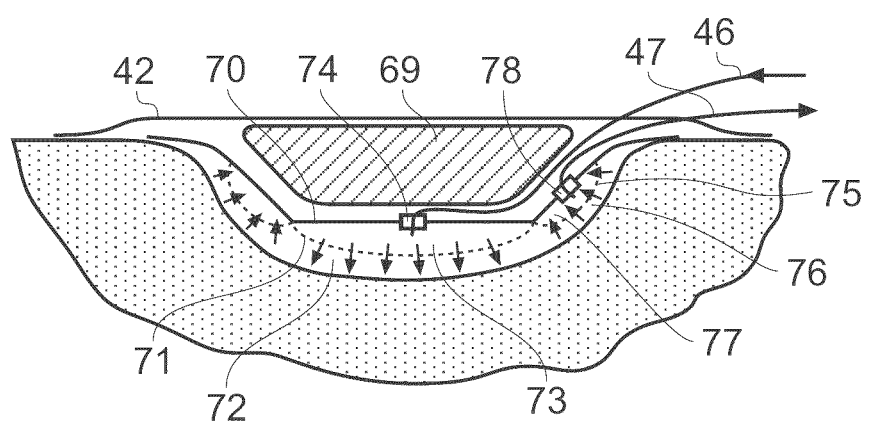

Referring to FIGS. 5a and 5b, a variant of the dressing of FIGS. 4a and 4b that is a more suitable form for deeper wounds is shown.

This comprises a circular backing layer (42) and a filler (69), in the form of an inverted frustroconical, solid integer, here a resilient elastomeric foam, formed of a thermoplastic, or preferably a cross-linked plastics foam.

It may be permanently attached to the backing layer (42), with an adhesive film (not shown) or by heat-sealing.

A circular upwardly dished sheet (70) lies under and conforms to, but is a separate structure, permanently unattached to, the backing layer (42) and the solid integer (69).

A circular upwardly dished first membrane (71) with apertures (72) is permanently attached to the sheet (70) by heat-sealing to form a circular pouch (73) with the sheet (70).

The pouch (73) communicates with the inlet pipe (46) through a hole (74), and thus effectively forms an inlet pipe manifold that delivers the circulating or aspirating fluid directly to the wound when the dressing is in use.

An annular second membrane (75) with openings (76) is permanently attached to the sheet (70) by heat-sealing to form an annular chamber (77) with the sheet (70).

The chamber (77) communicates with the outlet pipe (47) through an orifice (78), and thus effectively forms an outlet pipe manifold that collects the fluid directly from the wound when the dressing is in use.

Alternatively, where appropriate the dressing may be provided in a form in which the circular upwardly dished sheet (70) functions as the backing layer and the solid filler (69) sits on the sheet (70) as the backing layer, rather than under it. The filler (69) is held in place with an adhesive film or tape, instead of the backing layer (42).

Figure 6A:
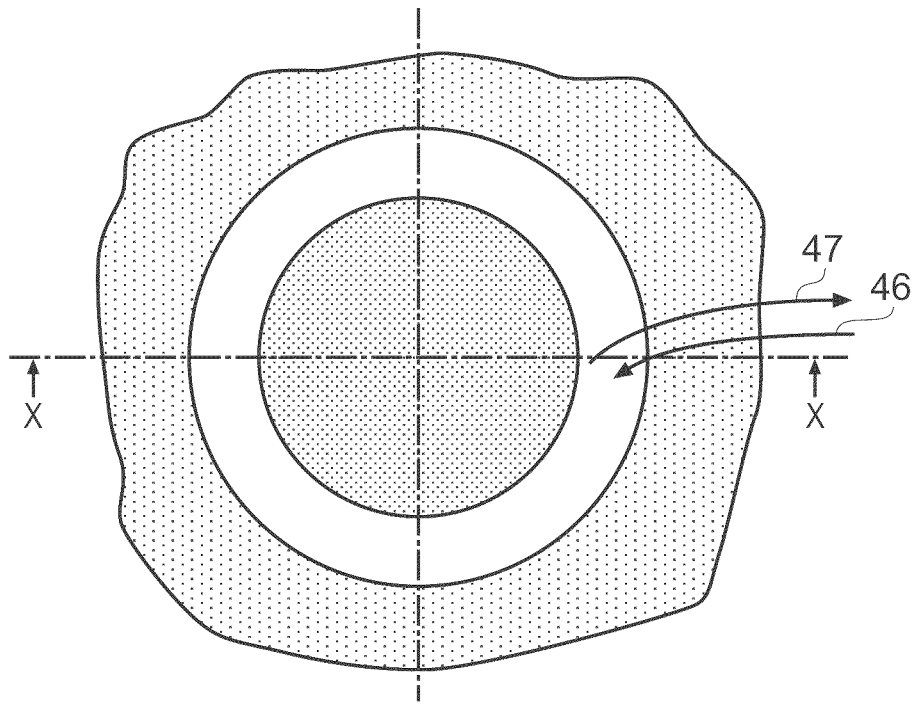
Figure 6B:
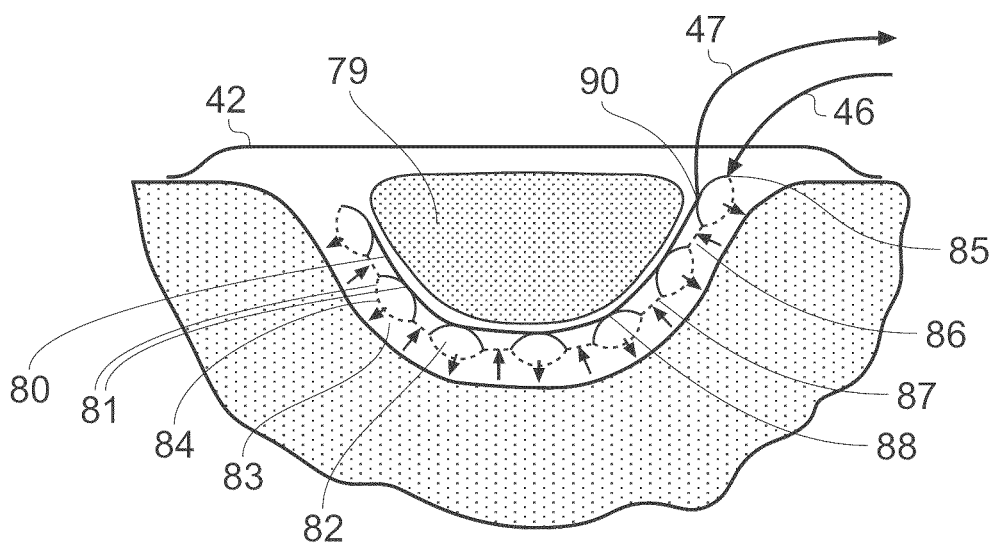

Referring to FIGS. 6a and 6b, a dressing that is a more suitable form for deeper wounds is shown.

This comprises a circular backing layer (42) and a filler (79), in the form of an inverted generally hemispherical integer, permanently attached to the backing layer with an adhesive film (not shown) or by heat-sealing.

Here it is a resilient elastomeric foam or a hollow body filled with a fluid, here a gel that urges it to the wound shape. The inlet pipe (46) and outlet pipe (47) are mounted peripherally in the backing layer (42). A circular upwardly dished sheet (80) lies under and conforms to, but is a separate structure, permanently unattached to, the backing layer (42) and the filler (79).

A circular upwardly dished bilaminate membrane (81) has a closed channel (82) between its laminar components, with perforations (83) along its length on the outer surface (84) of the dish formed by the membrane (81) and an opening (85) at the outer end of its spiral helix, through which the channel (82) communicates with the inlet pipe (46), and thus effectively forms an inlet pipe manifold that delivers the circulating or aspirating fluid directly to the wound when the dressing is in use.

The membrane (81) also has apertures (86) between and along the length of the turns of the channel (82). The inner surface (87) of the dish formed by the membrane (81) is permanently attached at its innermost points (88) with an adhesive film (not shown) or by heat-sealing to the sheet (80). This defines a mating closed spirohelical conduit.

At the outermost end of its spiral helix, the conduit communicates through an opening (90) with the outlet pipe (47) and is thus effectively an outlet manifold to collect the fluid directly from the wound via the apertures (86).

Figure 7A:
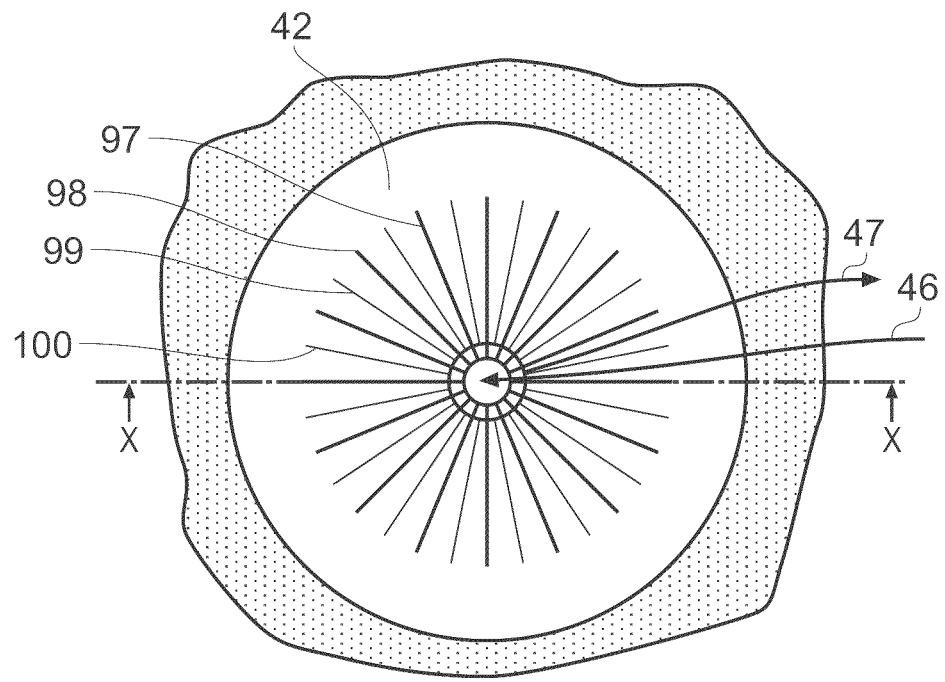
Figure 7B:
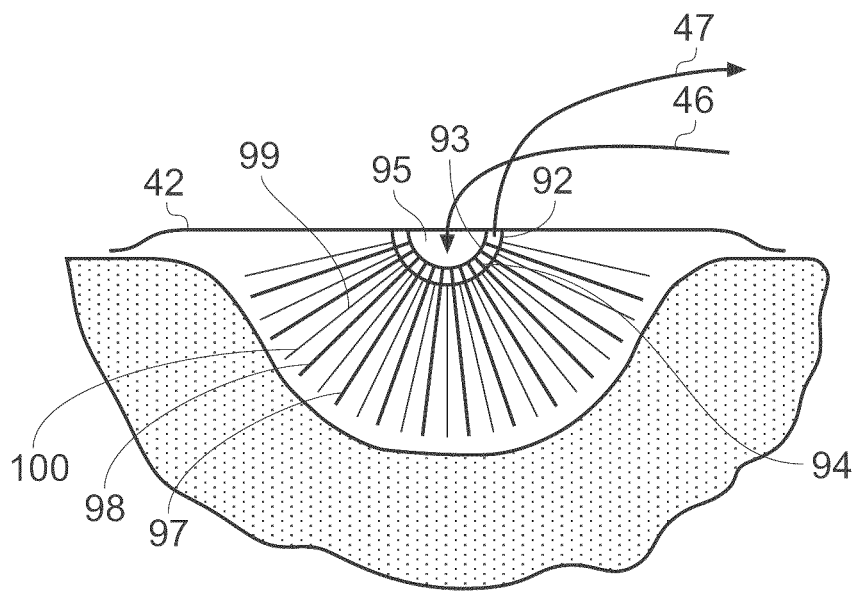

Referring to FIGS. 7a and 7b, one form of the dressing is provided with a circular backing layer (42).

A first (larger) inverted hemispherical membrane (92) is permanently attached centrally to the layer (42) by heat-sealing to form a hemispherical chamber (94) with the layer (42).

A second (smaller) concentric hemispherical membrane (93) within the first is permanently attached to the layer (42) by heat-sealing to form a hemispherical pouch (95).

The pouch (95) communicates with the inlet pipe (46) and is thus effectively an inlet manifold, from which pipes (97) radiate hemispherically and run to the scaffold and/or wound bed to end in apertures (98). The pipes (97) deliver the aspirating fluid directly to the scaffold and/or wound bed via the apertures (98).

The chamber (94) communicates with the outlet pipe (47) and is thus effectively an outlet manifold from which tubules (99) radiate hemispherically and run to the scaffold and/or wound bed to end in openings (100). The tubules (99) collect the fluid directly from the wound via the openings (100).

Referring to FIGS. 8a to 8d, one form of the dressing is provided with a square backing layer (42) and first tube (101) extending from the inlet pipe (46), and second tube (102) extending from the outlet pipe (47) at the points at which they pass through the backing layer, to run over the scaffold and/or wound bed.

These pipes (101) and (102) have a blind bore with orifices (103) and (104) along the pipes (101) and (102).

These pipes (101) and (102) respectively form an inlet pipe or outlet pipe manifold that delivers the aspirating fluid directly to the scaffold and/or wound bed or collects the fluid directly from the wound respectively via the orifices.

Figure 8A:
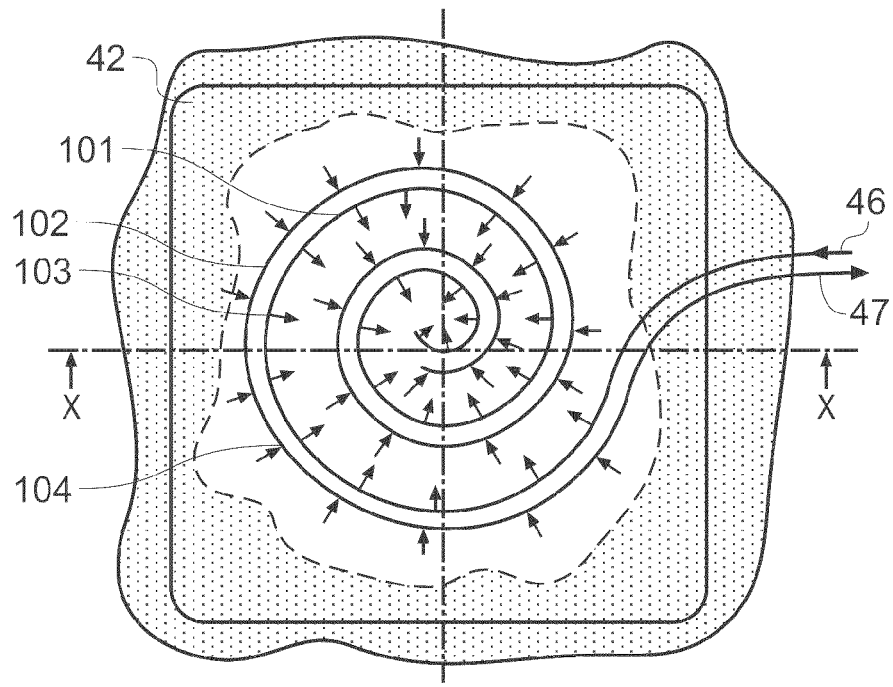
Figure 8B:
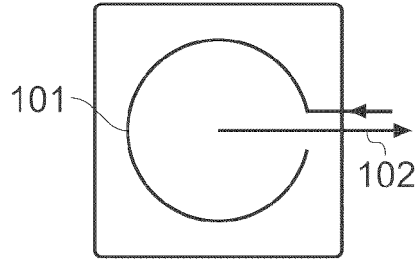
Figure 8C:
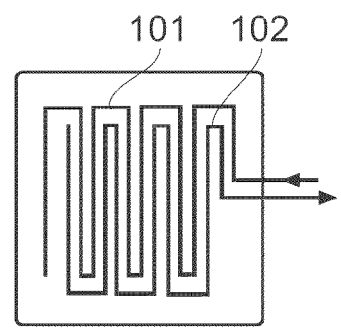
Figure 8D:
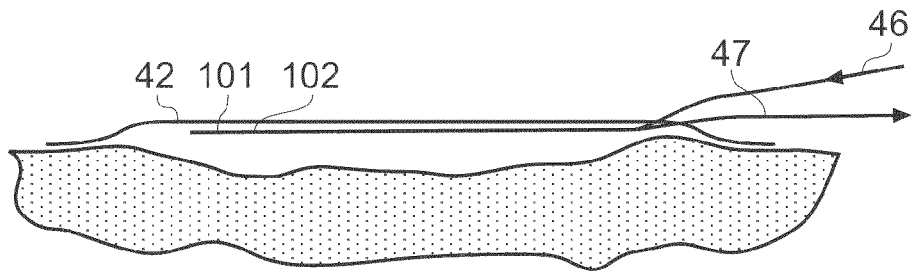
Figure 9A:
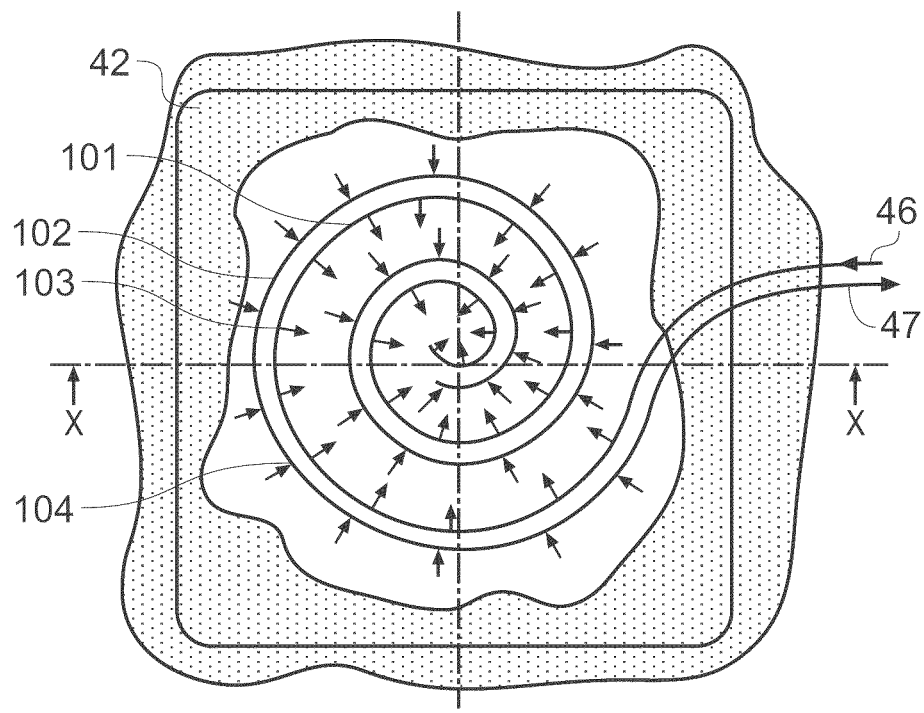
Figure 9B:
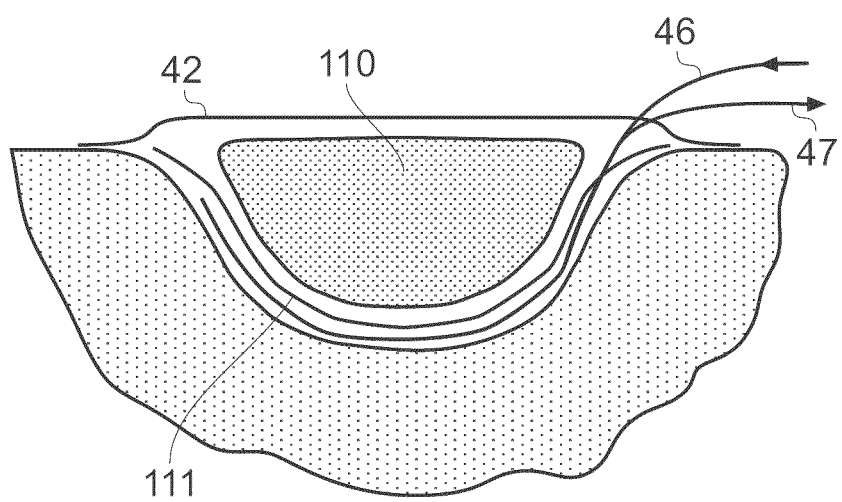

In FIGS. 8a and 8d, one layout of each of the pipes (101) and (102) as inlet pipe and outlet pipe manifolds is a spiral.

In FIG. 8b, the layout is a variant of that of FIGS. 8a and 8b, with the layout of the inlet manifold (101) being a full or partial torus, and the outlet manifold (102) being a radial pipe.

Referring to FIG. 8c, there is shown another suitable layout in which the inlet manifold (101) and the outlet manifold (102) run alongside each other over the scaffold and/or wound bed in a boustrophedic pattern, i.e. in the manner of ploughed furrows.

Referring to FIGS. 9a to 9d, there are shown other suitable layouts for deeper wounds, which are the same as shown in FIGS. 8a to 8d. The square backing layer (42) however has a wound filler (110) under, and may be permanently attached to, the backing layer (42), with an adhesive film (not shown) or by heat-sealing, which is an inverted hemispherical solid integer, here a resilient elastomeric foam, formed of a thermoplastic, preferably a cross-linked plastics foam.

Under the latter is a circular upwardly dished sheet (111) which conforms to, but is a separate structure, permanently unattached to, the solid filler (110). Through the sheet (111) pass the inlet pipe (46) and the outlet pipe (47), to run over the scaffold and/or wound bed. These pipes (101) and (102) again have a blind bore with orifices (103) and (104) along the pipes (101) and (102).

Alternatively (as in FIGS. 5a and 5b), where appropriate the dressing may be provided in a form in which the circular upwardly dished sheet (111) functions as the backing layer and the solid filler (110) sits on the sheet (42) as the backing layer, rather than under it. The filler (110) is held in place with an adhesive film or tape, instead of the backing layer (42).

In FIGS. 10a to 10c, inlet and outlet manifolds for the wound dressings for respectively delivering fluid to, and collecting fluid from, the wound, are formed by slots in and apertures through layers permanently attached to each other in a stack.

Thus, in FIG. 10a there is shown an exploded isometric view of an inlet manifold and outlet manifold stack (120) of five square coterminous thermoplastic polymer layers, being first to fifth layers (121) to (125), each attached with an adhesive film (not shown) or by heat-sealing to the adjacent layer in the stack (120).

The topmost (first) layer (121) (which is the most distal in the dressing in use) is a blank square capping layer.

The next (second) layer (122), shown in FIG. 10b out of the manifold stack (120), is a square layer, with an inlet manifold slot (126) through it. The slot (126) runs to one edge (127) of the layer (122) for connection to a mating end of a fluid inlet tube ((not shown), and spreads into four adjacent branches (128) in a parallel array with spaces therebetween.

The next (third) layer (123) is another square layer, with inlet manifold apertures (129) through the layer (123) in an array such that the apertures (129) are in register with the inlet manifold slot (126) through the second layer (122) (shown in FIG. 10b).

The next (fourth) layer (124), shown in FIG. 10c out of the manifold stack (120), is another square layer, with inlet manifold apertures (130) through the layer (124) in an array such that the apertures (130) are in register with the apertures (129) through the third layer (123).

It also has an outlet manifold slot (131) through it.

The slot (131) runs to one edge (132) of the layer (124) on the opposite side of the manifold stack (120) from the edge (127) of the layer (122), for connection to a mating end of a fluid outlet tube (not shown).

It spreads into three adjacent branches (133) in a parallel array in the spaces between the apertures (130) in the layer (124) and in register with the spaces between the apertures (129) in the layer (122).

The final (fifth) layer (125) is another square layer, with inlet manifold apertures (134) through the layer (125) in an array such that the apertures (134) are in register with the inlet manifold apertures (130) through the fourth layer (124) (in turn in register with the apertures (129) through the third layer (123). It also has outlet manifold apertures (135) in the layer (125) in an array such that the apertures (135) are in register with the outlet manifold slot (131) in the fourth layer (124).

It will be seen that, when the layers (121) to (125) are attached together to form the stack (120), the topmost (first) layer (121), the inlet manifold slot (126) through the second layer (122), and the third layer (123) cooperate to form an inlet manifold in the second layer (122), which is in use is connected to a mating end of a fluid inlet tube (not shown).

The inlet manifold slot (126) through the second layer (122), and the inlet manifold apertures (129), (130) and (134) through the layers (123), (124) and (125), all being mutually in register, cooperate to form inlet manifold conduits through the third to fifth layers (123), (124) and (125) between the inlet manifold in the second layer (122) and the proximal face (136) of the stack (120).

The third layer (121), the outlet manifold slot (131) through the fourth layer (124), and the fifth layer (125) cooperate to form an outlet manifold in the fourth layer (124), which is in use is connected to a mating end of a fluid outlet tube (not shown).

The outlet manifold slot (131) through the fourth layer (124), and the outlet manifold apertures (135) through the fifth layer (125), being mutually in register, cooperate to form outlet manifold conduits though the fifth layer (125) between the outlet manifold in the fourth layer (124) and the proximal face (136) of the stack (120).

Figure 11A:
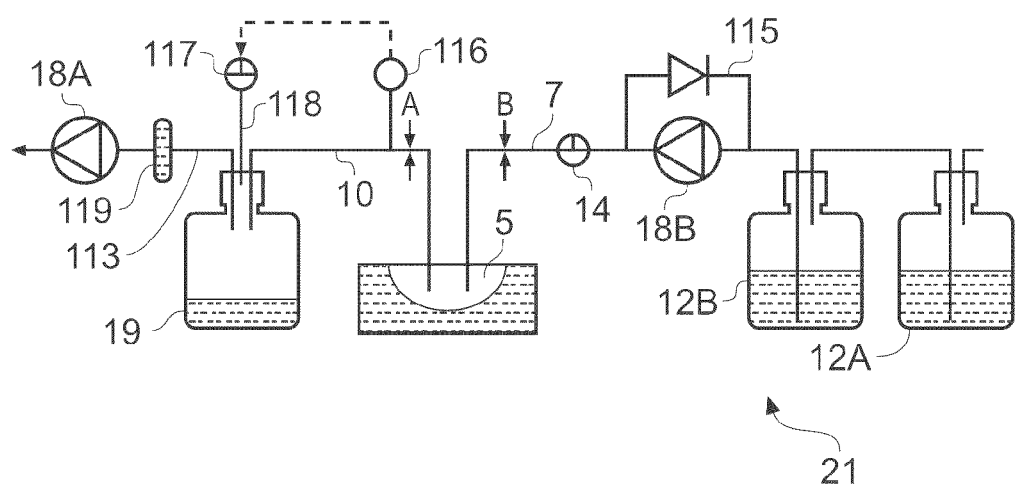
FIGS. 11a to d are variants of a two-pump system with essentially identical, and identically numbered, components as in FIG. 2, except that there is a pump bypass loop, (in all except in FIG. 11c), a filter downstream of the aspirate collection vessel, and a bleed regulator, such as a rotary valve, connected to the fluid offtake tube or to the wound space, for the regulation of the positive or negative pressure applied to the wound.

Referring to FIG. 11a, the apparatus (21) is a variant two-pump system with essentially identical, and identically numbered, components as in FIG. 2.

Thus, there is a means for supply flow regulation, here a valve (14) in the fluid supply tube (7) from the fluid reservoir (12B), and a first device for moving fluid through the wound (5), here a fixed-speed diaphragm pump (18A), e.g. preferably a small portable diaphragm pump, acting not on the fluid aspiration tube (13), but on an air aspiration tube (113) downstream of and away from an aspirate collection vessel (19) to apply a low negative pressure on the wound through the aspirate collection vessel (19); with a second device for moving fluid through the wound (5), here a fixed-speed peristaltic pump (18B), e.g. preferably a small portable peristaltic pump, applied to the irrigant in the fluid supply tube (7) upstream of and towards the wound dressing, the first device (18A) and second device (18B), and the valve (14) in the fluid supply tube (7), providing means for providing simultaneous aspiration and irrigation of the wound (5), such that fluid may be supplied to fill the flowpath from the fluid reservoir via the fluid supply tube (via the means for supply flow regulation) and moved by the devices through the flow path.

Key differences as compared with FIG. 2 are that: the second device, pump (18B) acts, not on the fluid aspiration tube (13), but on an air aspiration tube (113) downstream of and away from an aspirate collection vessel (19); and there is no means for aspirate flow regulation, e.g. a valve connected to the fluid offtake tube (10). Since first device (18A) and second device (18B) are fixed-speed, the valve (14) in the fluid supply tube (7) provides the sole means for varying the irrigant flow rate and the low negative pressure on the wound.

The following extra features are present: The second device, the fixed-speed peristaltic pump (18B), is provided with means for avoiding over-pressure, in the form of a bypass loop with a non-return valve (115). The loop runs from the fluid supply tube (7) downstream of the pump (18B) to a point in the fluid supply tube (7) upstream of the pump (18B).

A pressure monitor (116) connected to the fluid offtake tube (10) has a feedback connection to a bleed regulator, here a motorized rotary valve (117) on a bleed tube (118) running to and centrally penetrating the top of the aspirate collection vessel (19). This provides means for holding the low negative pressure on the wound at a steady level.

Figure 11B:
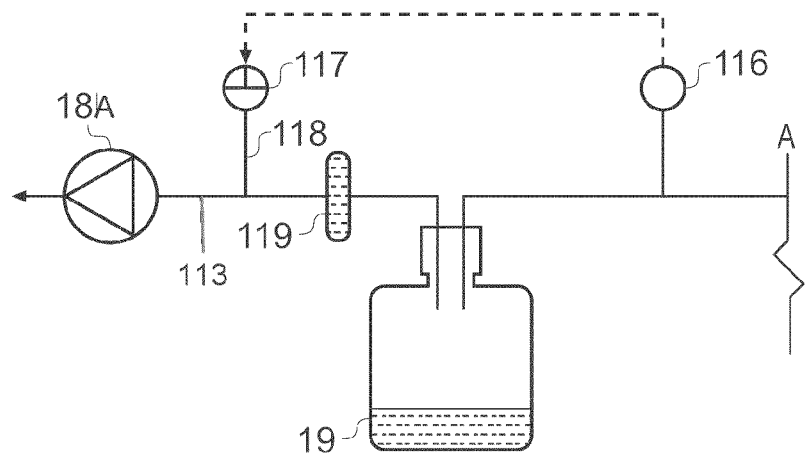
Figure 11C:
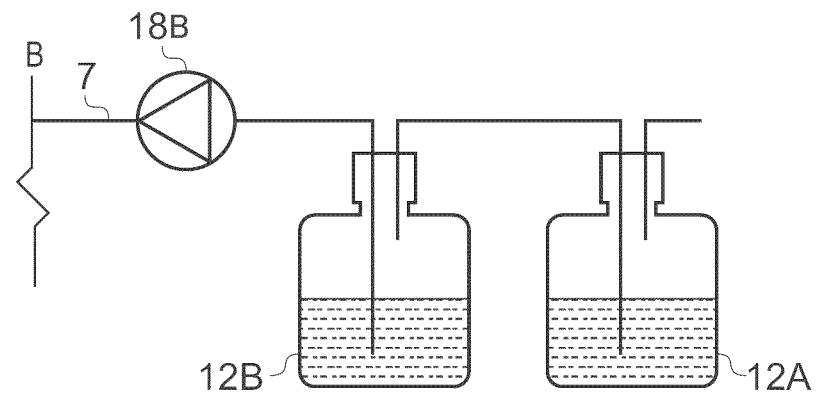
Figure 11D:
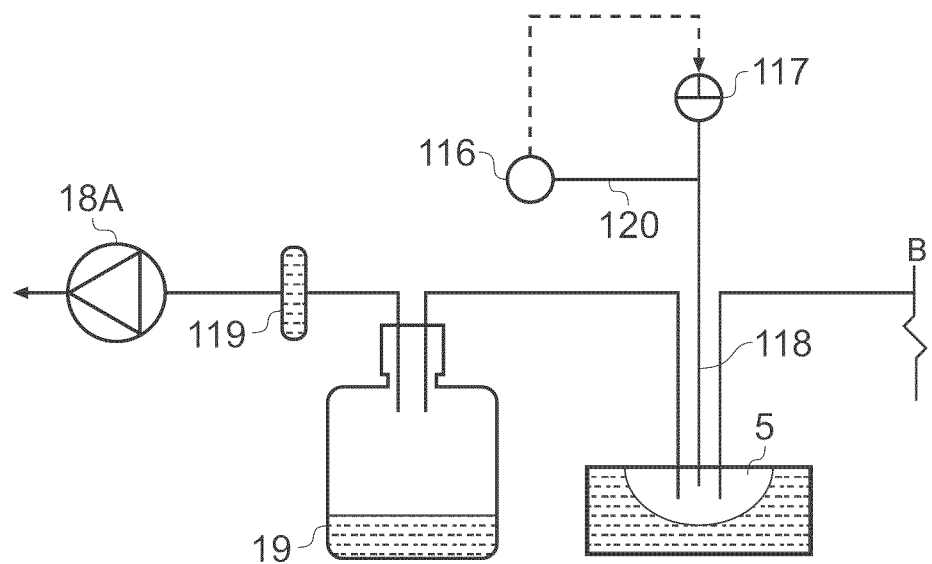

A filter (119) downstream of the aspirate collection vessel (19) prevents passage of gas- (often air-) borne particulates, including liquids and micro-organisms, from the irrigant and/or exudate that passes into the aspirate collection vessel (19) into the first device (18A), whilst allowing the carrier gas to pass through the air aspiration tube (113) downstream of it to the first device (18A). The operation of the apparatus is as described hereinbefore Referring to FIG. 11b, this shows an alternative layout of the essentially identical, and identically numbered, components in FIG. 11a downstream of point A. The bleed tube (118) runs to the air aspiration tube (113) downstream of the filter (119), rather than into the aspirate collection vessel (19). This provides means for holding the low negative pressure on the wound at a steady level. The operation of the apparatus is as described hereinbefore Referring to FIG. 11c, this shows an alternative layout of the essentially identical, and identically numbered, components in FIG. 11a upstream of point B. The second device (18B) is a variable-speed pump, and the valve (14) in the fluid supply tube (7) is omitted. The second device (18B) is the sole means for varying the irrigant flow rate and the low negative pressure on the wound. The operation of the apparatus is as described hereinbefore Referring to FIG. 11d, this shows an alternative layout of the essentially identical, and identically numbered, components in FIG. 11a downstream of point B.

Figure 12A:
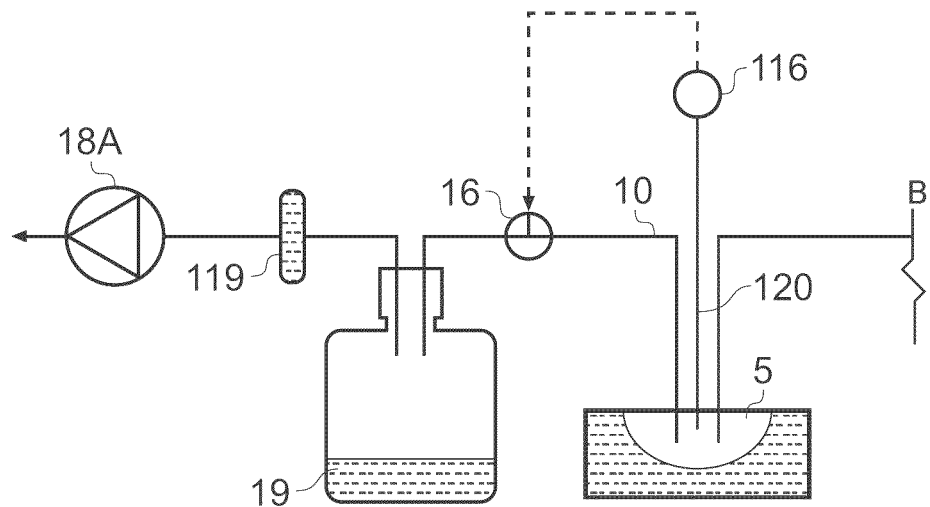
FIGS. 12a to c are variants of a two-pump system with essentially identical, and identically numbered, components as in FIG. 11, except that they have various means for varying the regulation of the positive or negative pressure applied to the wound.

The pressure monitor (116) is connected to a monitor offtake tube (120) and has a feedback connection to the bleed regulator, motorized rotary valve (117) on a bleed tube (118) running to the monitor offtake tube (120). This provides means for holding the low negative pressure on the wound at a steady level. The operation of the apparatus is as described hereinbefore Referring to FIG. 12a, this shows another alternative layout of the essentially identical, and identically numbered, components in FIG. 11a downstream of point B.

The pressure monitor (116) is connected to a monitor offtake tube (120) and has a feedback connection to a means for aspirate flow regulation, here a motorized valve (16) in the fluid offtake tube (10) upstream of the filter (119).

Figure 12B:
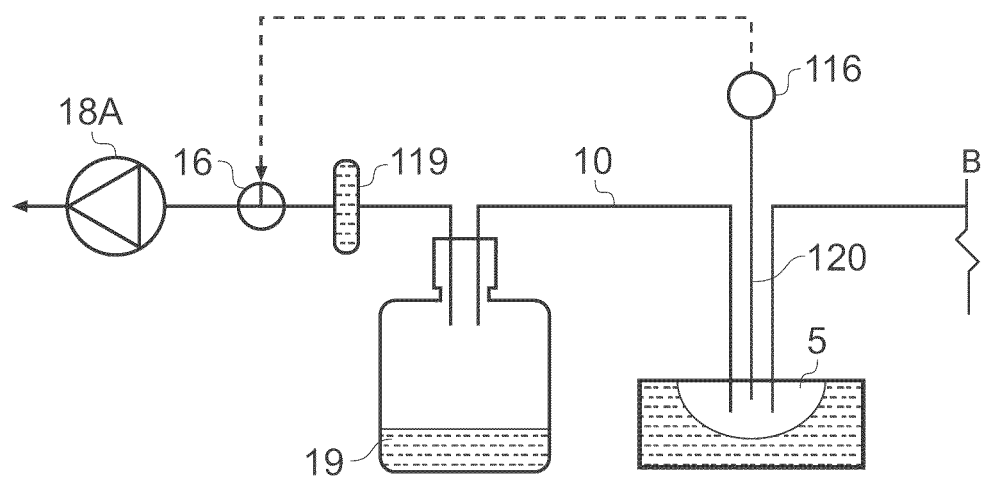

This provides means for aspirate flow regulation and for holding the low negative pressure on the wound at a steady level. The operation of the apparatus is as described hereinbefore Referring to FIG. 12b, this shows another alternative layout of the essentially identical, and identically numbered, components in FIG. 12a downstream of point B in FIG. 11a. The pressure monitor (116) is connected to a monitor offtake tube (120) and has a feedback connection to a means for aspirate flow regulation, here a motorized valve (16), in the fluid offtake tube (10) upstream of the aspirate collection vessel (19).

Figure 12C:
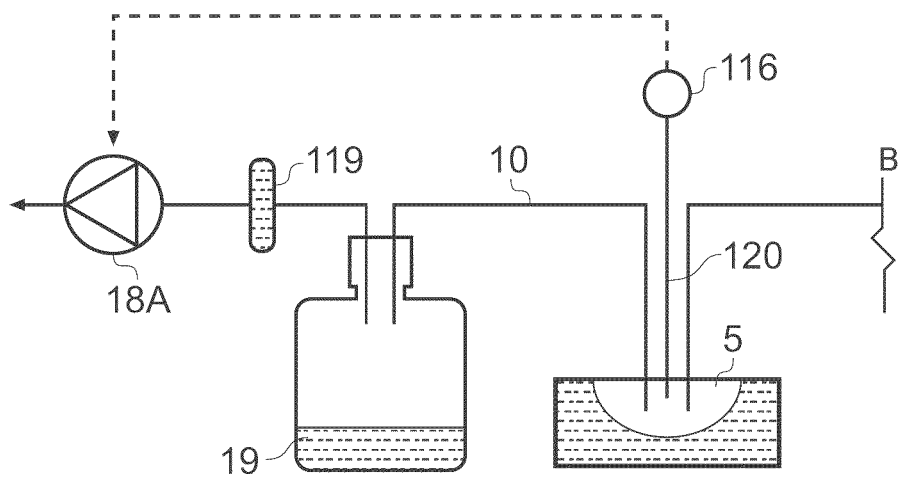

This provides means for aspirate flow regulation and for holding the low negative pressure on the wound at a steady level. The operation of the apparatus is as described hereinbefore Referring to FIG. 12c, this shows another alternative layout of the essentially identical, and identically numbered, components in FIG. 12a downstream of point B in FIG. 11a. The pressure monitor (116) is connected to a monitor offtake tube (120) and has a feedback connection to a variable-speed first device (18A), here a variable-speed pump, downstream of the filter (119), and the valve (16) in the fluid offtake tube (10) is omitted. This provides means for aspirate flow regulation and for holding the low negative pressure on the wound at a steady level. The operation of the apparatus is as described hereinbefore.

Figure 13A:
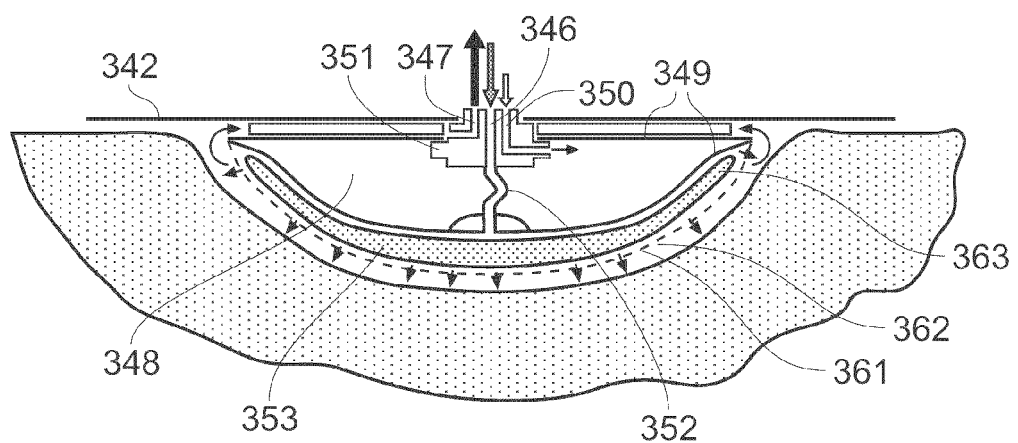
FIGS. 13 to 26 are cross-sectional views of conformable wound dressings, for aspirating and/or irrigating wounds.
Figure 13B:
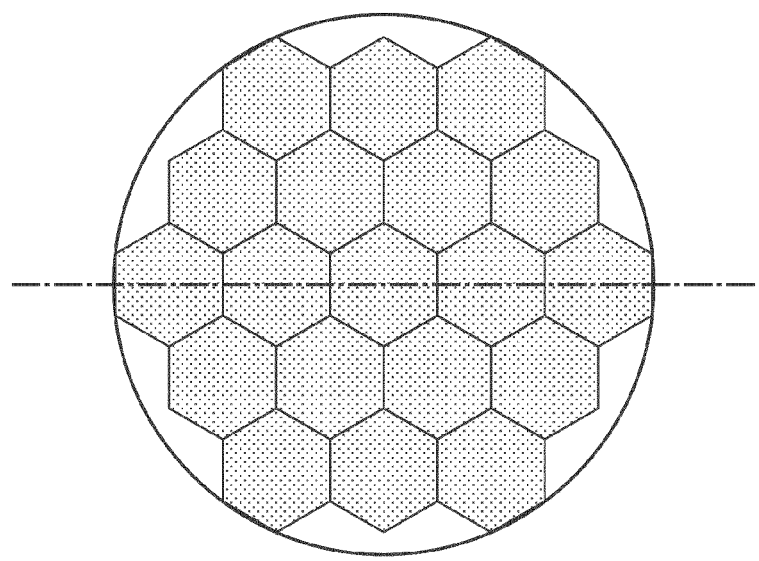
Figure 14:
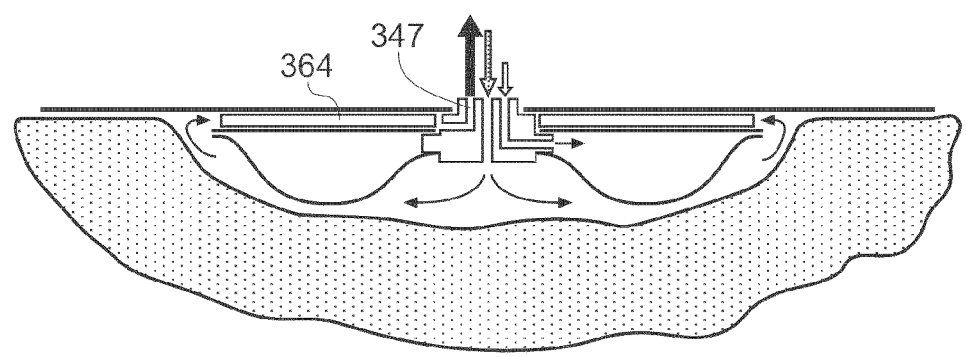
Figure 15:
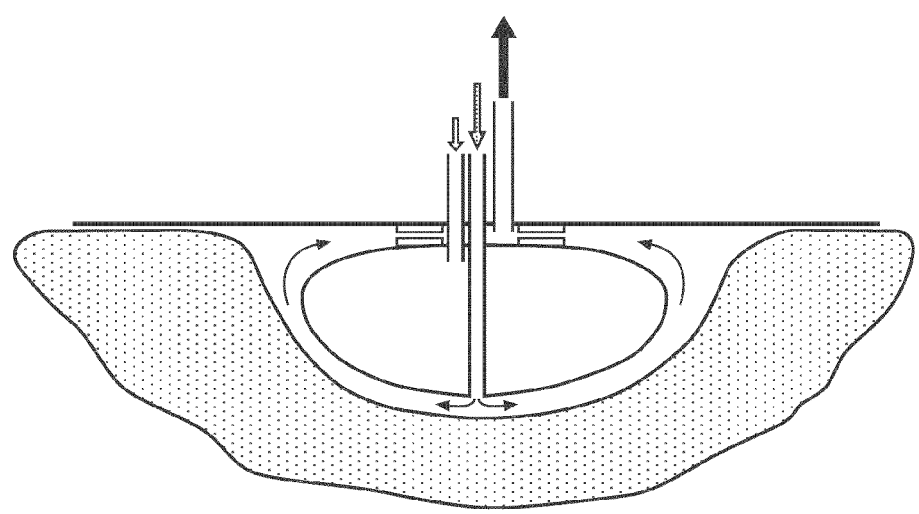

Referring to FIGS. 13 to 15, these forms of the dressing are provided with a wound filler (348) under a circular backing layer (342).

This comprises respectively a generally downwardly domed or toroidal, or oblately spheroidal conformable hollow body, defined by a membrane (349) which is filled with a fluid, here air or nitrogen, that urges it to the wound shape.

The filler (348) is permanently attached to the backing layer via a boss (351), which is e.g. heat-sealed to the backing layer (342).

An inflation inlet pipe (350), inlet pipe (346) and outlet pipe (347) are mounted centrally in the boss (351) in the backing layer (342) above the hollow body (348). The inflation inlet pipe (350) communicates with the interior of the hollow body (348), to permit inflation of the body (348). Though such inflation of the hollow body (348) the stress applied to the wound can be varied by varying the pressure within the hollow body (348). The inlet pipe (346) extends in a pipe (352) effectively through the hollow body (348). The outlet pipe (347) extends radially immediately under the backing layer (342).

In FIG. 13, the pipe (352) communicates with an inlet manifold (353), formed by a membrane (361) with apertures (362) that is permanently attached to the filler (348) by heat-sealing.

It is filled with foam (363) formed of a suitable material, e.g. a resilient thermoplastic. Preferred materials include reticulated filtration polyurethane foams with small apertures or pores.

In FIG. 14, the outlet pipe (347) communicates with a layer of foam (364) formed of a suitable material, e.g. a resilient thermoplastic. Again, preferred materials include reticulated filtration polyurethane foams with small apertures or pores.

The filler (348) is permanently attached to the backing layer via a boss (351), which is e.g. heat-sealed to the backing layer (342).

In all of FIGS. 13, 14 and 15, in use, the pipe (346) ends in one or more openings that deliver the irrigant fluid directly to the scaffold and/or wound bed over an extended area.

Similarly, the outlet pipe (347) effectively collects the fluid radially from the wound periphery when the dressing is in use.

Figure 16A:
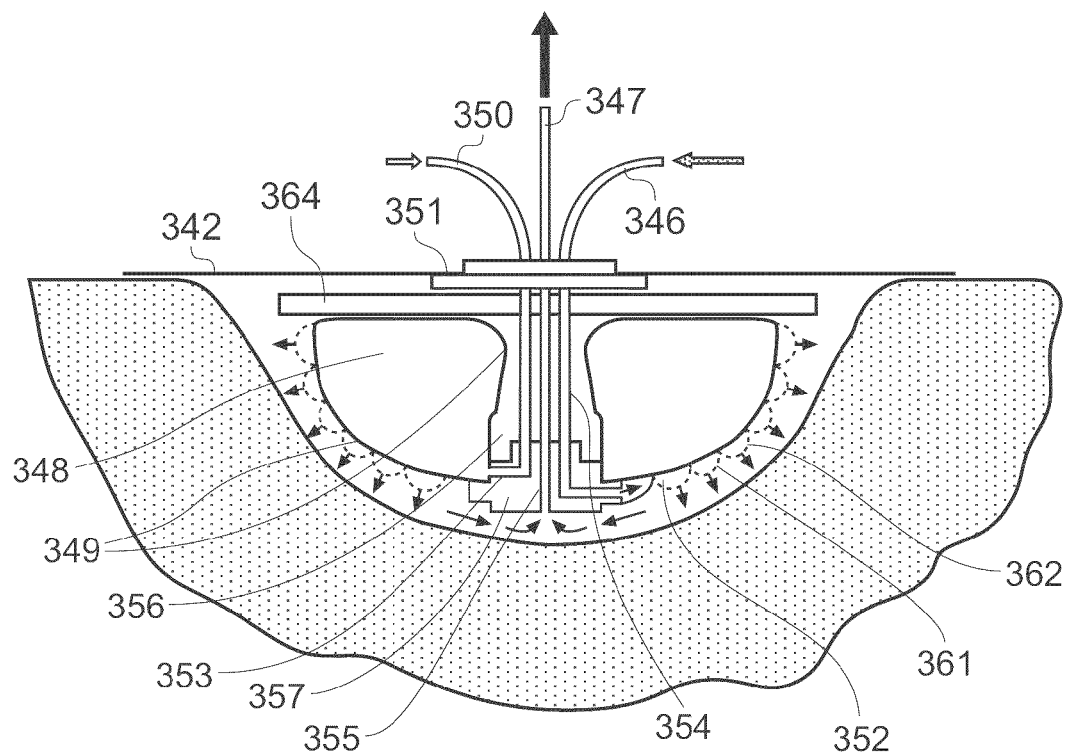
Figure 16B:
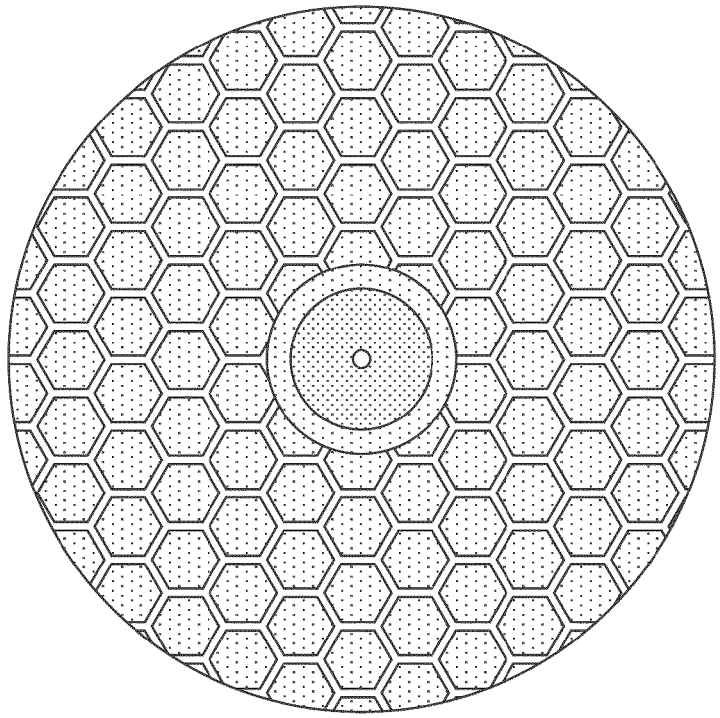

Referring to FIG. 16, the dressing is also provided with a wound filler (348) under a circular backing layer (342).

This also comprises a generally toroidal conformable hollow body, defined by a membrane (349) which is filled with a fluid, here air or nitrogen, that urges it to the wound shape.

The filler (348) may be permanently attached to the backing layer (342) via a first boss (351) and a layer of foam (364) formed of a suitable material, e.g. a resilient thermoplastic. Again, preferred materials include reticulated filtration polyurethane foams with small apertures or pores.

The first boss (351) and foam layer (364) are respectively heat-sealed to the backing layer (342) and the boss (351).

An inflation inlet pipe (350), inlet pipe (346) and outlet pipe (347) are mounted centrally in the first boss (351) in the backing layer (342) above the toroidal hollow body (348).

The inflation inlet pipe (350), inlet pipe (346) and outlet pipe (347) respectively each extend in a pipe (353), (354) and (355) through a central tunnel (356) in the hollow body (348) to a second boss (357) attached to the toroidal hollow body (348).

The pipe (353) communicates with the interior of the hollow body (348), to permit inflation of the body (348).

The pipe (354) extends radially through the second boss (357) to communicate with an inlet manifold (352), formed by a membrane (361).

This is permanently attached to the filler (348) by heat-sealing in the form of a reticulated honeycomb with openings (362) that deliver the irrigant fluid directly to the scaffold and/or wound bed over an extended area.

The pipe (355) collects the fluid flowing radially from the wound center when the dressing is in use.

This form of the dressing is a more suitable layout for deeper wounds

Figure 17:
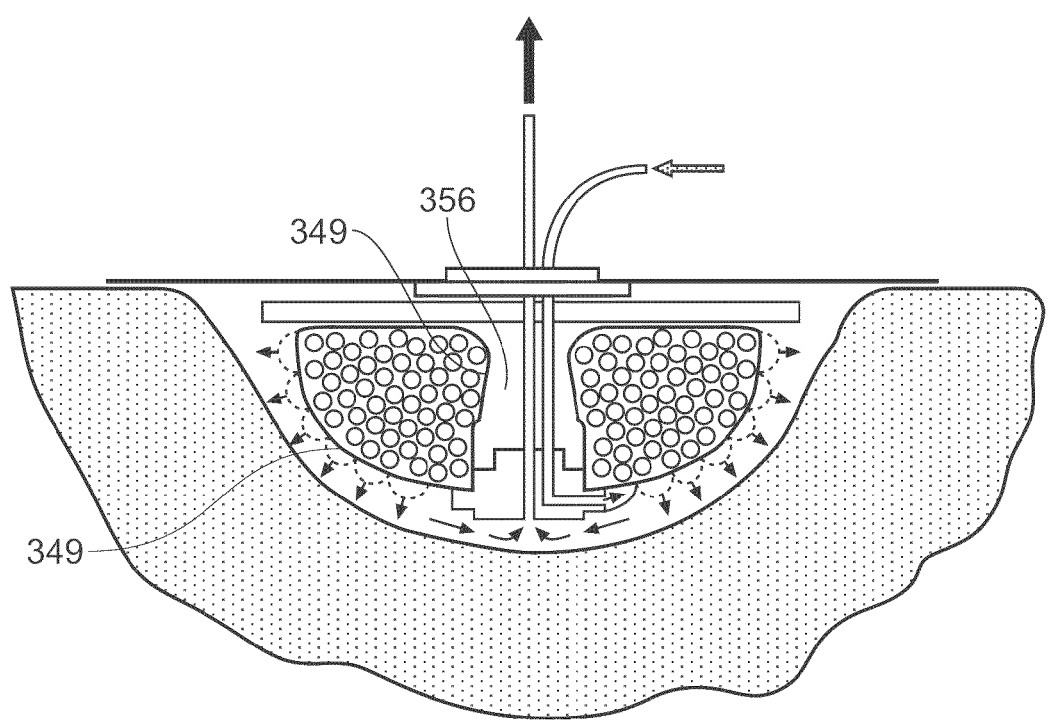

In FIG. 17, the dressing is similar to that of FIG. 16, except that the toroidal conformable hollow body, defined by a membrane (349), is filled with a fluid, here a solid particulates, such as plastics crumbs or beads, rather than a gas, such as air or an inert gas, such as nitrogen or argon.

The inflation inlet pipe (350) and pipe (353) are omitted from the central tunnel (356).

Examples of contents for the body (348) also include gels, such as silicone gels or preferably cellulosic gels, for example hydrophilic cross-linked cellulosic gels, such as Intrasite™ cross-linked materials. Examples also include aerosol foams, and set aerosol foams, e.g. CaviCare™ foam.

Figure 18A:
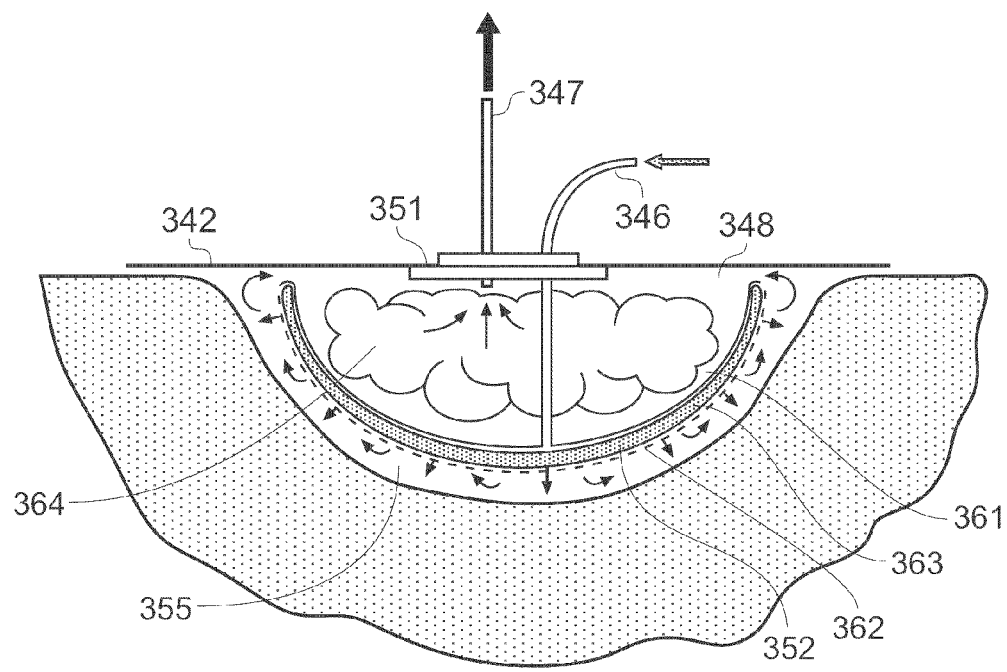
Figure 18B:
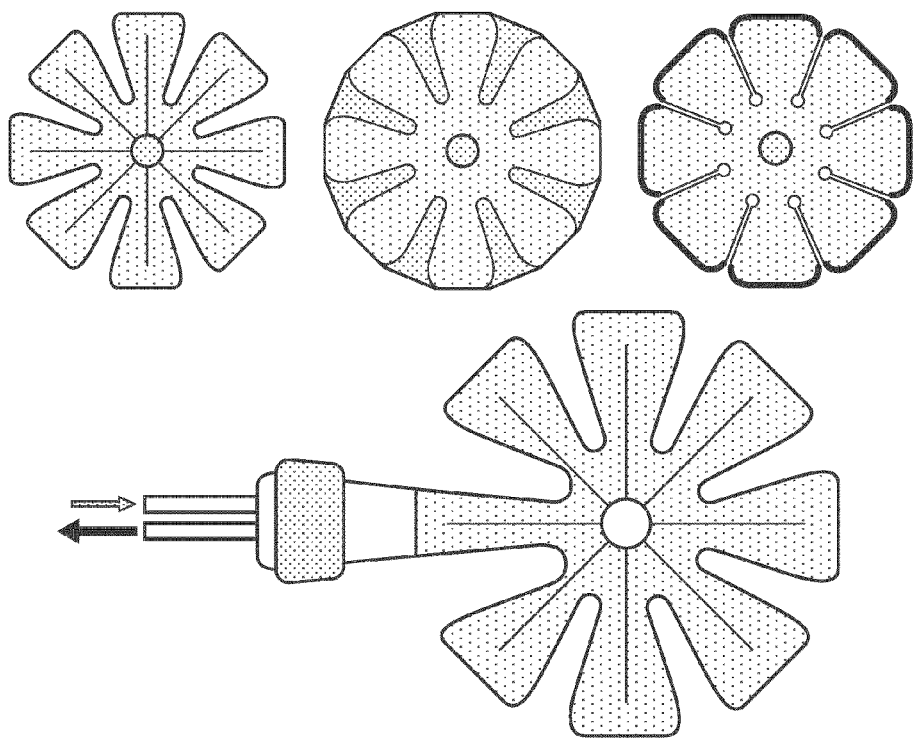
Figure 19:
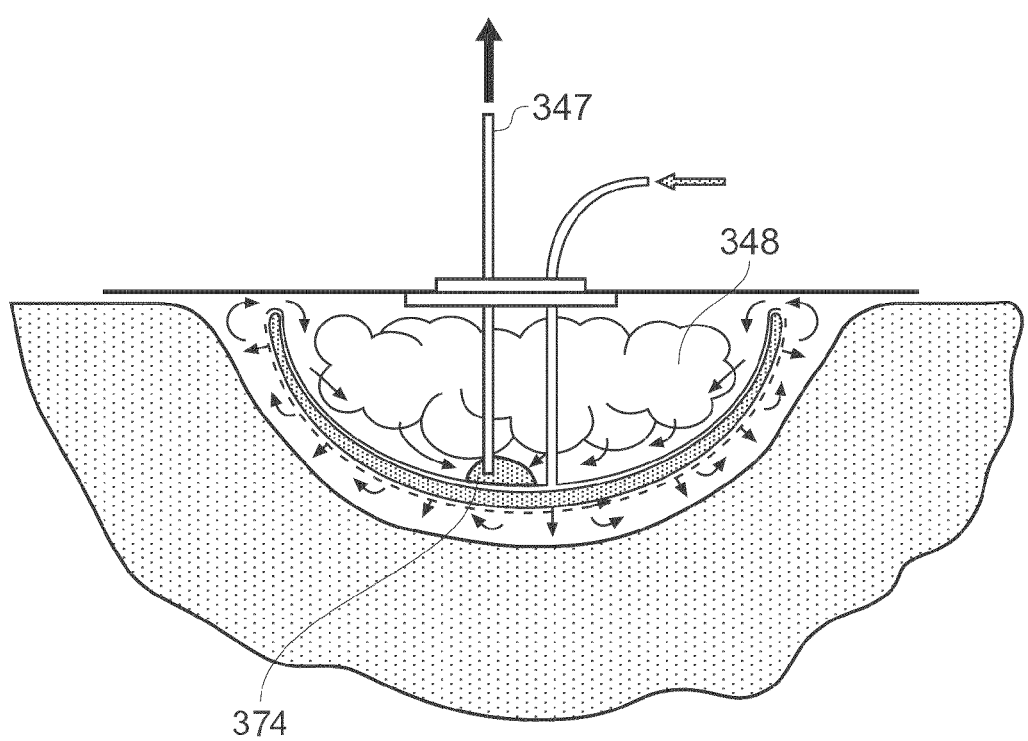

Referring to FIGS. 18 and 19, another form for deeper wounds is shown.

This comprises a circular backing layer (342) and a lobed chamber (363) in the form of a deeply indented disc much like a multiple Maltese cross or a stylised rose.

This is defined by an upper impervious membrane (361) and a lower porous film (362) with apertures (352) that deliver the irrigant fluid directly from the scaffold and/or wound bed over an extended area.

A number of configurations of the chamber (363) are shown, all of which are able to conform well to the wound bed by the arms closing in and possibly overlapping in insertion into the wound.

In a particular design of the chamber (363), shown lowermost, one of the arms is extended and provided with an inlet port at the end of the extended arm. This provides the opportunity for coupling and decoupling the irrigant supply remote from the dressing and the wound in use.

An inlet pipe (346) and outlet pipe (347) are mounted centrally in a boss (351) in the backing layer (342) above the chamber (363). The inlet pipe (346) is permanently attached to, and communicate with the interior of, the chamber (363), which thus effectively forms an inlet manifold. The space above the chamber (363) is filled with a loose gauze packing (364).

In FIG. 18, the outlet pipe (347) collects the fluid from the interior of the dressing from just under the wound-facing face of the backing layer (342).

A variant of the dressing of FIG. 18 is shown in FIG. 19. The outlet pipe (347) is mounted to open at the lowest point of the space above the chamber (363) into a piece of foam (374).

Figure 20:
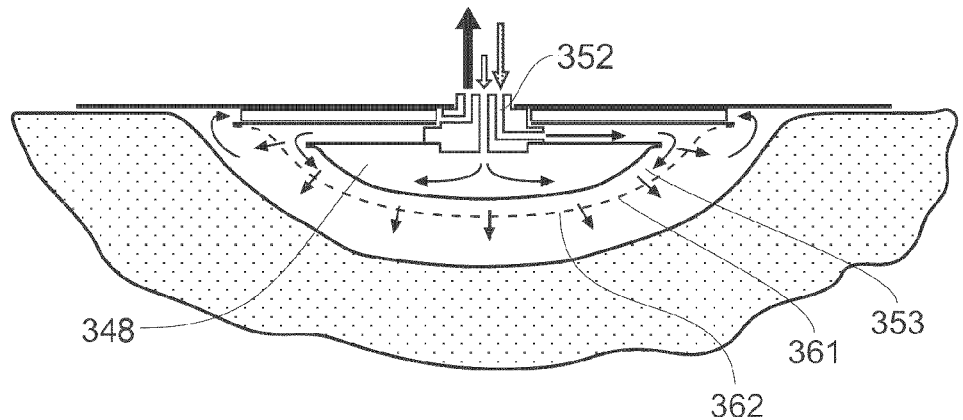

In FIG. 20, the dressing is similar to that of FIG. 13, except that the inlet pipe (352) communicates with an inlet manifold (353).

The latter is formed by a membrane (361) with apertures (362), over the upper surface of the generally downwardly domed wound hollow filler (348), rather than through it.

Figure 21:
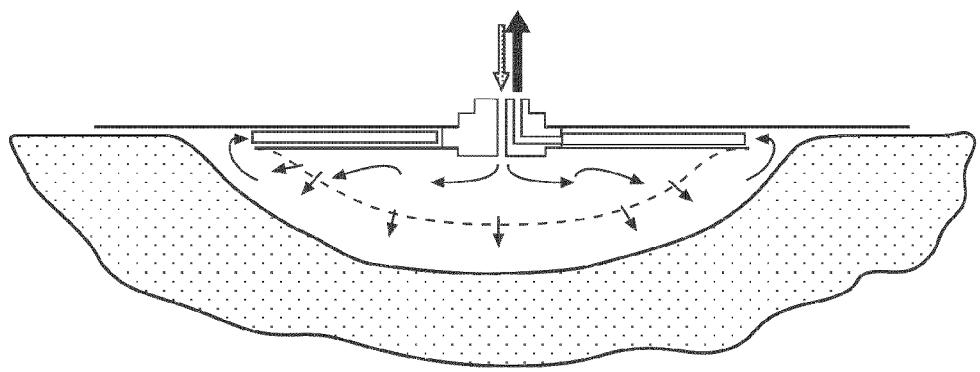

In FIG. 21, the generally downwardly domed annular wound hollow filler is omitted.

Figure 22:
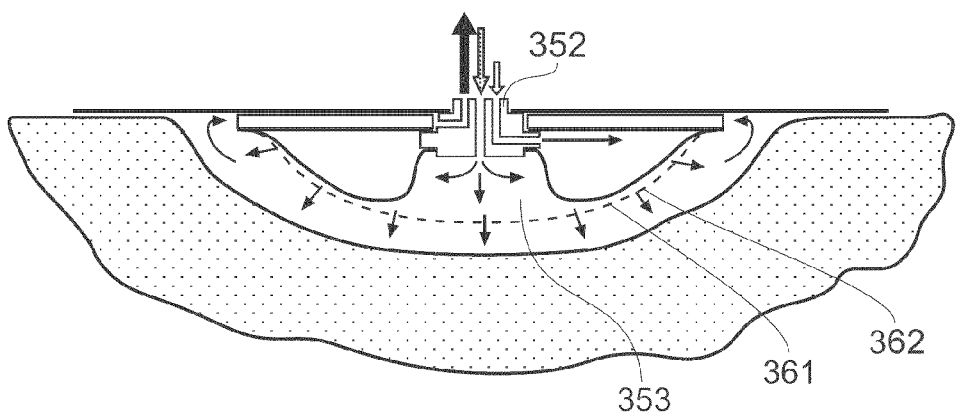

In FIG. 22, the dressing is similar to that of FIG. 14, with the addition of an inlet manifold (353), formed by a membrane (361) with apertures (362), over the lower surface of the generally downwardly domed annular wound hollow filler.

Figure 23:
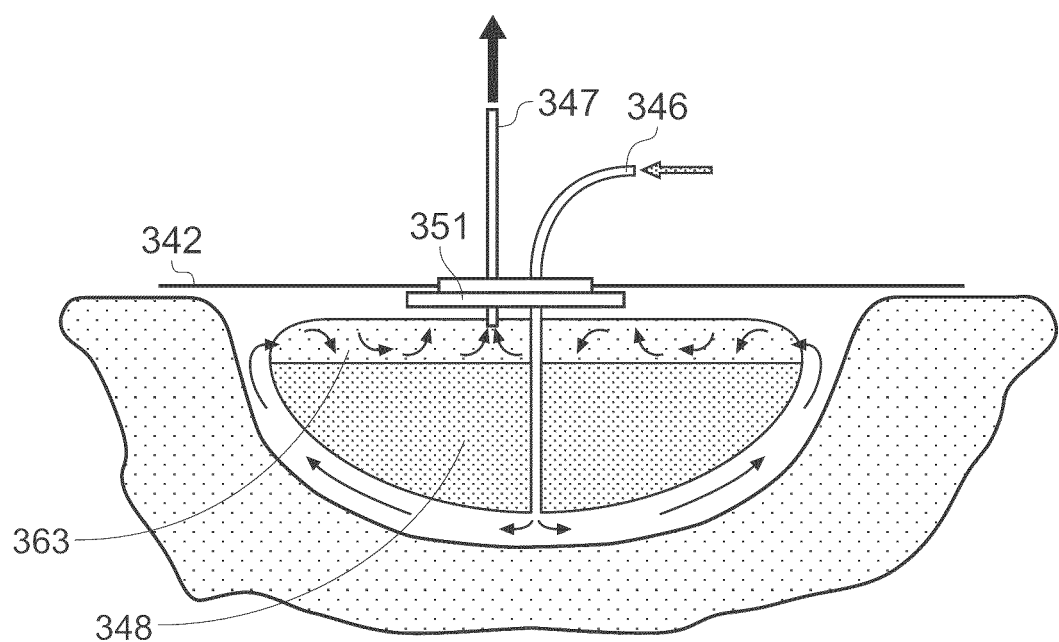

Referring to FIG. 23, another form for deeper wounds is shown. An inlet pipe (346) and outlet pipe (347) are mounted centrally in a boss (351) in the backing layer (342) above a sealed-off foam filler (348).

The inlet pipe (346) is permanently attached to and passes through the filler (348) to the scaffold and/or wound bed. The outlet pipe (347) is attached to and communicates with the interior of, a chamber (363) defined by a porous foam attached to the upper periphery of the filler (348). The chamber (363) thus effectively forms an outlet manifold.

Figure 24:
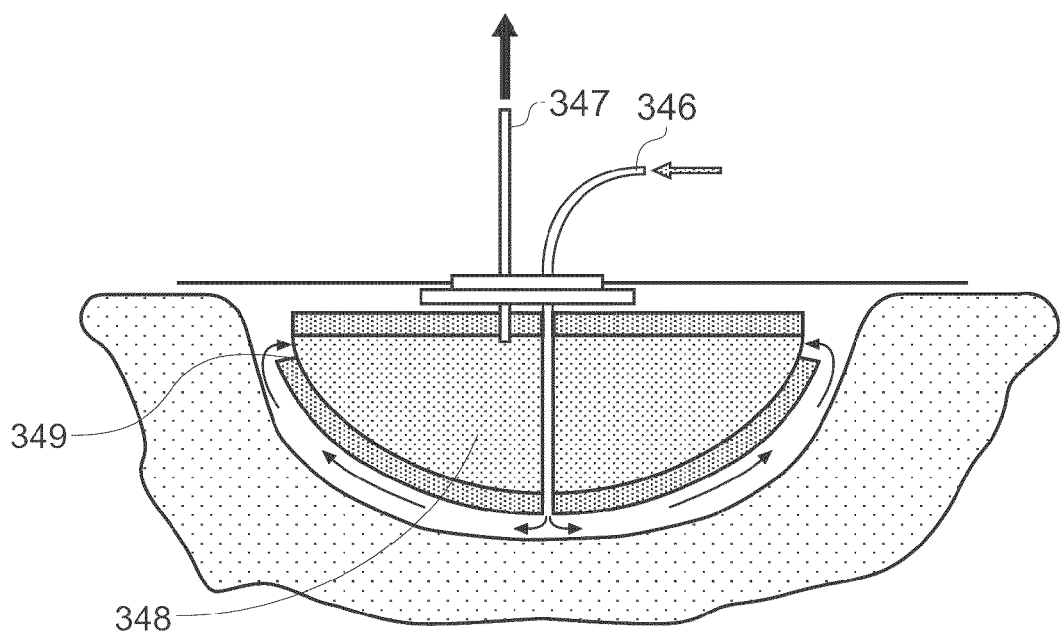

In FIG. 24, the foam filler (348) is only partially sealed-off. The inlet pipe (346) is permanently attached to and passes through the filler (348) to the scaffold and/or wound bed. The outlet pipe (347) is attached to and communicates with the interior of the foam of the filler (348). Fluid passes into an annular gap (349) near the upper periphery of the filler (348) into the foam, which thus effectively forms an outlet manifold.

Figure 25:
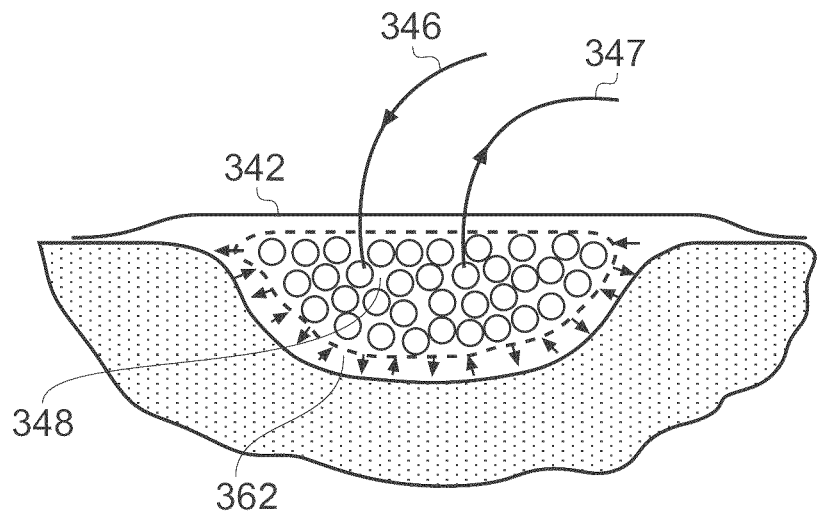
Figure 26:
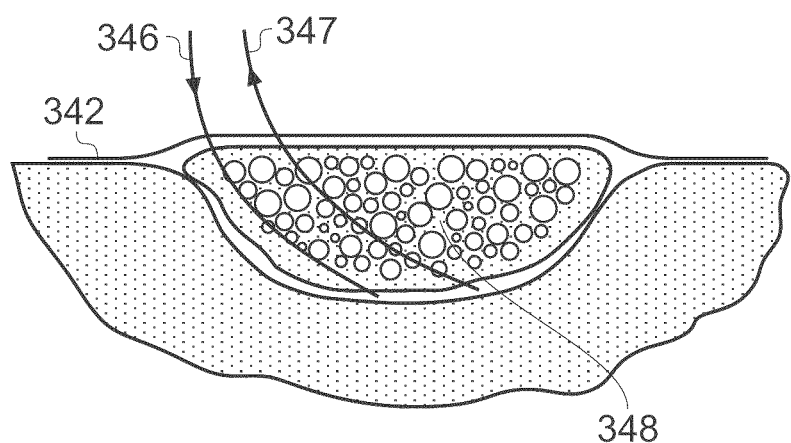

FIGS. 25 and 26 show dressings in which the inlet pipe (346) and outlet pipe (347) pass through the backing layer (342).

In FIG. 25, they communicate with the interior of a porous bag filler (348) defined by a porous film (369) and filled with elastically resilient plastics bead or crumb.

In FIG. 26, they communicate with the wound space just below a foam filler (348). The foam (348) may CaviCare™ foam, injected and formed in situ around the pipes (346) and (347).

Figure 27A:
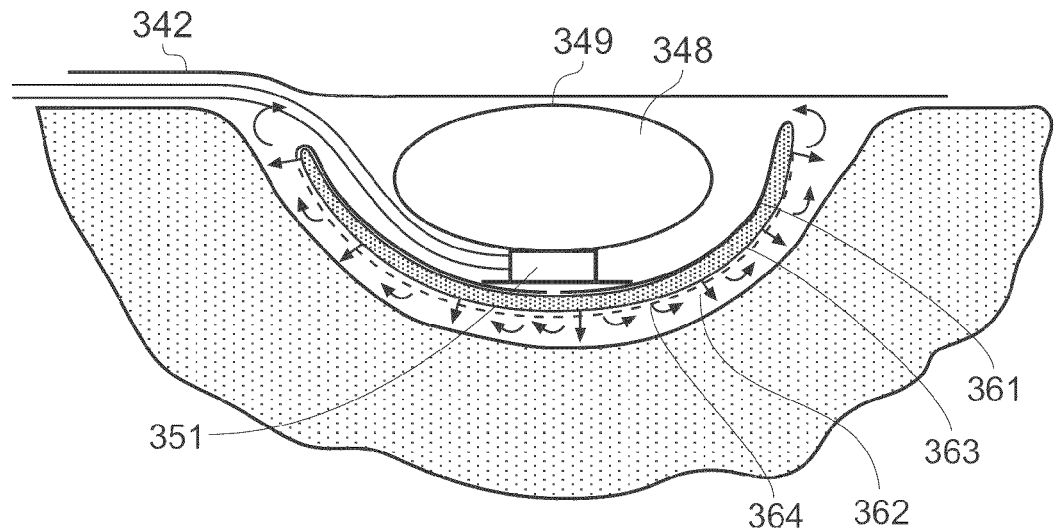
FIG. 27a is a plan view and FIG. 27b a cross-sectional view of a further conformable wound dressings for aspirating and/or irrigating wounds.

Referring to FIG. 27, another form for deeper wounds is shown. This comprises a circular, or more usually square or rectangular backing layer (342) and a chamber (363) in the form of a deeply indented disc much like a multiple Maltese cross or a stylised rose.

Figure 27B:
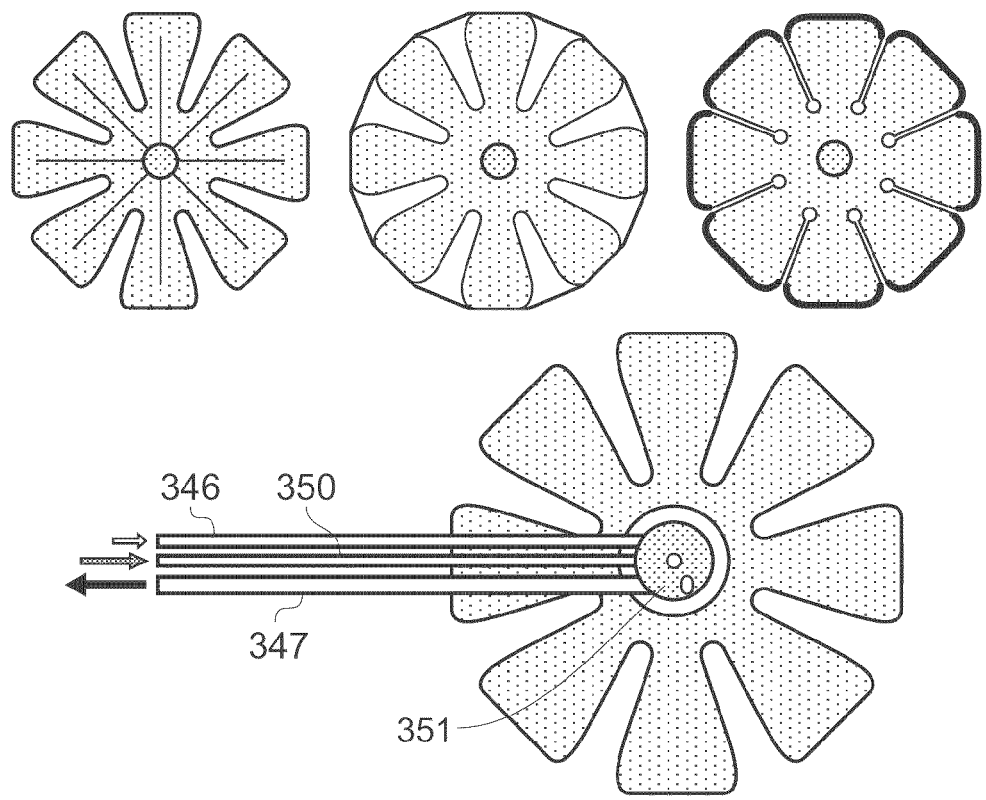

This is defined by an upper impervious membrane (361) and a lower porous film (362) with apertures (364) that deliver the irrigant fluid directly to the wound bed over an extended area, and thus effectively forms an inlet manifold. Three configurations of the chamber (363) are shown in FIG. 27b, all of which are able to conform well to the wound bed by the arms closing in and possibly overlapping in insertion into the wound.

The space above the chamber (363) is filled with a wound filler (348) under the backing layer (342). This comprises an oblately spheroidal conformable hollow body, defined by a membrane (349) that is filled with a fluid, here air or nitrogen, that urges it to the wound shape. An inflation inlet pipe (350) is mounted centrally in a first boss (351) in the backing layer (342) above the hollow body (348). The inflation inlet pipe (350) communicates with the interior of the hollow body (348), to permit inflation of the body (348). Again, this inflation of the hollow body (348) is conveniently a means to apply stress to the wound.

A moulded hat-shaped boss (351) is mounted centrally on the upper impervious membrane (361) of the chamber (363). It has three internal channels, conduits or passages through it (not shown), each with entry and exit apertures. The filler (348) is attached to the membrane (361) of the chamber (363) by adhesive, heat welding or a mechanical fixator, such as a cooperating pin and socket.

An inflation inlet pipe (350), inlet pipe (346) and outlet pipe (347) pass under the edge of the proximal face of the backing layer (342) of the dressing.

They extend radially immediately under the filler (348) and over the membrane (361) of the chamber (363) to each mate with an entry aperture in the boss (351).

An exit to the internal channel, conduit or passage through it that receives the inflation inlet pipe (350) communicates with the interior of the hollow filler (348), to permit inflation.

An exit to the internal channel, conduit or passage that receives the inlet pipe (346) communicates with the interior of the chamber (363) to deliver the irrigant fluid via the chamber (363) to the wound bed over an extended area.

Similarly, an exit to the internal channel, conduit or passage that receives the outlet pipe (347) communicates with the space above the chamber (363) and under the wound filler (348), and collects flow of irrigant and/or wound exudate radially from the wound periphery.

Figure 28:
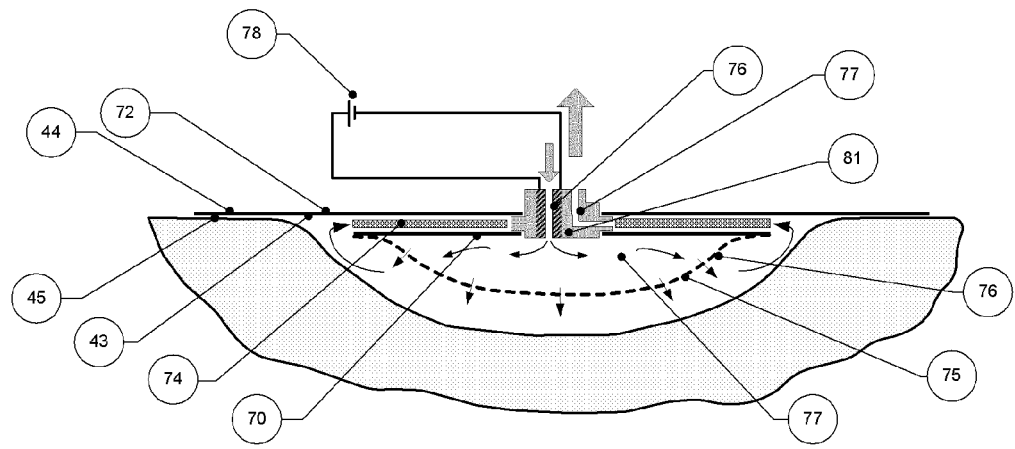
FIGS. 28 to 30 are cross-sectional views of conformable wound dressings, for aspirating and/or irrigating wounds.

Referring to FIG. 28, one form of the dressing comprises a circular sheet (70) that lies under a circular backing layer (72) and is permanently attached to a boss (81), which is e.g. heat-sealed to the backing layer (72).

An annular layer of foam (74) formed of a suitable material, e.g. a resilient thermoplastic, preferably a reticulated filtration polyurethane foam with small apertures or pores, spaces the sheet (70) from the backing layer and surrounds the boss (81).

A downwardly dished membrane (75) with openings (76) is permanently attached to the sheet (70) by heat-sealing to form a chamber (77) with the sheet (70).

An inlet pipe (76) and outlet pipe (77) are mounted centrally in the boss (81) and pass through the backing layer (72).

The inlet pipe (76) is made of a polyurethane tubular core (not shown) surrounded by an annulus of resistive conductive material, such as one of the resistive alloys noted hereinbefore, which generates thermal energy when a voltage drop is applied over it. It is connected to a cell (78), shown schematically, which applies a voltage drop over it.

The inlet pipe (76) communicates with the interior of the chamber (77), which thus forms an inlet manifold that distributes heated fluid directly to the wound when the dressing is in use.

The outlet pipe (77) extends radially immediately under the backing layer (3) and communicates with the inner face of the layer of foam (74), which forms an outlet manifold.

This form of the dressing is a more suitable layout for shallow wounds

Figure 29:
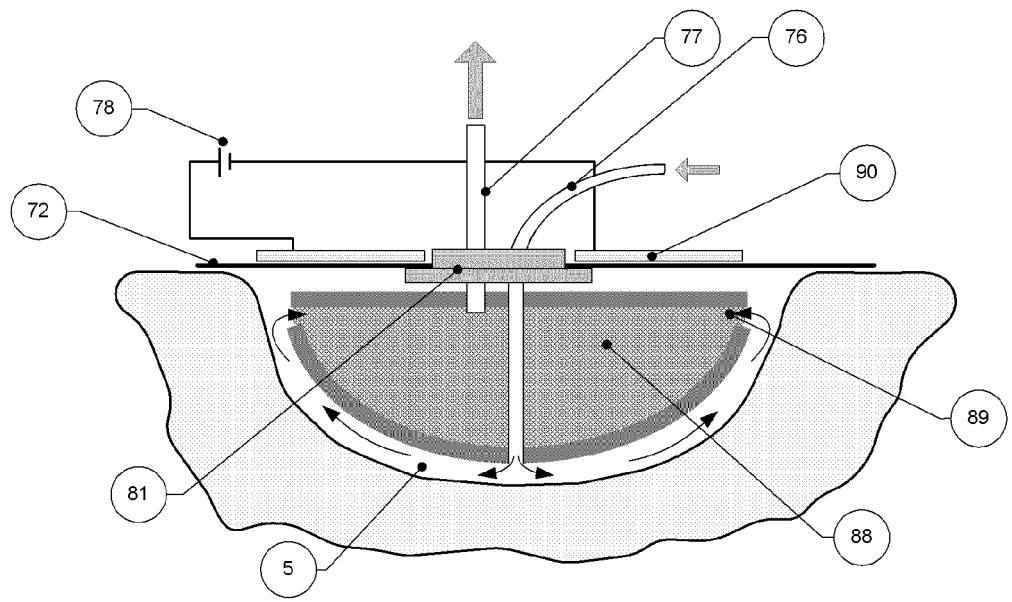

Another form of dressing is shown in FIG. 29. An inlet pipe (76) and outlet pipe (77) are mounted centrally in a boss (81) in, and pass through a backing layer (72). An oblately hemispheroidal filler (88) with an annular groove (89) may be permanently attached to the pipes (76) and (77).

It is formed of a suitable material, e.g. a resilient thermoplastic foam, preferably a reticulated filtration polyurethane foams with small apertures or pores.

An annular electrical heat pad (90) is mounted around the boss (81) on top of the backing layer (3), which is capable of conducting heat to the wound (5) through the irrigant.

It may be in the form of non-woven or woven fabric, such as a woven layer or sheet of carbon fibres or a fabric, such as a woven layer or sheet made essentially of carbonised acrylate, such as polyacrylonitrile and copolymers thereof, which generate thermal energy when a voltage drop is applied over it.

Alternatively, it may be an electrically insulating flat sheet or membrane substrate that has an electrically resistive but conductive printed circuit on it. It is connected to a cell (78), shown schematically, which applies a voltage drop over it.

The inlet pipe (76) communicates with the wound space at the lowest point of the filler (88). The outlet pipe (77) communicates with the groove (89), and effectively collects the fluid from the wound periphery when the dressing is in use.

This form of the dressing is a more suitable layout for deeper wounds.

Figure 30:
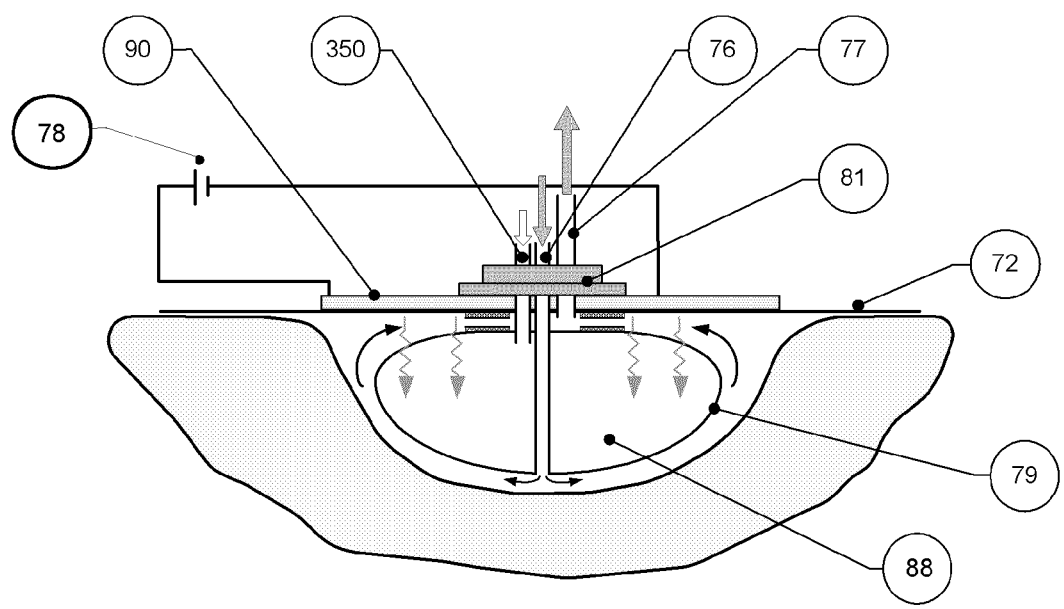

In FIG. 30, an inlet pipe (76) and outlet pipe (77) are mounted centrally in a boss (81) in, and pass through a backing layer (72). An oblately spheroidal conformable hollow body (78) is defined by a membrane (79) which is filled with a fluid, here air or nitrogen, that urges it to the wound shape, and is permanently attached to the pipes (76) and (77).

It is formed of a suitable material, e.g. a resilient thermoplastic, preferably a reticulated filtration polyurethane foam with small apertures or pores.

The inflation inlet pipe (350) communicates with the interior of the hollow body (78), to permit inflation of the body (78). The inlet pipe (76) extends through the hollow body (78). The outlet pipe (77) communicates with an outlet manifold formed by a series of radial apertures in a foam disc immediately under the backing layer, that collects the fluid from the wound periphery when the dressing is in use.

An electrical heater (90) is mounted under the boss (81) on top of the backing layer (3), which is transparent to radiant heat, and so permit its transmission to the wound (5) through the irrigant.

It may be in the form of a near infrared radiant heater which generates thermal energy when a voltage drop is applied over it. It is connected to a cell (78), shown schematically, which applies a voltage drop over it.

Figure 31A:
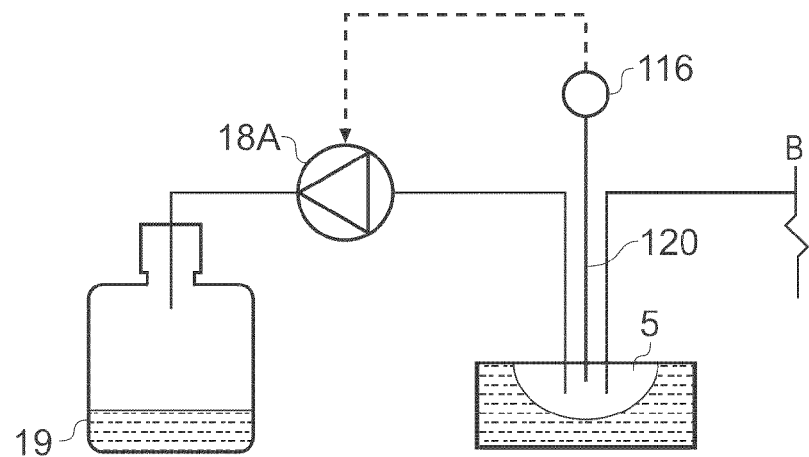
FIGS. 31a and b are variants of a two-pump system with essentially identical, and identically numbered, components as in FIG. 11. However, they have alternative means for handling the aspirate flow to the aspirate collection vessel under negative or positive pressure to the wound in simultaneous aspiration and irrigation of the wound, including in FIG. 31b a third device for moving fluid into a waste bag.

Referring to FIG. 31a, this shows another alternative layout of the essentially identical, and identically numbered, components in FIG. 11a downstream of point B, and alternative means for handling the aspirate flow to the aspirate collection vessel under negative or positive pressure to the wound. The pressure monitor (116) is connected to a monitor offtake tube (120) and has a feedback connection to a variable-speed first device (18A), here a variable-speed pump, upstream of the aspirate collection vessel (19), and the filter (119) and the air aspiration tube (113) are omitted. This provides means for aspirate flow regulation and for holding the low negative pressure on the wound at a steady level. The operation of the apparatus is as described hereinbefore.

Figure 31B:
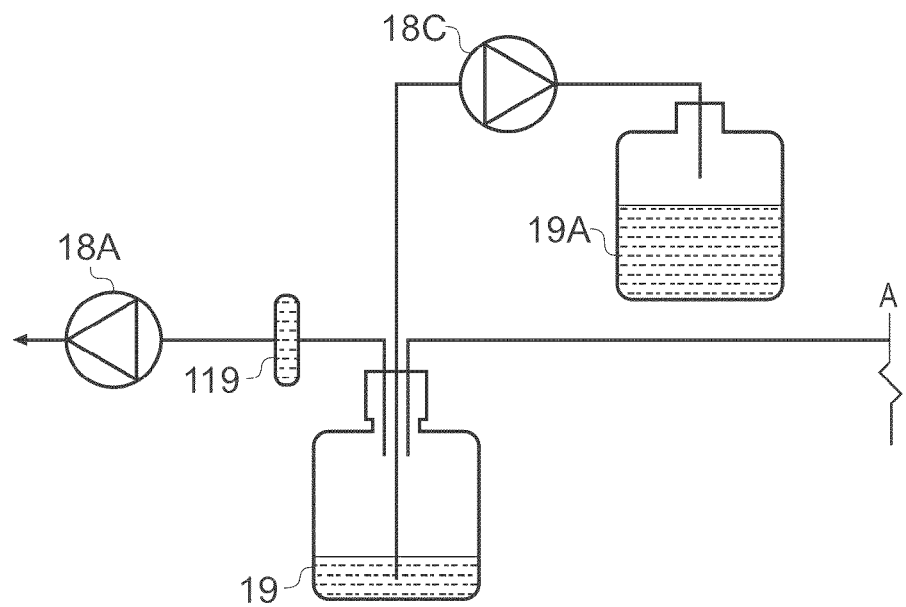

Referring to FIG. 31b, this shows another alternative layout of the essentially identical, and identically numbered, components in FIG. 11a downstream of point A, and alternative means for handling the aspirate flow to the aspirate collection vessel under negative or positive pressure to the wound. The pressure monitor (116) is omitted, as is the feedback connection to a variable-speed first device (18A), here a variable-speed pump, downstream of the aspirate collection vessel (19) and the filter (119).

A third device (18C), here a fixed-speed pump, provides means for moving fluid from the aspirate collection vessel (19) into a waste bag (19A). The operation of the apparatus is as described hereinbefore.

Figure 32:
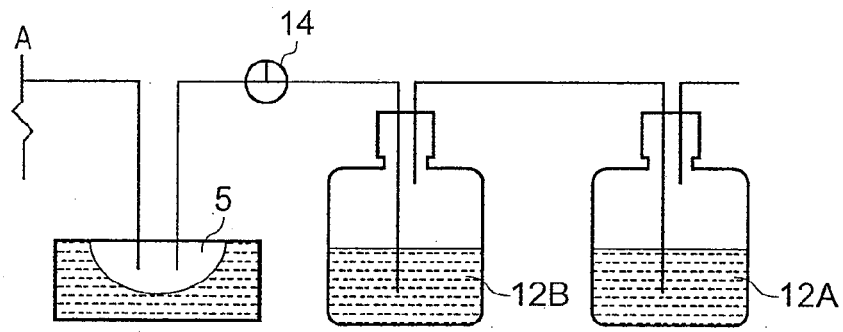
FIG. 32 is a single-pump system essentially with the omission from the apparatus of FIG. 11 of the second device for moving irrigant fluid into the wound dressing.

Referring to FIG. 32, this shows an alternative layout of the essentially identical, and identically numbered, components in FIG. 11a upstream of point A.

It is a single-pump system essentially with the omission from the apparatus of FIG. 11A of the second device for moving irrigant fluid into the wound dressing. The operation of the apparatus is as described hereinbefore.

Figure 33:
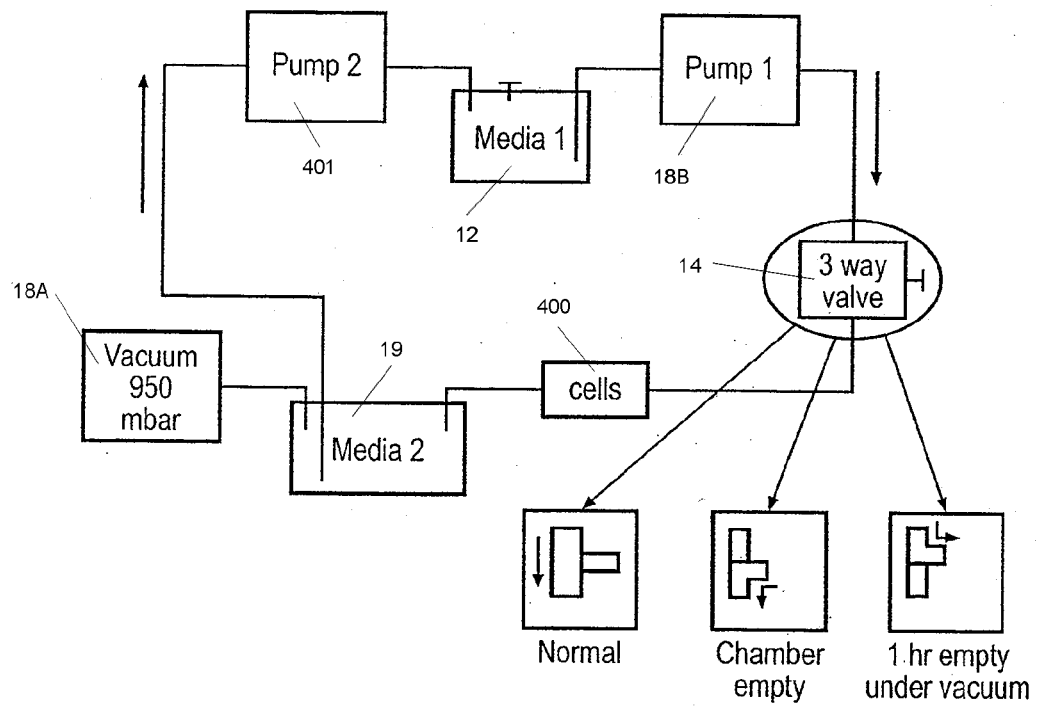
FIG. 33 shows a schematic representation of a simultaneous irrigate/aspirate (SIA) and sequential irrigate/aspirate (SEQ) flow system. This system may be used to assess the effects of flow stress in wound healing.

Referring to FIG. 33, a suitable apparatus for assessing the effect of flow stress on cells in a simulated wound is shown.

A pump (18b) pumps irrigation fluid from a reservoir (12) through a 3 way valve (14) which can be configured to allow normal continuous flow, emptying of the test chamber (400) under vacuum, or emptying of the test chamber (400) at atmospheric pressure.

The irrigation fluid passes into a test chamber (400) described in more detail later. The aspirate leaving the test chamber (400) passes into a waste reservoir (19).

A source of vacuum (18A) manifolds the system at a vacuum (950 mbar) and draws the aspirate into the waste reservoir (19). An additional pump (401) recycles the aspirate from the waste reservoir (19) back to the irrigant reservoir (12). This is suitable for an in vitro system, but would generally be unsuitable for treatment of a patient where the aspirate would contain quantities of deleterious compounds. In such cases a system wherein the vacuum (401) is used would be suitable as the waste aspirant is not recycled.

EXAMPLES

The use of the apparatus of the present invention will now be described by way of example only in the following Examples:

Example 1

Removal of wound proteins and derivatives with a two-pump apparatus.

In this example, a gelatine sheet laid in a cavity wound model represents wound proteins and derivatives to be removed by the two-pump apparatus. The dressing is essentially identical with that in FIG. 18, i.e. it comprises a circular backing layer and a lobed chamber in the form of a deeply indented disc much like a multiple Maltese cross or a stylised rose, defined by an upper impervious membrane and a lower porous film with apertures that deliver the irrigant fluid directly from the wound bed over an extended area.

A two-pump system was set up essentially as in FIG. 2, with (a) an irrigant dispensing bottle—1000 ml Schott Duran, connected to (b) a peristaltic pump (Masterflex) for irrigant delivery, and associated power supply and supply tube, (c) a diaphragm vacuum pump (Schwarz) for aspiration, and associated power supply and offtake tube, connected to (d) a vacuum vessel (aspirate collection jar)—Nalgene 150 ml polystyrene, (e) each pump being connected to a dressing consisting of the following elements: (i) a wound contacting element, comprising a lobed bag with low porosity 'leaky' membrane scaffold on the lower surface, impermeable film on the top, and a foam spacer between the two layers to allow free flow of irrigant solution; (ii) a space filling element, comprising a reticulated, open-cell foam (black reticulated foam, Foam Techniques) 30 mm thick, 60 mm diameter; (iii) an occlusive adhesive coated polyurethane backing layer top film (Smith & Nephew Medical) with acrylic pressure sensitive adhesive; (iv) two tubes passing under the occlusive top film, and sealed to prevent leakage of gas or liquid: one tube centrally penetrating the top film of the wound-contacting element to deliver irrigant into the chamber formed by this film and the porous element; the other tube of approximately equal length to remove aspirate with the opening positioned just above the top film of the wound contacting element.

Preparation of Gelatine Sheet

A 20% aqueous solution of gelatine was prepared by weighing gelatine into a glass jar and making it up to the required weight with deionized water. The jar was placed in an oven (Heraeus), at set temperature 85° C. After 60 minutes the jar was removed from the oven and shaken, to encourage mixing. Petri dishes were partially filled with 10 g quantities of the gelatine solution and placed in a fridge (LEC, set temperature: 4° C.) to set for at least 1 hour. Final thickness of the gelatine slab was ~5 mm. Petri dishes containing the gelatine slabs were removed from the fridge at least 2 hours before use.

Preparation of Test Equipment and Materials

Irrigant solution (deionized water) and the Perspex wound model were pre-conditioned in an oven (Gallenkamp) at set temperature 37° C., for at least 4 hours before use.

For each test, a freshly prepared gelatine slab was removed from a Petri dish and weighed.

The Perspex wound model was then removed from the oven and the gelatine slab placed at the bottom of the cavity. Application of the dressing to the wound model was as follows: (a) the wound contacting element was carefully placed over the gelatine slab; (b) the foam filler was placed on top of this with the irrigant and aspirate tubes running centrally to the top of the cavity (the foam filler was slit to the center to facilitate this); (c) the side entry port, pre-threaded onto the tubes, was adhesively bonded to the upper surface of the wound model block using an acrylic pressure sensitive adhesive; (d) the top adhesive coated film was applied over all of the elements and pressed down to give a seal on all sides, and especially around the tube entry/exit point.

Application of the dressing to the wound model was the same for all tests performed. All tubing used was the same for each experiment (e.g. material, diameter, length).

Simultaneous Irrigation & Aspiration

A schematic diagram of the system used in the experiment is shown below. For the experiment most of the apparatus (not including the pumps, power supply, and connecting tubing to and from the pumps) was placed in an oven (Gallenkamp, set temperature: 37° C.), on the same shelf.

Before starting the irrigation pump a vacuum was drawn on the system to check that the dressing and tube connections were substantially airtight (the pumping system was controlled to give a pressure at the vacuum vessel of approximately ~75 mmHg before opening the system up to include the dressing).

Once system integrity had been confirmed, the irrigation pump was started (nominal flow rate: 50 ml/hr), i.e. both pumps running together. Timing of the experiment was started when the advancing water front within the irrigant tube was observed to have reached the top of the dressing.

After 60 minutes, the irrigation pump was stopped, shortly followed by the vacuum (aspiration) pump.

Aspirate liquid collected in the vacuum jar was decanted into a glass jar. The vacuum jar was rinsed with ~100 ml of deionized water and this added to the same glass jar.

The aspirate solution was placed in an oven (Heraeus, set temperature: 130° C.) and dried to constant weight.

Sequential Irrigation & Aspiration

The experimental set up was as for the simultaneous irrigation/aspiration experiment.

Before starting the experiment a vacuum was pulled on the system to check that the dressing and tube connections were substantially airtight. The pumping system was controlled to give a pressure at the vacuum vessel of approximately ~75 mmHg before opening the system up to include the dressing. Once system integrity had been confirmed, the irrigation pump was started (nominal rate: 186 ml/hr) and run until the advancing water front in the irrigant tube was observed to have reached the top of the dressing.

The pump was temporarily stopped at this point whilst the vacuum line was sealed (using a tube clamp) and the vacuum pump stopped.

Timing of the experiment was from the point the irrigation pump was restarted. The pump was run until 50 ml of irrigant had entered the wound model (just over 16 minutes at the rate of 186 ml/hr). At this point the irrigant pump was stopped.

It was observed that during the filling phase of sequential filling and flushing, air trapped in the model wound cavity caused the top film of the dressing to inflate substantially, to a point approaching failure.

After a further ~44 minutes (60 minutes from the start of the experiment) the vacuum pump was started and the tube clamp on the aspirate line removed. The wound model was aspirated for 5 minutes. Towards the end of this period a small leak was introduced into the top film of the dressing to maximize the amount of fluid drawn from the wound model (it was observed that as the pressure differential between the wound model cavity and the vacuum jar reduced to zero, the flow of aspirate also tended to slow. Introducing a small leak re-established the pressure differential and the flow of aspirate out of the cavity).

Results and Conclusions

| Simultaneous Irrigation & Aspiration | | | |
|---|---|---|---|
| Reference number | Aspirate recovered (g) | Recovery of gelatine (%) | Concentration of gelatine in aspirated fluid (% w/w) |
| 1 | 48.81 | 79.33 | 3.27 |
| 2 | 45.64 | 72.30 | 3.18 |
| 3 | 48.84 | 68.05 | 2.76 |
| Mean | 47.76 | 73.22 | 3.07 |

| Sequential Irrigation & Aspiration Cycle | | | |
|---|---|---|---|
| Reference number | Aspirate recovered (g) | Recovery of gelatine (%) | Concentration of gelatine in aspirated fluid (% w/w) |
| 1 | 32.08 | 19.59 | 1.23 |
| 2 | 34.09 | 18.35 | 1.07 |
| 3 | 33.90 | 10.77 | 0.64 |
| Mean | 33.36 | 16.24 | 0.98 |

Simultaneously irrigating and aspirating the wound model removed more of the gelatine placed at the base of the wound model cavity than sequentially filling and emptying the cavity, even though the amount of liquid entering the wound and the duration of the experiment were the same in both cases.

Simultaneously irrigating and aspirating also removed more fluid from the model wound.

Example 2

The combination of simultaneous fluid flow (irrigation) and aspiration (under reduced pressure) on wound bed fibroblasts compared with the exposure of wound bed fibroblasts to repeated fill-empty cycles of fluid flow and aspiration.

An apparatus of the present invention was constructed essentially as in FIG. 33, which is an apparatus where an irrigant is delivered continually to the wound bed and the resultant wound exudate/fluid mixture is at the same time continually aspirated from the wound. Alternative systems are known where the wound is subjected to repeated iteration of a cycle of fluid delivery followed by a period of aspiration under reduced pressure.

The apparatus comprised a surrogate wound chamber (Minucells perfusion chamber) in which normal diploid human fibroblasts were cultured on 13 mm diameter (Thermanox polymer) cover slips retained in a two part support (Minucells Minusheets). Tissues present in the healing wound that must survive and proliferate were represented by the cells within the chamber. Nutrient medium (DMEM with 10% FCS with 1% Buffer All) to simulate an irrigant fluid/wound exudate mixture, was pumped from a reservoir into the lower aspect of the chamber where it bathed the fibroblasts and was removed from the upper aspect of the chamber and returned to a second reservoir. The wound chamber was maintained at less than atmospheric pressure by means of a vacuum pump in line with the circuit.

The pumps for the circuit were peristaltic pumps acting on silicone (or equivalent) elastic tubing. The circuit was exposed to a vacuum of no more than 10% atmospheric pressure, 950 mbar and atmospheric pressure varied up to a maximum value of 1044 mbar. The internal diameter of the tubing was 1.0 mm. A total volume for the circuit including the chamber and the reservoir of between 50 and 220 ml was used. The flow rates used were at a number of values between 0.1 ml min$^{-1}$ and 2.0 ml$^{-1}$ min$^{-1}$.

An experiment was conducted that simulated conditions that are not uncommon for healing wounds whereby a fluid was delivered to the wound bed and the application of a vacuum was used to remove the mixture of fluid and exudate to a waste reservoir.

An air bleed fluid control valve was additionally positioned in the circuit so that on opening the air bleed occurred for a time and closed the fluid flow, the simulated irrigant fluid/wound exudate mixture was evacuated from the chamber and the fibroblasts were maintained under a negative pressure relative to the atmosphere. This represents an empty/fill system.

Results and Conclusions

The following results were obtained for a circuit comprising a wound chamber as above containing a total volume of nutrient media (154 ml) pumped at a flow rate of 0.2 ml min-1 and where vacuum was set at 950 mbar and where atmospheric pressure varied up to a maximum value of 1044 mbar. The wound chamber and media were held at 37° C. for 25 hours. In one set of wound chambers continuous flow was maintained. In a second set of chambers 6 cycles of empty/fill were performed with each fill or empty phase lasting 1 hour.

In controls where empty/fill system with 6× cycles of 1 hour empty/1 hour fill over a total of 25 hours, the survival and growth of the fibroblasts is inhibited.

However, when the nutrient medium flow in the first circuit is delivered continually to the Minucells chamber and the resultant nutrient medium is at the same time continually aspirated from the Minucells chamber under vacuum was set at 950 mbar and where atmospheric pressure varied up to a maximum value of 1044 mbar, the fibroblasts survive and proliferate to a greater extent during a 25 hour period than the control empty/fill circuits

| Conditions | Mean relative level of cell activity* after 25 hours. |
|---|---|
| Baseline cell activity prior to introduction to wound chamber | 100% |
| Fill empty 6 cycles | 93% |
| Continuous flow | 143% |

*Cell activity measured with a WST (Tetrazolium based mitochondrial dehydrogenase activity assay). Data normalised to fibroblasts seeded onto coverslips with normal nutrient media baseline activity The combination of continuous fluid flow at 0.2 ml min$^{-1}$ and waste fluid removal under vacuum of no more than 10% atmospheric pressure, 950 mbar and atmospheric pressure varied up to a maximum value of 1044 mbar, enhances the cell response necessary for wound healing more than the fill empty fill pattern under vacuum.

Example 3

Removal of wound proteins and heating a wound with a two-pump apparatus.

In this example, a gelatine sheet laid in a cavity wound model represents wound proteins and derivatives to be removed by the two-pump apparatus.

The dressing is essentially identical with that in FIG. 28, i.e. a form of the dressing with an inlet pipe surrounded by an annulus of resistive conductive material, which is connected to a cell via a circuit with a current control and a switch, and generates thermal energy when a voltage drop is applied over it by the cell.

The inlet pipe communicates with the interior of an inlet manifold that distributes heated fluid directly to the wound when the dressing is in use.

A two-pump system is set up essentially as in FIG. 2, with an irrigant dispensing bottle—1000 ml Schott Duran, connected to a peristaltic pump (Masterflex) for irrigant delivery, and associated power supply and supply tube, a diaphragm vacuum pump (Schwarz) for aspiration, and associated power supply and offtake tube, connected to a vacuum vessel (aspirant collection jar)—Nalgene 150 ml polystyrene, each pump being connected to a dressing consisting of the following elements: wound-contacting element, comprising a lobed bag with low porosity 'leaky' membrane scaffold on the lower surface, impermeable film on the top, and a foam spacer between the two layers to allow free flow of irrigant solution, a space filling element, comprising a reticulated, open-cell foam (black reticulated foam, Foam Techniques) 30 mm thick, 60 mm diameter, an occlusive adhesive coated polyurethane backing layer top film (Smith & Nephew Medical) with acrylic pressure sensitive adhesive, two tubes passing under the occlusive top film, and sealed to prevent leakage of gas or liquid: one tube centrally penetrating the top film of the wound-contacting element to deliver irrigant into the chamber formed by this film and the porous element; the other tube of approximately equal length to remove aspirant with the opening positioned just above the top film of the wound contacting element.

Pressure Sensor in Wound Model Cavity

Temperature Sensor in Wound Model Cavity

Preparation of Gelatine Sheet:

A 20% aqueous solution of gelatine is prepared by weighing gelatine into a glass jar and making it up to the required weight with deionized water. The jar is placed in an oven (Heraeus), at set temperature 85° C.

After 60 minutes the jar is removed from the oven and shaken, to encourage mixing. Petri dishes are partially filled with 10 g quantities of the gelatine solution and placed in a fridge (LEC, set temperature: 4° C.) to set for at least 1 hour. Final thickness of the gelatine slab is ~5 mm. Petri dishes containing the gelatine slabs are removed from the fridge at least 2 hours before use.

Preparation of Test Equipment and Materials

Irrigant solution (deionized water) and the Perspex wound model are pre-conditioned in an oven (Gallenkamp) at set temperature 37° C., for at least 4 hours before use.

For each test, a freshly prepared gelatine slab is removed from a Petri dish and weighed. The Perspex wound model is then removed from the oven and the gelatine slab placed at the bottom of the cavity. Application of the dressing to the wound model is as follows: (i) the wound contacting element is carefully placed over the gelatine slab; (ii) the foam filler is placed on top of this with the irrigant and aspirant tubes running centrally to the top of the cavity (the foam filler is slit to the center to facilitate this); (iii) the side entry port, pre-threaded onto the tubes, is adhesively bonded to the upper surface of the wound model block using an acrylic pressure sensitive adhesive; (iv) the top adhesive coated film is applied over all of the elements and pressed down to give a seal on all sides, and especially around the tube entry/exit point.

Application of the dressing to the wound model is the same for all tests performed. All tubing used is the same for each experiment (e.g. material, diameter, length).

Simultaneous Irrigation & Aspiration

A schematic diagram of the system used in the experiment is shown below. For the experiment most of the apparatus (not including the pumps, power supply, and connecting tubing to and from the pumps) is placed in an oven (Gallenkamp, set temperature: 37° C.), on the same shelf.

Before starting the irrigation pump a vacuum is drawn on the system to check that the dressing and tube connections are substantially airtight.

The pumping system is controlled to give a pressure at the vacuum vessel of approximately −75 mmHg before opening the system up to include the dressing).

Once system integrity has been confirmed, the irrigation pump is started (nominal flow rate: 50 ml/hr), i.e. both pumps running together.

The means for supplying thermal energy to the fluid in the wound in the present apparatus is then activated, i.e. the switch is closed, so that a voltage drop is applied over the annulus of resistive conductive material, and it generates thermal energy, which is conducted to the irrigant liquid passing through the inlet pipe into the manifold chamber. The current control is adjusted to maintain a temperature at the wound bed under the wound-facing face of the backing layer of the wound dressing at a constant level throughout the experiment of 36 to 38° C.

Timing of the experiment is started when the advancing water front within the irrigant tube is observed to have reached the top of the dressing.

After 60 minutes, the means for supplying thermal energy to the fluid in the wound in the present apparatus is deactivated, i.e. the switch is opened, so that a voltage drop is no longer applied over the annulus of resistive conductive material.

The irrigation pump is stopped, shortly followed by the vacuum (aspiration) pump. Aspirant liquid collected in the vacuum jar is decanted into a glass jar. The vacuum jar is rinsed with ~100 ml of deionized water and this added to the same glass jar. The aspirant solution is placed in an oven (Heraeus, set temperature: 130° C.) and dried to constant weight.

Sequential Irrigation & Aspiration

The experimental set up is as for the simultaneous irrigation/aspiration experiment. Before starting the experiment a vacuum is pulled on the system to check that the dressing and tube connections are substantially airtight.

The pumping system is controlled to give a pressure at the vacuum vessel of approximately −75 mmHg before opening the system up to include the dressing.

Once system integrity has been confirmed, the irrigation pump is started (nominal rate: 186 ml/hr) and the means for supplying thermal energy to the fluid in the wound in the present apparatus is then activated, i.e. the switch is closed, so that a voltage drop is applied over the annulus of resistive conductive material. The current control is adjusted to maintain a temperature at the wound bed under the wound-facing face of the backing layer of the wound dressing at a constant level throughout the experiment of 36 to 38° C.

The pump is run until the advancing water front in the irrigant tube is observed to have reached the top of the dressing.

The pump is temporarily stopped at this point whilst the vacuum line is sealed (using a tube clamp) and the vacuum pump stopped.

Timing of the experiment is from the point the irrigation pump is restarted. The pump is run until 50 ml of irrigant has entered the wound model (just over 16 minutes at the rate of 186 ml/hr). At this point the means for supplying thermal energy to the fluid in the wound in the present apparatus is deactivated, i.e. the switch is opened, so that a voltage drop is no longer applied over the annulus of resistive conductive material. The irrigant pump is stopped.

It is observed that during the filling phase of sequential filling and flushing, air trapped in the model wound cavity caused the top film of the dressing to inflate substantially, to a point approaching failure.

After a further ~44 minutes (60 minutes from the start of the experiment) the vacuum pump is started and the tube clamp on the aspirant line removed. The wound model is aspirated for 5 minutes.

Towards the end of this period a small leak is introduced into the top film of the dressing to maximize the amount of fluid drawn from the wound model (it is observed that as the pressure differential between the wound model cavity and the vacuum jar reduced to zero, the flow of aspirant also tended to slow. Introducing a small leak re-established the pressure differential and the flow of aspirant out of the cavity).

Results and Conclusions

Using the present apparatus with its means for supplying thermal energy to the fluid in the wound, one is able to achieve and maintain a temperature at the wound bed under the wound-facing face of the backing layer of the wound dressing at a constant level of 36 to 38° C., while simultaneously irrigating and aspirating the wound model with programmable fluid movement.

Simultaneously irrigating and aspirating also removes more of the surrogate wound protein sheet placed at the base of the wound model cavity than sequentially filling and emptying the cavity, even though the amount of liquid entering the wound and the duration of the experiment are the same in both cases. Simultaneously irrigating and aspirating also removes more fluid from the model wound.

Example 4

The combination of simultaneous warmed fluid flow (irrigation) and aspiration (under reduced pressure) on wound bed fibroblasts compared with the exposure of wound bed fibroblasts to repeated fill-empty cycles of warmed fluid flow and aspiration.

An apparatus of the present invention was constructed essentially as in FIG. 33, which is an apparatus where an irrigant or fluid of some nature is delivered continually to the wound bed and the resultant wound exudate/fluid mixture is at the same time continually aspirated from the wound. Alternative systems are known where the wound is subjected to repeated iteration of a cycle of fluid delivery followed by a period of aspiration under reduced pressure.

The apparatus comprised a surrogate wound chamber (Minucells perfusion chamber) in which normal diploid human fibroblasts were cultured on 13 mm diameter (Thermanox polymer) cover slips retained in a two part support (Minnucells Minusheets). Tissues present in the healing wound that must survive and proliferate were represented by the cells within the chamber. Nutrient medium (DMEM with 10% FCS with 1% Buffer All) to simulate an irrigant fluid/wound exudate mixture, was pumped from a reservoir into the lower aspect of the chamber where it bathed the fibroblasts and was removed from the upper aspect of the chamber and returned to a second reservoir. The wound chamber was maintained at less than atmospheric pressure by means of a vacuum pump in line with the circuit.

The pumps for the circuit were peristaltic pumps acting on silicone (or equivalent) elastic tubing.

The circuit was exposed to a vacuum of no more than 10% atmospheric pressure, 950 mbar and atmospheric pressure varied up to a maximum value of 1044 mbar. The internal diameter of the tubing was 1.0 mm. A total volume for the circuit including the chamber and the reservoir of between 50 and 220 ml was used. The flow rates used were at a number of values between 0.1 ml min$^{-1}$ and 2.0 ml$^{-1}$ min$^{-1}$.

First circuit also comprised: upstream of the wound chamber, a heat exchanger such that the temperature of the nutrient media bathing the cells reaches between 35° C. and 37° C.

Experiments were conducted that simulated conditions not uncommon for healing wounds whereby the chamber simulating the wound was placed in a room temperature environment (simulating the low temperatures often experienced in wounds where blood flow is poor), additional chambers heated such that the cells reaches between 35° C. and 37° C.

An experiment was conducted that simulated conditions that are not uncommon for healing wounds whereby a fluid was delivered to the wound bed and the application of a vacuum is used to remove the mixture of fluid and exudate to a waste reservoir. An air bleed fluid control valve was additionally positioned in the circuit so that on opening the air bleed occurred for a time and closed the fluid flow, the simulated irrigant fluid/wound exudate mixture was evacuated from the chamber and the fibroblasts were maintained under a negative pressure relative to the atmosphere. This represents an empty/fill system. 6 cycles of empty/fill were performed with each fill or empty phase lasting 1 hour.

Apparatus was also constructed essentially as in FIG. 33, but where either (a) it was was operated as an empty/fill system with 6× cycles of 1 hour empty/1 hour fill over a total of 25 hours, or (b) the heat exchanger is omitted, so that the nutrient flow bathing the cells does not reach between 35° C. and 37° C. and remains at between 18° C. and 20° C.

Results and Conclusions

The following results were obtained for a circuit comprising a wound chamber as above containing a total volume of nutrient media (154 ml) pumped at a flow rate of 0.2 ml min$^{-1}$ and where vacuum was set at 950 mbar and where atmospheric pressure varied up to a maximum value of 1044 mbar. The wound chamber and media were held at 37° C. for 25 hours. In one set of wound chambers continuous flow was maintained. In a second set of chambers 6 cycles of empty/fill were performed with each fill or empty phase lasting 1 hour.

In controls where either (a) it was operated as an empty/fill system with 6× cycles of 1 hour empty/1 hour fill over a total of 25 hours, (b) the heat exchanger unit is omitted; the survival and growth of the fibroblasts is inhibited.

However, when the nutrient medium flow in the first circuit is (a) is delivered continually to the minucell chamber and the resultant nutrient medium is at the same time continually aspirated from the minucell chamber under vacuum was set at 950 mbar and where atmospheric pressure varied up to a maximum value of 1044 mbar, (b) And passes through a heat exchanger so that the temperature of the nutrient media bathing the cells reaches between 35° C. and 37° C.; the fibroblasts survive and proliferate to a greater extent during a 25 hour period than the control empty/fill circuits.

| Conditions | Mean of cell activity* after 25 hours. N = 3 |
|---|---|
| Baseline cell activity prior to introduction to wound chamber | 0.25 |
| Continuous flow (SIA) flow at room temperature | 0.39 |
| Continuous flow (SIA) plus heat (37° C.) | 0.45 |
| Fill empty 6 cycles at room temperature | 0.24 |
| Fill empty 6 cycles plus heat (37° C.) | 0.38 |

*Cell activity measured with a WST (Tetrazolium based mitochondrial dehdrogenase activity assay).

The combination of heat (37° C.) and continuous fluid flow at 0.2 ml min$^{-1}$ with waste fluid removal under vacuum of no more than 10% atmostpheric pressure, 950 mbar and atmospheric pressure varied up to a maximum value of 1044 mbar, enhances the cell response necessary for wound healing more than the fill empty fill pattern under vacuum.

Example 5

Removal of adherent bacteria and debris with a two-pump apparatus.

In this example, a culture medium sheet containing nutritional supplements with an adherent bacterial culture of *Staphylococcus aureus* on its top surface is laid in a cavity wound model to represent adherent bacteria and debris on a wound bed to be removed by the two-pump apparatus.

The dressing is essentially identical with that in FIG. 18, i.e. it comprises a circular backing layer and a lobed chamber in the form of a deeply indented disc much like a multiple Maltese cross or a stylised rose, defined by an upper impervious membrane and a lower porous film with apertures that deliver the irrigant fluid directly from the wound bed over an extended area.

The irrigant supplied to the wound dressing under a negative pressure on the wound bed contains a therapeutically active amount of an antibacterial agent, selected from chlorhexidine, povidone iodine, triclosan, metronidazole, cetrimide and chlorhexidine acetate.

A two-pump system is set up essentially as in FIG. 2, with an irrigant dispensing bottle—1000 ml Schott Duran, connected to a peristaltic pump (Masterflex) for irrigant delivery, and associated power supply and supply tube, a diaphragm vacuum pump (Schwarz) for aspiration, and associated power supply and offtake tube, connected to a vacuum vessel (aspirant collection jar)—Nalgene 150 ml polystyrene each pump being connected to a dressing consisting of the following elements: wound-contacting element, comprising a lobed bag with low porosity 'leaky' membrane scaffold on the lower surface, impermeable film on the top, and a foam spacer between the two layers to allow free flow of irrigant solution, a space filling element, comprising a reticulated, open-cell foam (black reticulated foam, Foam Techniques) 30 mm thick, 60 mm diameter, an occlusive adhesive coated polyurethane backing layer top film (Smith & Nephew Medical) with acrylic pressure sensitive adhesive, two tubes passing under the occlusive top film, and sealed to prevent leakage of gas or liquid: one tube centrally penetrating the top film of the wound-contacting element to deliver irrigant into the chamber formed by this film and the porous element; the other tube of approximately equal length to remove aspirant with the opening positioned just above the top film of the wound contacting element.

Preparation of Agar Culture Medium Sheet with Adherent *Staphylococcus Aureus* Culture An aqueous solution of agar culture medium is prepared by weighing agar culture medium containing nutritional supplements into a glass jar and making it up to the required weight with deionized water. The jar is placed in an oven (Heraeus), at a set temperature. After 60 minutes the jar is removed from the oven and shaken, to encourage mixing.

Petri dishes are partially filled with 10 g quantities of the culture medium and placed in a fridge (LEC, set temperature: 4° C.) to set for at least 1 hour.

Final thickness of the culture medium sheet is ~5 mm. Petri dishes containing the culture medium sheet are removed from the fridge at least 2 hours before use. The culture medium sheet in the Petri dishes is then inoculated with *Staphylococcus aureus*.

Each is then placed in an incubator at a set temperature.

After the culture has covered more than 50% of the agar surface the dishes are removed from the incubator.

They are place in a fridge, and removed from the fridge at least 2 hours before use.

Preparation of Test Equipment and Materials

Irrigant solution (deionized water containing a therapeutically effective amount of an antibacterial agent, selected from chlorhexidine, povidone iodine, triclosan, metronidazole, cetrimide and chlorhexidine acetate) and the Perspex wound model are pre-conditioned in an oven (Gallenkamp) at set temperature 37° C., for at least 4 hours before use.

For each test, a freshly prepared culture medium sheet with adherent *Staphylococcus aureus* culture is removed from a Petri dish and weighed. The Perspex wound model is then removed from the oven and the culture medium sheet with adherent *Staphylococcus aureus* culture placed at the bottom of the cavity. Application of the dressing to the wound model is as follows: (i) the wound contacting element is carefully placed over the culture medium sheet with adherent *Staphylococcus aureus* culture, (ii) he foam filler is placed on top of this with the irrigant and aspirant tubes running centrally to the top of the cavity (the foam filler is slit to the center to facilitate this), (iii) the side entry port, pre-threaded onto the tubes, is adhesively bonded to the upper surface of the wound model block using an acrylic pressure sensitive adhesive, (iv) the top adhesive coated film is applied over all of the elements and pressed down to give a seal on all sides, and especially around the tube entry/exit point Application of the dressing to the wound model is the same for all tests performed. All tubing used is the same for each experiment (e.g. material, diameter, length).

Simultaneous Irrigation & Aspiration

For the experiment most of the apparatus (not including the pumps, power supply, and connecting tubing to and from the pumps) is placed in an oven (Gallenkamp, set temperature: 37° C.), on the same shelf.

Before starting the irrigation pump a vacuum is drawn on the system to check that the dressing and tube connections are substantially airtight.

The pumping system is controlled to give a pressure at the vacuum vessel of approximately −75 mmHg before opening the system up to include the dressing). Once system integrity has been confirmed, the irrigation pump is started (nominal flow rate: 50 ml/hr), i.e. both pumps running together. Timing of the experiment is started when the advancing water front within the irrigant tube is observed to have reached the top of the dressing.

After 60 minutes, the irrigation pump is stopped, shortly followed by the vacuum (aspiration) pump. Aspirant liquid collected in the vacuum jar is decanted into a glass jar. The vacuum jar is rinsed with ~100 ml of deionized water and this added to the same glass jar. The aspirant solution is then assayed for the *Staphylococcus aureus* quantity present.

Sequential Irrigation & Aspiration

The experimental set up is as for the simultaneous irrigation/aspiration experiment. Before starting the experiment a vacuum is pulled on the system to check that the dressing and tube connections are substantially airtight. The pumping system is controlled to give a pressure at the vacuum vessel of approximately −75 mmHg before opening the system up to include the dressing. Once system integrity has been confirmed, the irrigation pump is started (nominal rate: 186 ml/hr) and run until the advancing water front in the irrigant tube is observed to have reached the top of the dressing.

The pump is temporarily stopped at this point whilst the vacuum line is sealed (using a tube clamp) and the vacuum pump stopped.

Timing of the experiment is from the point the irrigation pump is restarted. The pump is run until 50 ml of irrigant has entered the wound model (just over 16 minutes at the rate of 186 ml/hr). At this point the irrigant pump is stopped.

It is observed that during the filling phase of sequential filling and flushing, air trapped in the model wound cavity caused the top film of the dressing to inflate substantially, to a point approaching failure.

After a further ~44 minutes (60 minutes from the start of the experiment) the vacuum pump is started and the tube clamp on the aspirant line removed. The wound model is aspirated for 5 minutes. Towards the end of this period a small leak is introduced into the top film of the dressing to maximize the amount of fluid drawn from the wound model (it is observed that as the pressure differential between the wound model cavity and the vacuum jar reduced to zero, the flow of aspirant also tended to slow. Introducing a small leak re-established the pressure differential and the flow of aspirant out of the cavity).

Aspirant liquid collected in the vacuum jar is decanted into a glass jar. The vacuum jar is rinsed with ~100 ml of deionized water and this added to the same glass jar. The aspirant solution is then assayed for the *Staphylococcus aureus* quantity present.

Results and Conclusions

Simultaneously irrigating and aspirating the wound model removes or kills more of the adherent *Staphylococcus aureus* on the culture medium sheet placed at the base of the wound model cavity than sequentially filling and emptying the cavity, even though the amount of liquid entering the wound and the duration of the experiment are the same in both cases. Simultaneously irrigating and aspirating also removes more fluid from the model wound.

Example 6

The combination of simultaneous fluid flow (irrigation) with aspiration (under reduced pressure) and actives (PDGF-bb) on wound bed fibroblasts compared with the exposure of wound bed fibroblasts to repeated fill-empty cycles of fluid flow and aspiration.

An apparatus of the present invention was constructed essentially as in FIG. 33 which is an apparatus where an irrigant or fluid of some nature is delivered continually to the wound bed and the resultant wound exudate/fluid mixture is at the same time continually aspirated from the wound.

Alternative systems are known where the wound is subjected to repeated iteration of a cycle of fluid delivery followed by a period of aspiration under reduced pressure.

The apparatus comprised a surrogate wound chamber (Minucells perfusion chamber) in which normal diploid human fibroblasts were cultured on 13 mm diameter (Thermanox polymer) cover slips retained in a two part support (Minnucells Minusheets). Tissues present in the healing wound that must survive and proliferate were represented by the cells within the chamber. Nutrient medium (DMEM with 10% FCS with 1% Buffer All) to simulate an irrigant fluid/wound exudate mixture, was pumped from a reservoir into the lower aspect of the chamber where it bathed the fibroblasts and was removed from the upper aspect of the chamber and returned to a second reservoir. The wound chamber was maintained at less than atmospheric pressure by means of a Vacuum pump in line with the circuit.

The pumps for the circuit were peristaltic pumps acting on silicone (or equivalent) elastic tubing. The circuit was exposed to a vacuum of no more than 10% atmospheric pressure, 950 mbar and atmospheric pressure varied up to a maximum value of 1044 mbar. The internal diameter of the tubing was 1.0 mm. A total volume for the circuit including the chamber and the reservoir of between 100 and 220 ml was used. The flow rates used were at a number of values between 0.1 ml min$^{-1}$ and 2.0 ml$^{-1}$ min$^{-1}$.

An experiment was conducted that simulated conditions that are not uncommon for healing wounds whereby a fluid was delivered to the wound bed and the application of a vacuum is used to remove the mixture of fluid and exudate to a waste reservoir. An air bleed fluid control valve was additionally positioned in the circuit so that on opening the air bleed occurred for a time and closed the fluid flow, the simulated irrigant fluid/wound exudate mixture was evacuated from the chamber and the chamber left empty and the fibroblasts were maintained under a negative pressure relative to the atmosphere. This represents an empty/fill system, 6 cycles of empty/fill were performed with each fill or empty phase lasting 1 hour.

An experiment was conducted using the following 2 scenarios:

Apparatus was constructed essentially as in FIG. 30 but where (a) continuous flow simultaneous aspirate irrigate system with (b) material beneficial to wound healing (PDGF-bb) was present in the nutrient flow bathing the cells.

Apparatus was also constructed essentially as in FIG. 30 but (a) it was operated as an empty/fill system with 6× cycles of 1 hour empty/1 hour fill over a total of 25 hours with (b) the material beneficial to wound healing (PDGF-bb) was present, in the nutrient flow bathing the cells.

Results and Conclusions

The following results were obtained for a circuit comprising a wound chamber as above containing a total volume of nutrient media (104 ml) pumped at a flow rate of 0.2 ml min$^{-1}$, and where vacuum was set at 950 mbar and where atmospheric pressure was varied up to a maximum value of 1044 mbar. The wound chamber and media were held at 37° C. for 25 hours. In one set of wound chambers continuous flow was maintained. In a second set of chambers 6 cycles of empty/fill were performed with each fill or empty phase lasting 1 hour.

In controls (a) operated as empty/fill with 6 cycles of 1 hour empty/1 hour fill, and (b) where PDGF-bb is present, the survival and growth of fibroblasts is inhibited compared to the continuous flow systems.

Where flow circuits consists of (a) continuous flow (SIA) and (b) PDGF-bb is present, the survival and growth of fibroblasts is enhanced to a greater level than empty/fill plus PDGF-bb

| Conditions | Mean of cell activity* after 25 hours. |
|---|---|
| Continuous flow (SIA) plus active (PDGF-bb) | 0.34 |
| Fill empty 6 cycles plus active (PDGF-bb) | 0.22 |

*Cell activity measured with a WST (Tetrazolium based mitochondrial dehdrogenase activity assay).

The combination of actives (PDGF-bb) and continuous fluid flow at 0.2 ml min$^{-1}$ with waste fluid removal under a vacuum of no more than 10% atmospheric pressure, enhances the cell response necessary for wound healing more than the fill empty system (+PDGF-bb).

Example 7

The combination of simultaneous fluid flow (irrigation) and aspiration (under reduced pressure) versus the exposure of wound bed fibroblasts to repeated fill-empty cycles of fluid flow and aspiration.

An apparatus was constructed essentially as in FIG. 33.

The apparatus may be used to represent an apparatus of the present invention where an irrigant fluid is delivered continually to the wound bed and the resultant wound exudate/fluid mixture is at the same time continually aspirated from the wound under reduced pressure and is pumped to waste, or an alternative system where the wound is subjected to repeated iteration of a cycle of fluid delivery followed by a period of aspiration to waste under reduced pressure.

For reasons of economy, aspiration was not carried out to waste, but the aspirate was re-circulated.

The apparatus comprised a surrogate wound chamber (Minucells perfusion chamber) in which normal diploid human fibroblasts were cultured on 13 mm diameter nylon disks retained in a two part support (Minucells Minusheets). Tissues present in the wound bed that must survive and proliferate in the healing process were represented by the cells within the chamber. A bioscaffold matrix (consisting of a Vicryl mesh (90:10 polyglycollic lactic acid) coated with extracellular matrix) was placed in close proximity to the wound bed fibroblasts and all parts were retained between the Minucells Minisheets within the surrogate wound chamber.

Nutrient medium (DMEM with 1% Buffer All) to simulate an irrigant fluid/wound exudate mixture, was pumped from a reservoir (reservoir 1) into the lower aspect of the chamber where it bathed the fibroblasts and was removed from the upper aspect of the chamber to a second reservoir (reservoir 1) and thence returned to reservoir 1.

The circuit also comprised a heat exchanger upstream of the wound chamber (not shown), such that the temperature of the nutrient media bathing the cells reaches between 35° C. and 37° C.

In use as an apparatus of the present invention where an irrigant fluid is delivered continually to the wound bed and the resultant wound exudate/fluid mixture is at the same time continually aspirated from the wound under reduced pressure and is pumped to waste:

The wound chamber was maintained at less than atmospheric pressure by means of a vacuum pump, by which the circuit was exposed to a vacuum of no more than 10% atmospheric pressure, 950 mbar and atmospheric pressure varied up to a maximum value of 1044 mbar, and which also served as a first device downstream of the surrogate wound for moving fluid away from the wound.

The second device for moving fluid through the surrogate wound and applied to the irrigant of and towards the wound chamber is the combination of two peristaltic pumps, pumps 1 and 2 in FIG. 33.

These act on silicone (or equivalent) elastic tubing, the internal diameter of which was 1.0 mm.

A total volume for the circuit including the chamber and the reservoir of between 50 and 220 ml was used. The continuous flow rates used were between 0.1 ml min$^{-1}$ and 2.0 ml$^{-1}$ min$^{-1}$.

In use as a system where the wound is subjected to repeated iteration of a cycle of fluid delivery followed by a period of aspiration to waste under reduced pressure, an air bleed fluid control T-valve was additionally positioned in the circuit upstream of the wound chamber (as shown), such that the valve may be set so that (a) the air bleed is closed for a time and irrigant fluid flows into the wound chamber, (b) the air bleed is opened and irrigant fluid/wound exudate mixture is evacuated from the chamber and (c) air bleed and flow to the chamber are closed off, and the fibroblasts are maintained under a negative pressure relative to the atmosphere.

This represents an empty/fill system with cycles of empty/fill.

The following experiments were conducted using a circuit comprising a wound chamber as above:

1. with a bioscaffold matrix (consisting of a Vicryl mesh (90:10 polyglycollic lactic acid) coated with extracellular matrix) placed in close proximity to the wound bed fibroblasts, (a) containing a total volume of nutrient media (104 ml) pumped at a continuous flow rate of 0.2 ml min$^{-1}$, and where vacuum was set at 950 mbar and where atmospheric pressure varied up to a maximum value of 1044 mbar, over 2.5 day, and (b) operated with 11 cycles of empty/fill performed with each fill or empty phase lasting 1 hour, and where vacuum was set at 950 mbar 2. with the bioscaffold matrix replaced with a matrix consisting of a nylon mesh, (a) containing a total volume of nutrient media (104 ml) pumped at a continuous flow rate of 0.2 ml min$^{-1}$, and where vacuum was set at 950 mbar and where atmospheric pressure varied up to a maximum value of 1044 mbar, over 2.5 day, and (b) operated with 11 cycles of empty/fill performed with each fill or empty phase lasting 1 hour, and where vacuum was set at 950 mbar.

Results and Conclusions

The following results were obtained:

In controls where (a) the apparatus is operated as an empty/fill system with 11× cycles of 1 hour empty/1 hour fill over a total of 2.5 days, and/or (b) a nylon scaffold is used, the migration, and growth of the fibroblasts is inhibited.

However, when the irrigant flow in the circuit is (a) delivered continually to the surrogate wound chamber and the fluid is at the same time continually aspirated from the surrogate wound chamber under vacuum, set at 950 mbar and where atmospheric pressure varied up to a maximum value of 1044 mbar, and (b) a bioscaffold is present, the fibroblasts migrate and proliferate to a greater extent during a 2.5 day period than the control empty/fill circuits.

| Conditions | Mean of cell activity* after 2.5 day hours. N = 3 |
|---|---|
| Continuous flow (SIA) plus synthetic scaffold | 0 |
| Continuous flow (SIA) plus bioscaffold | 0.68 |
| Fill empty 6 cycles at room temperature plus synthetic scaffold | 0 |
| Fill empty 6 cycles plus bioscaffold | 0.46 |

*Cell activity of scaffold measured with a WST (Tetrazolium based mitochondrial dehdrogenase activity assay).

The combination of bioscaffold and continuous fluid flow at 0.2 ml min$^{-1}$ with waste fluid removal under vacuum of no more than 10% atmospheric pressure, 950 mbar and atmospheric pressure varied up to a maximum value of 1044 mbar, enhances the cell response necessary for wound healing more than the empty fill regime, under vacuum.

These act on silicone (or equivalent) elastic tubing, the internal diameter of which was 1.0 mm.

A total volume for the circuit including the chamber and the reservoir of between 50 and 220 ml was used. The continuous flow rates used were between 0.1 ml min$^{-1}$ and 2.0 ml$^{-1}$ min$^{-1}$.

In use as a system where the wound is subjected to repeated iteration of a cycle of fluid delivery followed by a period of aspiration to waste under reduced pressure, an air bleed fluid control T-valve was additionally positioned in the circuit upstream of the wound chamber (as shown), such that the valve may be set so that, (a) the air bleed is closed for a time and irrigant fluid flows into the wound chamber, (b) the air bleed is opened and irrigant fluid/wound exudate mixture is evacuated from the chamber and (c) air bleed and flow to the chamber are closed off, and the fibroblasts are maintained under a negative pressure relative to the atmosphere.

This represents an empty/fill system with cycles of empty/fill.

The following experiments were conducted using a circuit comprising a wound chamber as above 1. with a bioscaffold matrix (consisting of a Vicryl mesh (90:10 polyglycollic lactic acid) coated with extracellular matrix) placed in close proximity to the wound bed fibroblasts, (a) containing a total volume of nutrient media (104 ml) pumped at a continuous flow rate of 0.2 ml min$^{-1}$, and where vacuum was set at 950 mbar and where atmospheric pressure varied up to a maximum value of 1044 mbar, over 2.5 day, and (b) operated with 11 cycles of empty/fill performed with each fill or empty phase lasting 1 hour, and where vacuum was set at 950 mbar 2. with the bioscaffold matrix replaced with a matrix consisting of a nylon mesh, (a) containing a total volume of nutrient media (104 ml) pumped at a continuous flow rate of 0.2 ml min$^{-1}$, and where vacuum was set at 950 mbar and where atmospheric pressure varied up to a maximum value of 1044 mbar, over 2.5 day, and (b) operated with 11 cycles of empty/fill performed with each fill or empty phase lasting 1 hour, and where vacuum was set at 950 mbar.

Example 8

Demonstration of in vitro effects of applying stress to cells in a simulated wound.

Objective

To determine the total amount of collagen deposited by human dermal fibroblasts on silica Flexercell plates following macrostress treatment over a period of time, Methods Cells Human dermal fibroblasts (HS8/BS04) were used. Experiments were performed whereby fibroblasts ($5 \times 10^5$ per well) were seeded in silicone membrane 6 well plates (Flexercell), supplied by Flexcell Intl. Hillsborough, N.C. and subjected to a range of 'macrostress' (macrostress as used in this example refers to stress applied to the cells by way of mechanical stretching) treatments for 48 hours, whereby the cells were subjected to a strewn of 15% (i.e. 15% elongation of the cell substrate) at a frequency of 0.1 Hz on a cycle having a sine wave profile. The Flexercell, Tension Plus™ system is a computer-driven instrument that simulates biological strain conditions using vacuum pressure to deform cells cultured on flexible, matrix-bonded growth surfaces of BioFlex® series culture plates. Following experimentation, media was removed, the cells were washed in PBS and stored at $-70°$ C. until analysed for collagen levels.

The cells were exposed to sequential (SEQ) or simultaneous (SIA) irrigation/aspiration. For SIA, a flow rate of 0.1 ml per minute was used. For sequential, 10 empty/fill cycles were performed over the 48 hour period, each empty/fill taking 1 hour to complete. The media used was DMEM/10% FCS.

Collagen Quantification

The collagen content present on the 6 well plates was determined using a hydroxyl proline quantification assay which 2 ml papain buffer was used to digest any collagen due to the larger surface area.

RT-PCR

Relative quantification of plasminogen inhibitor activiator 2 (PIA-2) and collagen 1a gene expression was determined using the Taqman RT-PCR machine.

RNA Extraction

Cells were scraped from the well in RLN buffer and the RNA from 3 sample wells were pooled using one RNeasy mini column. Control RNA was extracted from fibroblasts grown to confluence in a T175 flask.

RNA extraction from fibroblasts was performed using reagents and protocols described in RNeasy Mini Handbook (Qiagen) and RLN buffer (50 mM Tris-HCl, Sigma, lot 033K8418; 140 mM NaCl, Sigma, lot 013K8930; 1.5 mM $MgCl_2$, Sigma, lot 082K8938; 0.5% (v/v) Igepal (Sigma, lot 102K0025); 10 µl/ml β-mercaptoethanol, Sigma, lot 102K0025, made up to volume in Molecular Biology grade water (Sigma, lot, 23K2444).

Following elution from the spin column in 50 µl water, the RNA was quantified using a spectrophotometer.

cDNA Preparation cDNA was prepared from RNA using Omniscript reverse transcription kit (Qiagen) with Random Hexamer primers (Applied Biosystems, lot G07487). The reaction was completed by heating for 1 hour at $37°$ C. and stored at $-20°$ C. until required.

RT-PCR Primers

Three gene products were selected as they had previously been shown to be up-regulated during Flexercell Macrostress treatment (Kessler, et al, JBC, 276, 39, 36575-36585, 2001). Primers were synthesised by MWG Biotech.

```
Collagen 1a:
F-5' ACA TGC CGA GAC TTG AGA CTC A

R-5' GCA TCC ATA GTA CAT CCT TGG TTA GG
```

(from Wong et al, Tissue Engineering, 8, 6, 979-2002)

```
PAI-2:
F-5' AAT GCA TCC ACA GGG GAT TA

R-5' CGC AGA CTT CTC ACC AAA CA
```

(Designed using Primer 3 software, sequence from accession no. H81869)

```
18S rRNA
F-5' CGG CTA CCA CAT CCA AGG AA

R-5' GCT GGA ATT ACC GCG GCT
```

(18S rRNA housekeeping gene primers previously designed and synthesised by Sigma).

SYBR Green

SYBR green reagent (Applied Biosystems, lot 0505023) master mix was prepared as per manufacturers protocol. Briefly, 50% v/v SYBR green, 0.05% primer 1, 0.05% primer 2, made up to 100% in RNase free water. 5 µl cDNA template and 45 µl SYBR green added per well.

PCR

The RT-PCR was performed using 7700 Taqman RT-PCR system (SOP/BC/227). The run conditions were: (1) $50°$ C. for 2 minutes, (2) $95°$ C. for 10 minutes, $95°$ C. for 15 seconds, (4) $60°$ C. for 1 minute.

Conditions 3 and 4 repeated for a total of 40 cycles.

To ensure a single PCR product had been amplified, a melt analysis on the product was performed using the following conditions: (1) $95°$ C. for 15 seconds, (2) $60°$ C. for 20 seconds, (3) $95°$ C. for 15 seconds A ramp time of 19.59 minutes between stage 2 and 3 was used to determine the degradation temperature.

Discussion

Collagen Quantification

The amount of collagen present in each well of a six well Flexercell plate was determined using the hydroxyproline quantification assay. Fibroblast cells, seeded at either $5 \times 10^3$ or $5 \times 10^5$ per well were grown on laminin coated plates for 72 hours. The absorbance values determined following analysis were very low, showing that the amount of collagen present was also very low. Unfortunately, an error was made when preparing the hydroxyproline standard curve whereby the stock solution was not diluted 10 fold so it was not possible to give an amount of hydroxyproline present. This error would only have affected the standards. The low values showed that this assay was not suitable for measuring such low collagen contents.

A second hydroxyproline determination assay was performed using gas chromatography (GS-MS). This analysis also revealed very low collagen content present in the 6 well plates.

RT-PCR

As the cells only had 72 hours to proliferate and synthesis new collagen, a short length of time, it was decided to look for changes in the level of gene expression, which, generally relates to changes in the amount of protein synthesised as the cells proliferate.

The genes of interest chosen to investigate were collagen 1a and plasminogen activator inhibitor 2 (PIA-2) genes as these had previously been shown to be induced in stressed collagen lattices (Kessler et al, JBC, 276, 39, pp 36575-36585, 2001). The level of gene expression of the genes of interest is expressed as a ratio against 18S rRNA, a housekeeping gene, shown previously (Kessler et al, 2001) to remain at a steady level of expression.

For the RT-PCR experiments, fibroblasts were grown and subjected to 15% strain, 0.1 Hz frequency for 48 hours, with control samples not being subjected to these conditions. Also, they were subjected to either continuous irrigate aspiration of media (SIA), or a series of 1 hour empty/fill cycles (SEQ). All systems were kept under vacuum of ~25 mbar below atmospheric.

The level of PAI-2 gene expression was determined in fibroblasts subjected to the four sets of conditions described above. The results are shown in the table below.

| | |
|---|---|
| SIA only | 1.6 |
| SEQ only | 5.3 |
| SIA plus macrostress | 5.4 |
| SEQ plus macrostress | 5.3 |

The results show that there is an increase in the level of PAI-2 gene expression when fibroblasts in the SIA system are subjected to macrostress (at 15% strain, 0.1 Hz frequency; n=1). However, the level of expression is also elevated in both SEQ and SEQ plus macrostress fibroblasts. Unfortunately, due to technical difficulties during the initial macrostress Flexercell experiments, only one set of experimental plates were available for analysis.

Results and Conclusions

RT-PCR analysis of PAI-2 gene expression showed an increase in the level of expression in SIA plus macrostress compared to SIA only. This demonstrates the effect of macrostress on the activity of the cells in the in vitro wound simulation, and supports the role of macrostress in wound healing.

There was no difference in the level of expression in SEQ and SEQ plus macrostress fibroblasts.

Due to technical difficulties, these results are from an n=1, therefore care needs to be taken when interpreting the results. However, the results indicate that application of macrostress to cells during SIA irrigation leads to increase levels of cell activity, and possibly of collagen production. This reflects on increase in healing activity where stress is applied.

The results of the SEQ analysis are puzzling, and may be the results of an unidentified error in the protocol. Future experiments will be required to confirm this. An alternative hypothesis is that additional stresses induced by the fill/empty cycle may have inadvertently resulted in stress being applied to the control population.

Example 9

In vitro example demonstrating the efficacy of the Flow Stress in stimulating cell activity in a wound model.

An apparatus of the present invention was constructed essentially as in FIG. 33.

The circuit has the means for fluid cleansing of a wound using an apparatus where an irrigant or fluid of some nature is delivered continually to the wound bed and the resultant wound exudate/fluid mixture is at the same time continually aspirated from the wound and is pumped to waste (i.e. simultaneous aspiration/irrigation—SIA). The cell chamber (400) representing the wound bed is held under vacuum to simulate negative pressure (pressure range <10% atmospheric). (For the experiments the aspirant was not pumped to waste but was re-circulated). The circuit was also used to provide a system where the wound is subjected to repeated iteration of a cycle of fluid delivery followed by a period of aspiration under reduced pressure (i.e. sequential irrigation/aspiration—SEQ).

The apparatus comprised a surrogate wound chamber (400) (Minucells perfusion chamber) in which normal diploid human fibroblasts were cultured on 13 mm diameter (Thermanox polymer) cover slips retained in a two part support (Minnucell Minusheets). Tissues present in the healing wound that must survive and proliferate were represented by the cells within the chamber. Nutrient medium (DMEM with 5% FCS with 1% Buffer All) to simulate an irrigant fluid/wound exudate mixture was pumped from a reservoir into the base of chamber where it bathed the fibroblasts and was removed from the top of the chamber and returned to a second reservoir. The wound chamber was maintained at less than atmospheric pressure by means of a Vacuum pump (18A) in line with the circuit. An air bleed fluid control valve was additionally positioned in the circuit so that on opening the air bleed for a time and closing the fluid flow, the simulated irrigant fluid/wound exudate mixture was evacuated from the chamber and the fibroblasts were maintained in a moist environment under a negative pressure relative to the atmosphere.

The pumps for the circuit were peristaltic pumps acting on silicone (or equivalent) elastic tubing. The circuit was exposed to a vacuum of no more than 10% atmospheric pressure, (with a range of 950 mbar to 1044 mbar). The internal diameter of the tubing was 1.0 mm. A total volume for the circuit including the chamber and the reservoir was between 50 and 220 ml. The flow rates used were at 0.1 ml min$^{-1}$ Circuit comprised of an upstream of the wound chamber, a heat exchanger such that the temperature of the nutrient media bathing the cells reaches between 35° C. and 37° C.

Experiments were conducted that simulated conditions not uncommon for healing wounds whereby the nutrient media delivered to the wound site was supplemented by microstress (the term microstress is used in this example to relate to flow stress) provided by increasing the rate of media flow over the cells to 1.4 ml min$^{-1}$ for 6 hours.

An experiment was conducted that simulated conditions that are not uncommon for healing wounds whereby a fluid was delivered to the wound bed and the application of a vacuum is used to remove the mixture of fluid and exudate to a waste reservoir whereby an air bleed fluid control valve was additionally positioned in the circuit so that on opening the air bleed occurred for a time and closed the fluid flow, the simulated irrigant fluid/wound exudate mixture was evacuated from the chamber and the fibroblasts were maintained under a negative pressure relative to the atmosphere. This represents an empty/fill system, 10 cycles of empty/fill were performed with each fill or empty phase lasting 1 hour.

Circuit apparatus were constructed essentially as in FIG. 2 above and consisted of: (a) a control system which contained: (i) empty/fill system with 10× cycles of 1 hour empty/1 hour fill over a total of 48 hours and (ii) the chambers representing the wound bed were exposed to microstress; or (iii) The chambers representing the wound bed were NOT exposed to microstress; (b) The test apparatus: (i) a continuous flow system over a total of 48 hours and (ii) the chambers representing the wound bed were exposed to microstress; or (iii) the chambers representing the wound bed were NOT stimulated by microstress treatment Method in More Detail Cells Human dermal fibroblasts (HS8/BS04) grown at 37° C./5% $CO_2$, in T175 flasks containing 35 ml DMEM/10% FCS media were washed in PBS and lifted using 1× trypsin/EDTA (37° C. for 5 min). Trypsin inhibition was achieved by adding 10 ml DMEM/10% FCS media and the cells pelleted by centrifugation (Hereus Megafuge 1.0R; 1000 rpm for 5 min). The media was discarded and cells re-suspended in 10 ml DMEM/10% FCS. Cells were counted using a haemocytometer and diluted in DMEM/10% FCS to obtain 100,000 cells per ml.

Cells (100 μl of diluted stock) were transferred to each 13 mm Thermanox tissue culture coated cover slip (cat. 174950, lot 591430) in a 24 well plate and incubated for 1 hr at 37° C./5% $CO_2$ to allow cell adherence. After 1 h, 1 ml DMEM/10% FCS media was added per well and the cells incubated overnight in the above conditions.

Following overnight incubation, cells were assessed visually for growth under the microscope and those with growth were inserted into cover slip holders (Vertriebs-Gmbh, cat no. 1300) for assembly in the Minucell chamber (Vertriebs-Gmbh, Cat no. 1301).

Media

Cells were grown in DMEM media (Sigma, no. D6429) supplemented with 10% foetal calf serum; 1-glutamine, non-essential amino acids and penicillin/streptomycin (various lot numbers). Media used in the experimental systems was buffered with Buffer-All media (Sigma, lot 75K2325) to ensure stable pH of the media.

Minucell Flow Systems

Systems (4) were made up as follows: a) SIA (simultaneous irrigate aspirate) only, (b) SEQ (sequential irrigate aspirate) only, (c) SIA plus microstress, (d) SEQ plus microstress Media (50 ml) was transferred to each reservoir bottle. The Minucell chambers were filled with 4 ml media and 6 coverslips inserted. The systems were set-up as shown in FIG. 30 (the pumps were set to run at 0.1 ml/min); hot plates set to 45° C.; Discofix 3-way valves (Arnolds lot 04A2092042 c/z); vacuum pump (Ilmvac VCZ 324, asset no 6481, set to 950 mbar).

Media was circulated at 0.1 ml/l min continuously. In empty/fill systems, the Minucell chambers were emptied by stopping the media flow and switching the 3-way valve to allow air through an attached 0.22 μm filter. When fully emptied, the 3-way valve was closed between the valve and the pump and kept under vacuum. Elevation of the 3-way valve ensured media did not pass through the 0.22 μm filter by gravity flow. After 1 h, the 3-way valve was switched back to the starting position to allow the Minucell chamber to fill and flow rate returned to 0.1 ml/min. Continuous irrigate/aspirate systems were run continuously under vacuum at 0.1 ml/min for 48 h.

The vacuum pump was set to 950 mbar. The atmospheric pressure varied daily, up to a maximum value of 1044 mbar; therefore the difference in pressure between the systems and the atmosphere was always under 10%. The fill/empty systems were treated as per the table below.

Microstress (i.e. Flow Stress)

Microstress stimulation was provided by increasing the flow rate of the media in the system to 1.4 ml/min for the first 6 hours of the experiment. The flow rate was then returned to 0.1 ml/min Fill/empty regime for Minucell chambers.

Day 1 - 4 × empty/fill cycles
Day 2 - 4 × empty fill cycles
Day 3 - 2 × empty/fill cycles and WST assay WST Assay A WST assay to measure the cells mitochondrial activity was performed on 6 coverslips from each system. WST reagent (Roche, lot 102452000) was diluted to 10% v/v in DMEM/5% FCS/buffer all media. The coverslips were removed from the Minucell chamber and washed in 1 ml PBS. PBS was removed and 200 μl WST/DMEM media added. The coverslips were then incubated at 37° C. for 45 min before transferring 150 μl to a 96 well plate. The absorbance at 450 nm with reference at 655 nm was determined using Ascent Multiskan Microtitre plate reader.

Results and Conclusions

The following results were obtained for a circuit comprising a wound chamber as above containing a total volume of nutrient media (104 ml) pumped at a flow rate of 0.1 ml $min^{-1}$ and where vacuum was set at 950 mbar and where atmospheric pressure varied up to a maximum value of 1044 mbar. The wound chamber and media were held at 37° C. for 48 hours and exposed to microstress. In one set of wound chambers continuous flow was maintained. In a second set of chambers 10 cycles of empty/fill were performed with each fill or empty phase lasting 1 hour.

In samples where either (a) empty/fill system with 10× cycles of 1 hour empty/1 hour fill over a total of 48 hours, or (b) the exposure to microstress is omitted, the survival and growth of the fibroblasts is generally relatively poor.

However, when the nutrient medium flow in the first circuit is (a) is delivered continually to the Minucell chamber and the resultant nutrient medium is at the same time continually aspirated from the Minucell chamber under vacuum, and (b) is exposed to microstress, the fibroblasts survive and proliferate to a far greater extent during a 48 hour period than the control empty/fill circuits.

The results are shown in the following table.

| Conditions | Mean of cell activity* after 48 hours. N = 2 |
|---|---|
| Continuous flow (SIA) flow | 0.54 |
| Continuous flow (SIA) plus)microstress | 0.61 |
| Fill/empty 10 cycles | 0.28 |
| Fill empty 10 cycles plus microstress | 0.51 |

*Cell activity measured with a WST (Tetrazolium based mitochondrial dehdrogenase activity assay).

The combination of microstress and continuous fluid flow at 0.1 ml $min^{-1}$ with waste fluid removal under vacuum of no more than 10% atmospheric pressure, (950 mbar and atmospheric pressure varied up to a maximum value of 1044 mbar)

resulted in an improvement in the healing response of the cells. In the fill empty cycle system the improvement was even more pronounced, resulting in an almost doubling of cell activity.

These results suggest that application of microstress (i.e. flow stress) to a wound in both simultaneous and sequential irrigate/aspirate systems may be of significant benefit to wound healing.

Example 10

Using simultaneous irrigate/aspirate (SIA) and sequential irrigate/aspirate (SEQ), the effect of cells as a source of 'actives' on fibroblast proliferation was determined.

Method

Cells

Human dermal fibroblasts (HS8/BS04) grown at 37° C./5% $CO_2$, in T175 flasks containing 35 ml DMEM/10% FCS media were washed in PBS and lifted using 1× trypsin/EDTA (37° C. for 5 min). Trypsin inhibition was achieved by adding 10 ml DMEM/10% FCS media and the cells pelleted by centrifugation (Hereus Megafuge 1.0R; 1000 rpm for 5 min). The media was discarded and cells re-suspended in 10 ml DMEM/10% FCS. Cells were counted using haemocytometer (SOP/CB/007) and diluted in DMEM/10% FCS to obtain 100,000 cells per ml.

Cells (100 µl of diluted stock) were transferred to 13 mm Thermanox tissue culture coated cover slips (Fisher, cat. no. 174950, lot no. 591430) in a 24 well plate and incubated at 37° C. in 5% $CO_2$ to allow for cell adherence. After 1 h, 1 ml DMEM/10% FCS media was added per well and the cells incubated for approximately 5 hours in the above conditions. Cells were serum starved overnight by removing the DMEM/10% FCS and washing the coverslips with 2×1 ml PBS prior to the addition of 1 ml DMEM/0% FCS.

Following overnight incubation, cells were assessed visually for cell adherence under the microscope and those with good adherence were inserted into cover slip holders for assembly in the Minucell chamber.

Media

Cells were grown in DMEM media (Sigma, cat. no. D6429) supplemented with 5% foetal calf serum; 1-glutamine, non-essential amino acids and penicillin/streptomycin. Media used in the experimental systems was buffered with 1% (v/v) Buffer-All media (Sigma, cat. no. B8405, lot. no. 51k2311) to ensure stable pH of the media.

Minucell Flow Systems

Media (50 ml) was transferred to each bottle prior to the autoclaved systems being assembled. The Minucell chambers were filled with 4 ml media prior to coverslips being inserted. The systems were set-up as shown in FIG. 29, set to run at 0.2 ml/min; hot plates, set to 45° C.; Discofix 3-way valves; vacuum pump, (Ilmvac VCZ 310), set to 950 mbar).

SEQ Systems

Media was pumped through the systems at 0.2 ml/l min continuously when the chambers were full. The Minucell chambers were emptied by disconnecting the tubing from the pump and switching the 3-way valve to allow air through an attached 0.22 µm filter. When fully emptied, the 3-way valve was switched to close the system between the valve and the pump and so allowing the formation of a vacuum in the system. Elevation of the 3-way valve ensured media did not pass through the 0.22 µm filter by gravity flow. After 1 h, the 3-way valve was switched back to the starting position to allow the Minucell chamber to fill and the tube reconnected to the pump. The SEQ systems were treated as per the following table.

Fill/empty regime for SEQ systems.

| Time (h) | 0 | 1 | 2 | 3 | 4 | 5 | 6 | 7 | 8 | 20 | 21 | 22 | 23 | 24 |
|---|---|---|---|---|---|---|---|---|---|---|---|---|---|---|
| Empty/fill | F | E | F | E | F | E | F | E | F | E | F | E | W | A |

F = full chamber/flowing;
E = empty chamber/under vacuum;
W = remove coverslips for WST assay;
A = read WST assay result.

SIA Systems

Continuous irrigate aspirate systems were run for 24 h with media irrigating the cells and being aspirated under vacuum set to 950 mbar. The atmospheric pressure varied daily, up to a maximum value of 1048 mbar, therefore the difference in pressure between the systems and the atmosphere was always under 10%.

Cells as Actives Component

The 'cells as actives' component of the flow cell system was provided by Dermagraft (a fibroblast seeded Vicryl mesh). Dermagraft stored at −70° C. was defrosted by placing in a 37° C. water-bath for 1 min and washed ×3 with 50 ml 0.9% v/v NaCl. The Dermagraft was cut into 24×1.1 $cm^2$ squares using a sterile clicker-press and placed into DMEM/5% FCS. For the flow-cell experiments, a number of Dermagraft squares were placed in Media 1 bottle (FIG. 1) immediately prior to the start of the experiment. The presence of live cells in the Dermagraft squares was determined by WST assay when the experiment was terminated.

WST Assay

A WST assay to measure cell mitochondrial activity was performed on the coverslips. WST reagent (Roche, cat. no. 1 644 807, lot no. 11264000) was diluted to 10% v/v in DMEM/10% FCS. The coverslips (n=6) were removed from each Minucell chamber and washed in 1 ml PBS. PBS was removed and 200 µl WST/DMEM media added. The coverslips were then incubated at 37° C. for 45 min before transferring 150 µl to a 96 well plate. The absorbance at 450 nm with reference at 655 nm was determined using Ascent Multiskan Microtitre plate reader.

Results and Conclusions

Figure 34:
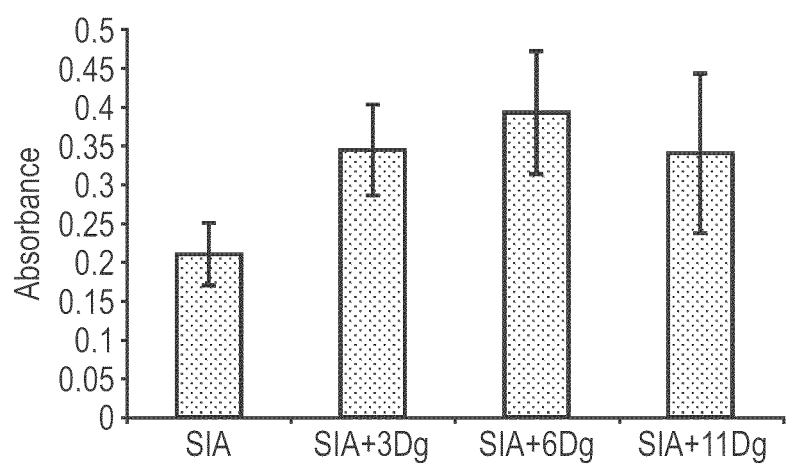
FIG. 34 shows increased WST activity of fibroblasts and thus increased proliferation of cells in a SIA system with actives from cells being added.

The mitochondrial activity of cells grown in SIA and SEQ systems, with or without 'cells as actives' component was determined using the WST assay. The optimal number of Dermagraft squares required was first assessed in a SIA flow cell system. Addition of Dermagraft squares to the media had a beneficial effect, increasing the proliferation rate of seeded fibroblasts (FIG. 34). There was a slight benefit to increasing the number of Dermagraft squares from 3 to 6, although increasing the amount of Dermagraft to 11 squares did not further increase the rate of proliferation. Therefore, for the flow cell experiments, 6 Dermagraft squares were placed in the relevant media bottles. The experiments to show the optimal number of Dermagraft squares also showed that the addition of cells as a source of actives, to the SIA systems, resulted in an increased rate of proliferation (FIG. 34).

Figure 35:
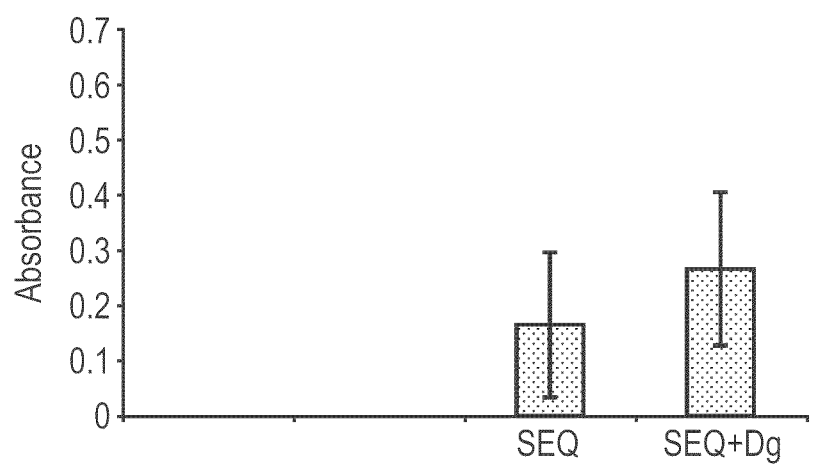
FIG. 35 shows a summary of WST activity of fibroblasts in SEQ systems for 24 h with or with "cells as actives" component (n=3).

Treatment of fibroblasts by the addition of 'cells acting as a source of actives' to the media, increased the rate of proliferation in SIA and the SEQ systems after 24 hours (FIGS. 34 & 35).

This beneficial effect was observed in both SAI and the SEQ flow systems.

While the above detailed description has shown, described, and pointed out novel features as applied to various embodiments, it will be understood that various omissions, substitutions, and changes in the form and details of the device or process illustrated may be made without departing from the spirit of the disclosure. Additionally, the various features and processes described above may be used independently of one another, or may be combined in various ways. All possible combinations and subcombinations are intended to fall within the scope of this disclosure. Many of the embodiments described above include similar components, and as such, these similar components can be interchanged in different embodiments.

Although the invention has been disclosed in the context of certain embodiments and examples, it will be understood by those skilled in the art that the invention extends beyond the specifically disclosed embodiments to other alternative embodiments and/or uses and obvious modifications and equivalents thereof. Accordingly, the invention is not intended to be limited by the specific disclosures of preferred embodiments herein.

What is claimed is:

1. An apparatus for aspirating and irrigating a wound, comprising
    a conformable wound filler configured to be placed in the wound;
    a wound cover configured to form a seal over the wound;
    a fluid supply tube configured to supply fluid to the wound;
    at least one fluid reservoir configured to be connected to the fluid supply tube;
    an outlet tube configured to supply negative pressure to the wound;
    a negative pressure source configured to be connected to the outlet tube, the negative pressure source configured to apply negative pressure to the wound by cycling between a first negative pressure level and a second negative pressure level;
    a control device configured to:
        control the fluid supply and the negative pressure source such that fluid is supplied to the wound while fluid is simultaneously aspirated from the wound;
        maintain a desired balance of fluid removed from the wound and fluid supplied to the wound; and
        control the fluid supply such that fluid from the at least one fluid reservoir is supplied to the wound in a plurality of fluid supply cycles, each fluid supply cycle supplying a volume of fluid with a time period between fluid supply cycles.

2. The apparatus of claim 1, wherein the at least one fluid reservoir contains an anti-bacterial fluid.

3. The apparatus of claim 1, further comprising a biodegradable scaffold configured to be positioned under the wound cover and configured to be placed in contact with the wound.

4. The apparatus of claim 1, wherein the at least one fluid reservoir contains fluid that is capable of supplying thermal energy to the wound.

5. The apparatus of claim 1, further comprising an inflatable module configured to provide mechanical stress to the wound, the inflatable module configured to be positioned under the wound cover.

6. The apparatus of claim 5, wherein the inflatable module is configured to be inflated via fluid expansion.

7. The apparatus of claim 1, wherein the at least one fluid reservoir contains a physiologically active component.

8. The apparatus of claim 1, further comprising an irrigant pump configured to supply fluid to the wound.

9. The apparatus of claim 1, wherein the fluid supply is configured to pulse the volume of fluid into the wound.

10. The apparatus of claim 9, wherein the fluid supply is configured to pulse the volume of fluid at least once per minute.

11. The apparatus of claim 1, further comprising a module that imposes a linear flow on the irrigant fluid.

12. The apparatus of claim 1, wherein the fluid supply tube is configured to apply shear stress to the wound.

13. The apparatus of claim 1, wherein the control device is further configured to cyclically vary a velocity of fluid supplied to the wound.

14. The apparatus of claim 1, further comprising a manifold configured to allow passage of fluid supplied to the wound and fluid removed from the wound in a linear stream.

15. The apparatus of claim 1, wherein the control device is further configured to maintain a desired fluid flow velocity at the wound.

16. The apparatus of claim 1, wherein the negative pressure source is configured to: vary an amplitude of the negative pressure at the wound and simultaneously vary an amplitude of a flow velocity of the fluid supplied to the wound.

17. The apparatus of claim 1, further comprising an inlet manifold that is configured to expand and apply positive pressure to the wound.

18. The apparatus of claim 1, further comprising a flattened manifold layer positioned between the wound filler and the wound cover, the manifold layer comprising at least one aperture for passage of negative pressure.

19. The apparatus of claim 1, further comprising a synthetic scaffold positionable under the wound cover and configured to be placed in contact with the wound.

20. The apparatus of claim 1, wherein the at least one fluid reservoir is demountable.

21. The apparatus of claim 1, wherein the at least one fluid reservoir is connected to the fluid supply tube via an interface.

* * * * *

UNITED STATES PATENT AND TRADEMARK OFFICE
CERTIFICATE OF CORRECTION

Page 1 of 3

PATENT NO.       : 8,529,548 B2
APPLICATION NO.  : 12/976949
DATED            : September 10, 2013
INVENTOR(S)      : Blott et al.

It is certified that error appears in the above-identified patent and that said Letters Patent is hereby corrected as shown below:

On the Title Page

Column 1 (page 4, item [56]) at line 29, Under Other Publications, change "(Chuvashia" to --(Chuvash--.

Column 1 (page 4, item [56]) at line 37, Under Other Publications, change "exerpt" to --expert--.

Column 1 (page 4, item [56]) at line 46, Under Other Publications, change "Absorable" to --Absorbable--.

Column 1 (page 4, item [56]) at line 47, Under Other Publications, change "Obsterics" to --Obstetrics--.

Column 1 (page 5, item [56]) at line 13, Under Other Publications, change "salmoncida" to --salmonicida--.

In the Specification

Column 13 at lines 53-54, Change "dressing;" to --dressing.--.

Column 17 at line 40, Change "wound," to --wound.--.

Column 19 at line 41, Change "a not" to --as not--.

Column 20 at line 3, Change "flange" to --flange.--.

Column 27 at line 21, Change "Kanthal™ Alkrothal™" to --Kanthal™, Alkrothal™,--.

Column 27 at line 27, Change "expoxy" to --epoxy--.

Column 27 at lines 60-61, Change "Allevyn (™, Smith & Nephew) and Tielle (™, Johnson & Johnson)," to --Allevyn™, (Smith & Nephew) and Tielle™, (Johnson & Johnson),--.

Column 30 at line 20, Change "and/or and/or" to --and/or--.

Column 31 at line 65, Change "and or" to --and/or--.

Signed and Sealed this
Eighth Day of July, 2014

Michelle K. Lee
*Deputy Director of the United States Patent and Trademark Office*

CERTIFICATE OF CORRECTION (continued)
U.S. Pat. No. 8,529,548 B2

Column 33 at line 28, Change "aspiration" to --aspiration.--.
Column 34 at line 4, Change "appplication" to --application--.
Column 34 at line 23, Change "maybe" to --may be--.
Column 34 at line 24, Change "maybe" to --may be--.
Column 36 at line 55, Change "though" to --through--.
Column 39 at line 8, Change "equilibrium" to --equilibrium.--.
Column 39 at line 44, Change "stretopkinase," to --streptokinase,--.
Column 39 at line 51, Change "gutathione" to --glutathione--.
Column 40 at line 35, Change "stretopkinase," to --streptokinase,--.
Column 40 at line 42, Change "gutathione" to --glutathione--.
Column 41 at line 1, Change "bupivicaine," to --bupivacaine,--.
Column 42 at line 67, Change "poli" to --poly--.
Column 43 at line 11, Change "glycosoaminoglycans," to --glycosaminoglycans,--.
Column 47 at line 54, Change "maybe" to --may be--.
Column 52 at line 14, Change "and than" to --and then--.
Column 61 at line 62, Change "frustroconical," to --frustoconical,--.
Column 62 at line 34, Change "frustroconical," to --frustoconical,--.
Column 66 at line 11, Change "hereinbefore" to --hereinbefore.--.
Column 66 at line 19, Change "hereinbefore" to --hereinbefore.--.
Column 66 at line 27, Change "hereinbefore" to --hereinbefore.--.
Column 66 at line 37, Change "hereinbefore" to --hereinbefore.--.
Column 66 at lines 47-48, Change "hereinbefore" to --hereinbefore.--.
Column 66 at lines 59-60, Change "hereinbefore" to --hereinbefore.--.
Column 68 at line 14, Change "wounds" to --wounds.--.
Column 70 at line 42, Change "wounds" to --wounds.--.
Column 73 at line 37, Change "~75" to -- -75--.
Column 73 at line 57, Change "~75" to -- -75--.
Column 75 at line 52, Change "circuits" to --circuits.--.
Column 75 at line 64, Change "activity" to --activity.--.
Column 79 at line 42, Change "was was" to --was--.
Column 80 at line 17, Change "dehdrogenase" to --dehydrogenase--.
Column 80 at line 22, Change "atmostpheric" to --atmospheric--.
Column 81 at line 51, Change "point" to --point.--.
Column 84 at line 14, Change "dehdrogenase" to --dehydrogenase--.
Column 84 at line 46, Change "polyglycollic" to --polyglycolic--.

CERTIFICATE OF CORRECTION (continued)
U.S. Pat. No. 8,529,548 B2

Column 85 at line 34, Change "polyglycollic" to --polyglycolic--.

Column 85 at line 43, Change "mbar" to --mbar.--.

Column 86 at lines 16-17, Change "dehdrogenase" to --dehydrogenase--.

Column 86 at line 47, Change "above" to --above:--.

Column 86 at line 50, Change "polyglycollic" to --polyglycolic--.

Column 86 at line 58, Change "mbar" to --mbar.--.

Column 87 at line 9, Change "time," to --time.--.

Column 87 at line 42, Change "activiator" to --activator--.

Column 88 at line 40, Change "minutes," to --minutes, (3)--.

Column 88 at line 47, Change "seconds" to --seconds.--.

Column 89 at lines 60-61, Change "on increase" to --an increase--.

Column 90 at line 46, Change "$min^{-1}$" to --$min^{-1}$.--.

Column 91 at line 11, Change "treatment" to --treatment.--.

Column 91 at line 19, Change "(Hereus" to --(Heraeus--.

Column 91 at lines 45-46, Change "microstress" to --microstress.--.

Column 91 at line 54, Change "ml/l min" to --ml/min--.

Column 92 at line 8, Change "ml/min" to --ml/min.--.

Column 92 at line 27, Change "Microtitre" to --Microtiter--.

Column 92 at line 62, Change "dehdrogenase" to --dehydrogenase--.

Column 92 at line 66, Change "atmostpheric" to --atmospheric--.

Column 93 at line 23, Change "(Hereus" to --(Heraeus--.

Column 93 at line 57, Change "ml/l min" to --ml/min--.

Column 94 at line 42, Change "Microtitre" to --Microtiter--.